(12) United States Patent
Huigens, III et al.

(10) Patent No.: US 12,060,334 B2
(45) Date of Patent: Aug. 13, 2024

(54) 3-SUBSTITUTED PHENAZINE DERIVATIVES AS ANTIMICROBIAL AGENTS

(71) Applicant: University of Florida Research Foundation, Incorporated, Gainesville, FL (US)

(72) Inventors: Robert William Huigens, III, Williston, FL (US); Hongfen Yang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 28 days.

(21) Appl. No.: 17/692,536

(22) Filed: Mar. 11, 2022

(65) Prior Publication Data
US 2022/0289689 A1 Sep. 15, 2022

Related U.S. Application Data

(60) Provisional application No. 63/160,336, filed on Mar. 12, 2021.

(51) Int. Cl.
*C07D 241/46* (2006.01)
*A61K 31/498* (2006.01)

(52) U.S. Cl.
CPC .................... *C07D 241/46* (2013.01)

(58) Field of Classification Search
CPC ................... C07D 241/46; A61K 31/498
See application file for complete search history.

(56) References Cited

U.S. PATENT DOCUMENTS

| | | | |
|---|---|---|---|
| 3,609,153 | A | 9/1971 | Cook et al. |
| 3,910,925 | A | 10/1975 | Kreider |
| 9,856,225 | B2 | 1/2018 | Huigens et al. |
| 11,008,290 | B2 | 5/2021 | Huigens et al. |
| 11,053,205 | B2 | 7/2021 | Huigens et al. |
| 2005/0165044 | A1 | 7/2005 | Boykin et al. |
| 2008/0121873 | A1 | 5/2008 | Katakura et al. |
| 2009/0227626 | A1 | 9/2009 | Deraeve et al. |
| 2010/0144693 | A1 | 6/2010 | Bush et al. |
| 2010/0160346 | A1 | 6/2010 | Barnham et al. |
| 2012/0165370 | A1 | 6/2012 | Tang et al. |
| 2014/0336221 | A1 | 11/2014 | Pegan et al. |
| 2016/0355487 | A1 | 12/2016 | Huigens et al. |
| 2018/0265475 | A1 | 9/2018 | Huigens et al. |
| 2018/0312473 | A1 | 11/2018 | Huigens et al. |
| 2020/0010432 | A1 | 1/2020 | Huigens et al. |

FOREIGN PATENT DOCUMENTS

| | | | |
|---|---|---|---|
| GB | 1206866 | A2 | 9/1970 |
| WO | WO 2015/100331 | A2 | 7/2015 |
| WO | WO 2017/011730 | A2 | 1/2017 |

OTHER PUBLICATIONS

Bao et al. (Medicinal Chemistry (Sharjah, United Arab Emirates) (2020), 16(3), 413-421). Abstract.*
Yang et al. (Journal of Medicinal Chemistry (2021), 64(11), 7275-7295).*
[No Author Listed], A Dictionary of Chemistry. Oxford University Press. 2020;8:159.
Burger, Isosterism and bioisosterism in drug design. Prog Drug Res. 1991;37:287-371. doi: 10.1007/978-3-0348-7139-6_7.
Invitation to Pay Additional Fees for PCT/US2016/042439, mailed Sep. 20, 2016.
International Search Report and Written Opinion for PCT/US2016/042439, mailed Jan. 5, 2017.
International Preliminary Report on Patentability for PCT/US2016/042439, mailed Jan. 25, 2018.
International Search Report and Written Opinion for PCT/US2014/072165, mailed Jul. 13, 2015.
International Preliminary Report on Patentability for PCT/US2014/072165, mailed Jul. 7, 2016.
Invitation to Pay Additional Fees for PCT/US2016/053295, mailed Mar. 27, 2017.
International Search Report and Written Opinion for PCT/US2016/053295, mailed Jun. 9, 2017.
International Preliminary Report on Patentability for PCT/US2016/053295, mailed Apr. 5, 2018.
International Search Report and Written Opinion for PCT/US2018/018538, mailed on May 4, 2018.

(Continued)

*Primary Examiner* — Bruck Kifle
(74) *Attorney, Agent, or Firm* — Wolf, Greenfield & Sacks, P.C.

(57) ABSTRACT

The present invention provides phenazine derivatives, such as compounds of Formula (I). The compounds of the invention are expected to be antimicrobial agents and may act by a microbial warfare strategy (e.g., a reactive oxygen species (ROS)-based competition strategy). The present invention also provides compositions, kits, uses, and methods that involve the compounds of the invention, which may be useful in preventing or treating a microbial infection (e.g., a bacterial infection or mycobacterial infection) in a subject, inhibiting the growth and/or reproduction of a microorganism (e.g., a bacterium or mycobacterium), killing a microorganism (e.g., a bacterium or mycobacterium), inhibiting the formation and/or growth of a biofilm, reducing or clearing a biofilm, and/or disinfecting a surface.

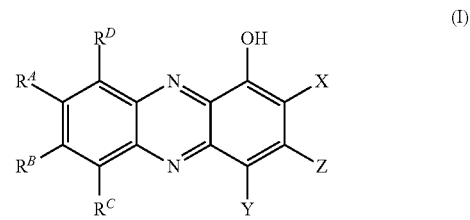

55 Claims, 13 Drawing Sheets

(56) References Cited

OTHER PUBLICATIONS

International Preliminary Report on Patentability for PCT/US2018/018538, mailed on Aug. 29, 2019.
[No Author Listed], Clinical and Laboratory Standards Institute. 2009. Methods for dilution antimicrobial susceptibility tests for bacteria that grow aerobically; approved standard, 8th edition (A17-A18), Clinical and Laboratory Standard, Wayne, PA, 2009.
[No Author Listed], PubChem SID No. 141693651 dated Aug. 20, 2012.
[No Author Listed], CID 66651970. Compound Summary. Nov. 30, 2012. http://pubchem.ncbi.nlm.nih.gov/compound/66651970 . [last accessed Mar. 31, 2015]. 4 pages.
Abouelhassan et al., A Phytochemical-Halogenated Quinoline Combination Therapy Strategy for the Treatment of Pathogenic Bacteria. ChemMedChem. Jul. 2015; 10(7):1157-62. doi: 10.1002/cmdc.201500179. Epub May 15, 2015.
Abouelhassan et al., Discovery of quinoline small molecules with potent dispersal activity against methicillin-resistant Staphylococcus aureus and Staphylococcus epidermidis biofilms using a scaffold hopping strategy. Bioorg Med Chem Lett. Nov. 1, 2014;24(21):5076-80. doi: 10.1016/j.bmcl.2014.09.009. Epub Sep. 15, 2014.
Abouelhassan et al., Rapid kill assessment of an N-arylated NH125 analogue against drug-resistant microorganisms. Medchemcomm. Jan. 29, 2019;10(5):712-716. doi: 10.1039/c8md00613j.
Abouelhassan et al., Recent Progress in Natural-Product-Inspired Programs Aimed to Address Antibiotic Resistance and Tolerance. J Med Chem. Sep. 12, 2019;62(17):7618-7642. doi: 10.1021/acs.jmedchem.9b00370. Epub Apr. 18, 2019. Author Manuscript, 51 pages.
Abouelhassan et al., Transcript Profiling of MRSA Biofilms Treated with a Halogenated Phenazine Eradicating Agent: A Platform for Defining Cellular Targets and Pathways Critical to Biofilm Survival. Angew Chem Int Ed Engl. Nov. 19, 2018;57(47):15523-15528. doi: 10.1002/anie.201809785. Epub Oct. 25, 2018. Author Manuscript, 12 pages.
Albrecht et al., Anion Receptors Based on a Quinoline Backbone. EurJOC. Jun. 2007;2007(17):2850-2585. doi: 10.1002/ejoc.200700130. Epub May 16, 2007.
Almohamad et al., Influence of isolate origin and presence of various genes on biofilm formation by Enterococcus faecium. FEMS Microbiology Letters, 2014;353(2):151-156. https://doi.org/10.1111/1574-6968.12418.
Archer et al., Staphylococcus aureus biofilms: properties, regulation, and roles in human disease. Virulence. Sep.-Oct. 2011;2(5):445-59. doi: 10.4161/viru.2.5.17724. Epub Sep. 1, 2011.
Balaban et al., Bacterial persistence as a phenotypic switch. Science. Sep. 10, 2004;305(5690):1622-5. Epub Aug. 12, 2004.
Basak et al., Halogenated quinolines discovered through reductive amination with potent eradication activities against MRSA, MRSE and VRE biofilms. Org. Biomol. Chem., 2015;13:10290-10294. Doi: 10.1039/C5OB01883H.
Basak et al., Synthetically Tuning the 2-Position of Halogenated Quinolines: Optimizing Antibacterial and Biofilm Eradication Activities via Alkylation and Reductive Amination Pathways. Chemistry. Jun. 27, 2016;22(27):9181-9. doi: 10.1002/chem.201600926. Epub Jun. 1, 2016.
Bhattacharya et al., Prevention and treatment of Staphylococcus aureus biofilms. Expert Rev Anti Infect Ther. 2015;13(12):1499-516. doi: 10.1586/14787210.2015.1100533. Epub Nov. 13, 2015. Author Manuscript, 30 pages.
Birkofer et al., Bacteriostatic effect of phenazine derivatives on Mycobacterium tuberculosis, type gallinaceus. Naturwissenschaften. 1949;36:93.
Bjarnsholt, T., The role of bacterial biofilms in chronic infections. APMIS Suppl. May 2013;(136):1-51. doi: 10.1111/apm.12099.
Blair et al., Molecular mechanisms of antibiotic resistance. Nat Rev Microbiol. Jan. 2015;13(1):42-51. doi: 10.1038/nrmicro3380. Epub Dec. 1, 2014.
Blanchard et al., Neomycin Sulfate Improves the Antimicrobial Activity of Mupirocin-Based Antibacterial Ointments. Antimicrob Agents Chemother. Nov. 23, 2015;60(2):862-72. doi: 10.1128/AAC.02083-15.
Borrero et al., Phenazine antibiotic inspired discovery of potent bromophenazine antibacterial agents against Staphylococcus aureus and Staphylococcus epidermidis. Org Biomol Chem. Feb. 14, 2014;12(6):881-6. doi: 10.1039/c3ob42416b.
Brackman et al., Quorum sensing inhibitors as anti-biofilm agents. Curr Pharm Des. 2015;21(1):5-11.
Breitmaier et al., Carbon-13 nuclear magnetic resonance chemical shifts of substituted phenazines. J. Org. Chem., 1976;41(12):2104-2108. DOI: 10.1021/jo00874a008.
Briard et al., QSAR Accelerated Discovery of Potent Ice Recrystallization Inhibitors. Scientific Reports 2016;6(Article No. 26403). doi: 10.1038/srep26403.
Brown et al., Antibacterial drug discovery in the resistance era. Nature. Jan. 21, 2016;529(7586):336-43. doi: 10.1038/nature17042.
Brown et al., New Targets and Screening Approaches in Antimicrobial Drug Discovery. Chem. Rev., 2005;105(2):759-774. DOI: 10.1021/cr0301160.
Camilli et al., Bacterial small-molecule signaling pathways. Science. Feb. 24, 2006;311(5764):1113-6. doi: 10.1126/science.1121357. Author Manuscript, 9 pages.
Ceri et al., The Calgary Biofilm Device: new technology for rapid determination of antibiotic susceptibilities of bacterial biofilms. J Clin Microbiol. Jun. 1999;37(6):1771-6. doi: 10.1128/JCM.37.6.1771-1776.1999.
Ch'ng et al., Biofilm-associated infection by enterococci. Nat Rev Microbiol. Jan. 2019;17(2):82-94. doi: 10.1038/s41579-018-0107-z. Erratum in: Nat Rev Microbiol. Nov. 20, 2018.
Chambers et al., Waves of resistance: Staphylococcus aureus in the antibiotic era. Nat Rev Microbiol. Sep. 2009;7(9):629-41. doi: 10.1038/nrmicro2200.
Clatworthy et al., Targeting virulence: a new paradigm for antimicrobial therapy. Nat Chem Biol. Sep. 2007;3(9):541-8.
Colomer-Winter et al., Manganese acquisition is essential for virulence of Enterococcus faecalis. PLoS Pathog. Sep. 20, 2018;14(9):e1007102. doi: 10.1371/journal.ppat.1007102.
Conda-Sheridan et al., Potential Chemopreventive Agents Based on the Structure of the Lead Compound 2-Bromo-1-hydroxyphenazine, Isolated from Streptomyces Species, Strain CNS284. J. Med. Chem., 2010;53(24):8688-8699. DOI: 10.1021/jm1011066.
Conlon et al., Activated ClpP kills persisters and eradicates a chronic biofilm infection. Nature. Nov. 21, 2013;503(7476):365-70. doi: 10.1038/nature12790. Epub Nov. 13, 2013.
Conlon et al., Staphylococcus aureus chronic and relapsing infections: Evidence of a role for persister cells: An investigation of persister cells, their formation and their role in S. aureus disease. Bioessays. Oct. 2014;36(10):991-6. doi: 10.1002/bies.201400080. Epub Aug. 6, 2014.
Davies et al., Understanding biofilm resistance to antibacterial agents. Nat Rev Drug Discov. Feb. 2003;2(2):114-22.
Deraeve et al., Bis-8-hydroxyquinoline ligands as potential anti-Alzheimer agents. New J. Chem., 2007;31:193-195. DOI: 10.1039/B616085A.
Di Vaira et al., Clioquinol, a Drug for Alzheimer's Disease Specifically Interfering with Brain Metal Metabolism: Structural Characterization of Its Zinc(II) and Copper(II) Complexes. Inorg. Chem., 2004;43(13):3795-3797. DOI: 10.1021/ic0494051.
Donlan et al., Biofilms: survival mechanisms of clinically relevant microorganisms. Clin Microbiol Rev. Apr. 2002;15(2):167-93. doi: 10.1128/CMR.15.2.167-193.2002.
Dörwald et al., Side Reactions in Organic Synthesis: A Guide to Successful Synthesis Design. Preface. Wiley 2005. DOI: 10.1002/352760426X.
Emmanuvel et al., NaIO4/LiBr-mediated Diastereoselective Dihydroxylation of Olefins: A Catalytic Approach to the Prevost-Woodward Reaction. Org. Lett., 2005;7(22):5071-5074. DOI: 10.1021/ol052080n.
Eun et al., DCAP: A Broad-Spectrum Antibiotic That Targets the Cytoplasmic Membrane of Bacteria. J. Am. Chem. Soc., 2012;134(28):11322-11325. DOI: 10.1021/ja302542j.

(56) References Cited

OTHER PUBLICATIONS

Evangelopoulos et al., Improving the Tuberculosis Drug Development Pipeline. Chem Biol Drug Des, 86: 951-960. doi:10.1111/cbdd.12549.
Ex parte Cao, Decision rendered by the Board of Patent Appeals and Interferences in U.S. Appl. No. 10/696,862 on Sep. 21, 2011.
Fitzpatrick, M.A., Real-world antibiotic needs for resistant Gram-negative infections. Lancet Infect Dis. Oct. 2020;20(10):1108-1109. doi: 10.1016/S1473-3099(20)30178-X. Epub Jun. 4, 2020.
Flemming et al., Biofilms: an emergent form of bacterial life. Nat Rev Microbiol. Aug. 11, 2016;14(9):563-75. doi: 10.1038/nrmicro.2016.94.
Fletcher et al., Draining the moat: disrupting bacterial biofilms with natural products. Tetrahedron 2014;70(37):6373-6383.
Garrison et al., An Efficient Buchwald-Hartwig/Reductive Cyclization for the Scaffold Diversification of Halogenated Phenazines: Potent Antibacterial Targeting, Biofilm Eradication, and Prodrug Exploration. J Med Chem. May 10, 2018;61(9):3962-3983. doi: 10.1021/acs.jmedchem.7b01903. Epub Apr. 19, 2018.
Garrison et al., Bromophenazine Derivatives with Potent Inhibition, Dispersion and Eradication Activities against *Staphylococcus aureus* Biofilms. RSC Adv. Nov. 25, 2015;5:1120-4. doi: 10.1039/C4RA08728C.
Garrison et al., Eradicating Bacterial Biofilms with Natural Products and Their Inspired Analogues that Operate Through Unique Mechanisms. Curr Top Med Chem. Dec. 14, 2016;17(14):1-8. 12 pages. doi: 10.2174/1568026617666161214150959.
Garrison et al., Halogenated Phenazines that Potently Eradicate Biofilms, MRSA Persister Cells in Non-Biofilm Cultures, and Mycobacterium tuberculosis. Angew. Chem. Int. Ed., 54:14819-14823. doi:10.1002/anie.201508155.
Garrison et al., Structure-Activity Relationships of a Diverse Class of Halogenated Phenazines That Targets Persistent, Antibiotic-Tolerant Bacterial Biofilms and Mycobacterium tuberculosis. J Med Chem. Apr. 28, 2016;59(8):3808-25. doi: 10.1021/acs.jmedchem.5b02004. Epub Apr. 6, 2016.
Gershon et al., Antimicrobial Activity of 8-Quinolinol, Its Salts with Salicylic Acid and 3-Hydroxy-2-Naphthoic Acid, and the Respective Copper (II) Chelates in Liquid Culture. Appl. Environ. Microbiol. Jan. 1963;11(1):62-65.
Geske et al., Small Molecule Inhibitors of Bacterial Quorum Sensing and Biofilm Formation. J. Am. Chem. Soc., 2005;127(37):12762-12763. DOI: 10.1021/ja0530321.
Gillaspy et al., Role of the accessory gene regulator (agr) in pathogenesis of *Staphylococcal osteomyelitis*. Infect Immun. Sep. 1995;63(9):3373-80. doi: 10.1128/iai.63.9.3373-3380.1995.
Gupta et al., Evidence for Inhibition of Topoisomerase 1A by Gold(III) Macrocycles and Chelates Targeting Mycobacterium tuberculosis and Mycobacterium abscessus. Antimicrob Agents Chemother. Apr. 26, 2018;62(5):e01696-17. doi: 10.1128/AAC.01696-17.
Guttenberger et al., Recent developments in the isolation, biological function, biosynthesis, and synthesis of phenazine natural products. Bioorg Med Chem. Nov. 15, 2017;25(22):6149-6166. doi: 10.1016/j.bmc.2017.01.002. Epub Jan. 5, 2017.
Hall-Stoodley et al., Bacterial biofilms: from the natural environment to infectious diseases. Nat Rev Microbiol. Feb. 2004;2(2):95-108. doi: 10.1038/nrmicro821.
Harbarth et al., Antibiotic research and development: business as usual? J Antimicrob Chemother. 2015;70(6):1604-7. doi: 10.1093/jac/dkv020. Epub Feb. 10, 2015.
Harrison et al., Copper and Quaternary Ammonium Cations Exert Synergistic Bactericidal and Antibiofilm Activity against Pseudomonas aeruginosa. Antimicrob. Agents Chemother. Aug. 2008;52(8):2870-2881.
Harrison et al., Microtiter susceptibility testing of microbes growing on peg lids: a miniaturized biofilm model for high-throughput screening. Nat Protoc. Jul. 2010;5(7):1236-54. doi: 10.1038/nprot.2010.71. Epub Jun. 10, 2010.
Hassan et al., Mechanism of the antibiotic action pyocyanine. J. Bacteriol. 1980; 141:156-63. doi: https://doi.org/10.1128/jb.141.1.156-163.1980.
Hassani et al., Novel lavendamycin analogues as antitumor agents: synthesis, in vitro cytotoxicity, structure-metabolism, and computational molecular modeling studies with NAD(P)H:quinone oxidoreductase 1. J Med Chem. Dec. 1, 2005;48(24):7733-49.
Heim et al., A mouse model of *Staphylococcus* catheter-associated biofilm infection. Methods in Molecular Biology Jan. 2014;1106:183-191. DOI: 10.1007/978-1-62703-736-5_17.
Hentzer et al., Attenuation of Pseudomonas aeruginosa virulence by quorum sensing inhibitors. EMBO J. Aug. 1, 2003;22(15):3803-15.
Hirt et al., Antimicrobial Peptide GL13K is Effective in Reducing Biofilms of Pseudomonas aeruginosa. Antimicrob. Agents Chemother. Oct. 2013;57(10):4903-4910.
Hoque et al., Membrane Active Small Molecules Show Selective Broad Spectrum Antibacterial Activity with No Detectable Resistance and Eradicate Biofilms. J. Med. Chem., 2015;58(14):5486-5500. DOI: 10.1021/acs.jmedchem.5b00443.
Hoque et al., Selective and broad spectrum amphiphilic small molecules to combat bacterial resistance and eradicate biofilms. Chem. Commun., 2015;51:13670-13673. DOI: 10.1039/C5CC05159B.
Hughes et al., Antibacterials from the sea. Chemistry. Nov. 8, 2010;16(42): 12512-25. doi: 10.1002/chem.201001279.
Imai et al., A new antibiotic selectively kills Gram-negative pathogens. Nature. Dec. 2019;576(7787):459-464. doi: 10.1038/s41586-019-1791-1. Epub Nov. 20, 2019. Erratum in: Nature. Apr. 2020;580(7802):E3. Author Manuscript, 45 pages.
Jennings et al., Biofilm-eradicating properties of quaternary ammonium amphiphiles: simple mimics of antimicrobial peptides. Chembiochem. Oct. 13, 2014;15(15):2211-5. doi: 10.1002/cbic.201402254. Epub Aug. 21, 2014.
Jordan et al., Tamoxifen: a most unlikely pioneering medicine. Nat Rev Drug Discov. Mar. 2003;2(3):205-13.
Keren et al., Persister cells and tolerance to antimicrobials. FEMS Microbiol Lett. Jan. 15, 2004;230(1):13-8.
Kim et al., A new class of synthetic retinoid antibiotics effective against bacterial persisters. Nature. Apr. 5, 2018;556(7699):103-107. doi: 10.1038/nature26157. Epub Mar. 28, 2018. Author Manuscript, 22 pages.
Klevens et al., Estimating health care-associated infections and deaths in U.S. hospitals, 2002. Public Health Rep. Mar.-Apr. 2007;122(2):160-6.
Kostakioti et al., Bacterial biofilms: development, dispersal, and therapeutic strategies in the dawn of the postantibiotic era. Cold Spring Harb Perspect Med. Apr. 1, 2013;3(4):a010306. doi: 10.1101/cshperspect.a010306.
Kwan et al., Lyngbyoic acid, a "tagged" fatty acid from a marine cyanobacterium, disrupts quorum sensing in Pseudomonas aeruginosa. Mol Biosyst. Apr. 2011;7(4):1205-1216. doi: 10.1039/c0mb00180e.
Kwast et al., N-Aryl-2-nitrosoanilines as intermediates in the synthesis of substituted phenazines from nitroarenes. Tetrahedron Lett. Nov. 30, 2011;52(48):6484-8. doi: 10.1016/j.tetlet.2011.09.113.
Laursen et al., Phenazine natural products: biosynthesis, synthetic analogues, and biological activity. Chem Rev. Mar. 2004;104(3):1663-86. doi: 10.1021/cr020473j.
Lechner et al., *Staphylococcus aureus* persisters tolerant to bactericidal antibiotics. J Mol Microbiol Biotechnol. 2012;22(4):235-44. doi: 10.1159/000342449. Epub Sep. 14, 2012.
Lewis et al., Persister cells, dormancy and infectious disease. Nat Rev Microbiol. Jan. 2007;5(1):48-56. Epub Dec. 4, 2006.
Lewis, K., Persister cells. Annu Rev Microbiol. 2010;64:357-72. doi: 10.1146/annurev.micro.112408.134306.
Lewis et al., Platforms for antibiotic discovery. Nat Rev Drug Discov. May 2013;12(5):371-87. doi: 10.1038/nrd3975.
Lewis, K., Persister cells: molecular mechanisms related to antibiotic tolerance. Handb Exp Pharmacol. 2012;(211):121-33. doi: 10.1007/978-3-642-28951-4_8.
Lewis, K., The Science of Antibiotic Discovery. Cell. Apr. 2, 2020;181(1):29-45. doi: 10.1016/j.cell.2020.02.056. Epub Mar. 19, 2020.

(56) References Cited

OTHER PUBLICATIONS

Li et al., Synthetic group A streptogramin antibiotics that overcome Vat resistance. Nature. Oct. 2020;586(7827):145-150. doi: 10.1038/s41586-020-2761-3. Epub Sep. 23, 2020.
Ling et al., A new antibiotic kills pathogens without detectable resistance. Nature. Jan. 22, 2015;517(7535):455-9. doi: 10.1038/nature14098. Epub Jan. 7, 2015. Erratum in: Nature. Apr. 16, 2015;520(7547):388. Author Manuscript, 37 pages.
Liu et al., Instructive Advances in Chemical Microbiology Inspired by Nature's Diverse Inventory of Molecules. ACS Infect Dis. Apr. 10, 2020;6(4):541-562. doi: 10.1021/acsinfecdis.9b00413. Epub Jan. 6, 2020. Author Manuscript, 45 pages.
Machan et al., Interaction between Pseudomonas aeruginosa and *Staphylococcus aureus*: description of an anti-*Staphylococcal* substance. J Med Microbiol. Apr. 1991;34(4):213-7. doi: 10.1099/00222615-34-4-213.
Marler et al., Cancer Chemopreventive Potential of Aromathecins and Phenazines, Novel Natural Product Derivatives. Anticancer Research Dec. 2010;30(12):4873-4882.
McCune et al., Microbial Persistence. Journal of Experimental Medicine Mar. 1966;123(3):469-486. DOI: 10.1084/jem.123.3.469.
Miller et al., Quorum sensing in bacteria. Annu Rev Microbiol. 2001;55:165-99. doi: 10.1146/annurev.micro.55.1.165.
Mitchell et al., Scaffold-Hopping of Multicationic Amphiphiles Yields Three New Classes of Antimicrobials. ChemBioChem 2015;16:2299. https://doi.org/10.1002/cbic.201500381.
Motika et al., Gram-Negative Antibiotic Active Through Inhibition of an Essential Riboswitch. J Am Chem Soc. Jun. 17, 2020;142(24):10856-10862. doi: 10.1021/jacs.0c04427. Epub Jun. 8, 2020. Author Manuscript, 16 pages.
Mukherjee et al., Bacterial quorum sensing in complex and dynamically changing environments. Nat Rev Microbiol. Jun. 2019;17(6):371-382. doi: 10.1038/s41579-019-0186-5. Author Manuscript, 28 pages.
Munita et al., Mechanisms of Antibiotic Resistance. Microbiol Spectr. Apr. 2016;4(2):10.1128/microbiolspec.VMBF-0016-2015. doi: 10.1128/microbiolspec. VMBF-0016-2015. Author Manuscript, 37 pages.
Musk et al., Chemical countermeasures for the control of bacterial biofilms: effective compounds and promising targets. Curr Med Chem. 2006;13(18):2163-77.
Navarro et al., Image-Based 384-Well High-Throughput Screening Method for the Discovery of Skyllamycins A to C as Biofilm Inhibitors and Inducers of Biofilm Detachment in Pseudomonas aeruginosa. Antimicrob. Agents Chemother. Feb. 2014;58(2):1092-1099.
Ng et al., Bacterial quorum-sensing network architectures. Annu Rev Genet. 2009;43:197-222. doi: 10.1146/annurev-genet-102108-134304.
Otto et al., Staphylococcal biofilms. Curr Top Microbiol Immunol. 2008;322:207-28.
Parker et al., Implementation of permeation rules leads to a FabI inhibitor with activity against Gram-negative pathogens. Nat Microbiol. Jan. 2020;5(1):67-75. doi: 10.1038/s41564-019-0604-5. Epub Nov. 18, 2019. Author Manuscript, 33 pages.
Patcher et al., The Wohl-Aue Reaction. I. Structure of Benzo [a] phenazine Oxides and Syntheses of 1,6-Dimethoxyphenazine and 1,6-Dichlorophenazine. J. Am. Chem. Soc., 1951;73(10):4958-4961. DOI: 10.1021/ja01154a144.
Payne et al., Drugs for bad bugs: confronting the challenges of antibacterial discovery. Nat Rev Drug Discov. Jan. 2007;6(1):29-40.
Perez-Lago et al., Persistent Infection by a Mycobacterium tuberculosis Strain That Was Theorized to Have Advantageous Properties, as It Was Responsible for a Massive Outbreak. J. Clin. Microbiol. Nov. 2015;53(11):3423-3429.
Prachayasittikul et al., 8-Hydroxyquinolines: a review of their metal chelating properties and medicinal applications. Drug Des Devel Ther. Oct. 4, 2013;7:1157-78. doi: 10.2147/DDDT.S49763. eCollection 2013.
Price-Whelan et al., Rethinking 'secondary' metabolism: physiological roles for phenazine antibiotics. Nat Chem Biol. Feb. 2006;2(2):71-8. doi: 10.1038/nchembio764. Erratum in: Nat Chem Biol. Apr. 2006;2(4):221.
Priyaja et al., Pyocyanin induced in vitro oxidative damage and its toxicity level in human, fish and insect cell lines for its selective biological applications. Cytotechnology. Jan. 2016;68(1):143-55. doi: 10.1007/s10616-014-9765-5.
Projan et al., Why is big Pharma getting out of antibacterial drug discovery? Curr Opin Microbiol. Oct. 2003;6(5):427-30.
Quah et al., N-acetylcysteine inhibits growth and eradicates biofilm of Enterococcus faecalis. J Endod. Jan. 2012;38(1):81-5. doi: 10.1016/j.joen.2011.10.004. Epub Nov. 21, 2011.
Rabin et al., Agents that inhibit bacterial biofilm formation. Future Med Chem. 2015;7(5):647-71. doi: 10.4155/fmc.15.7.
Rewcastle et al., Potential antitumor agents. 51. Synthesis and antitumor activity of substituted phenazine-1-carboxamides. J. Med. Chem., 1987;30(5):843-851. DOI: 10.1021/jm00388a017.
Richter et al., Predictive compound accumulation rules yield a broad-spectrum antibiotic. Nature. May 18, 2017;545(7654):299-304. doi: 10.1038/nature22308. Epub May 10, 2017.
Shi et al., Pyrazinamide inhibits trans-translation in Mycobacterium tuberculosis. Science. Sep. 16, 2011;333(6049):1630-2. doi: 10.1126/science.1208813. Epub Aug. 11, 2011.
Smith et al., Optimized arylomycins are a new class of Gram-negative antibiotics. Nature. Sep. 2018;561(7722):189-194. doi: 10.1038/s41586-018-0483-6. Epub Sep. 12, 2018.
Snowden et al., Biofilm-Infected Intracerebroventricular Shunts Elicit Inflammation within the Central Nervous System. Infect. Immun. Sep. 2012;80(9):3206-3214.
Spellberg et al., Combating Antimicrobial Resistance: Policy Recommendations to Save Lives. IDSA Policy Paper. Clinical Infectious Diseases. 2011:52(Suppl 5):S397. doi: 10.1093/cid/cir153.
Stringer et al., Improved Small-Molecule Macroarray Platform for the Rapid Synthesis and Discovery of Antibacterial Chalcones. ACS Comb. Sci., 2011;13(2):175-180. DOI: 10.1021/co100053p.
Taiwo et al., Mechanism of tiron as scavenger of superoxide ions and free electrons. Spectroscopy 2008;22(6):491-498. http://dx.doi.org/10.3233/SPE-2008-0362.
Uckay et al., Foreign body infections due to *Staphylococcus epidermidis*. Ann Med. 2009;41(2):109-19. doi: 10.1080/07853890802337045.
Vaidya et al., Derivatives of 8-Hydroxy-2-Quinolineacrylic Acid. II. J Med Pharm Chem. Mar. 1962;5:389-97. doi: 10.1021/jm01237a017.
Vippagunta et al., Crystalline solids. Advanced Drug Delivery Reviews 2001;48(1):3-26. https://doi.org/10.1016/S0169-409X(01)00097-7.
Vivian et al., The Practical Synthesis of 1-Phenazinol. Nature 1956;178:753. doi:10.1038/178753a0.
Wang et al., Endogenous Phenazine Antibiotics Promote Anaerobic Survival of Pseudomonas aeruginosa via Extracellular Electron Transfer. J. Bacteriol. 2010;192: 365-69. doi: 10.1128/JB.01188-09.
Waters et al., Quorum sensing: cell-to-cell communication in bacteria. Annu Rev Cell Dev Biol. 2005;21:319-46. doi: 10.1146/annurev.cellbio.21.012704.131001.
Weidmann et al., Lactate dehydrogenase-release assay: a reliable, nonradioactive technique for analysis of cytotoxic lymphocyte-mediated lytic activity against blasts from acute myelocytic leukemia. Ann Hematol. Mar. 1995;70(3):153-8. doi: 10.1007/BF01682036.
Wolcott et al., The role of biofilms: are we hitting the right target? Plast Reconstr Surg. Jan. 2011;127 Suppl 1:28S-35S. doi: 10.1097/PRS.0b013e3181fca244.
Wolff et al., Burger's Medicinal Chemistry and Drug Discovery. vol. 1, Principles and Practice, Fifth Edition. John Wiley & Sons 1994. New York. pp. 975-977.
Wood et al., Bacterial Persister Cell Formation and Dormancy. Appl. Environ. Microbiol. Dec. 2013;79(23):7116-7121.
Wood, T.K., Combatting bacterial persister cells. Biotechnol Bioeng. Mar. 2016;113(3):476-83. doi: 10.1002/bit.25721. Epub Sep. 3, 2015.

(56) References Cited

OTHER PUBLICATIONS

Worthington et al., Small molecule control of bacterial biofilms. Org. Biomol. Chem., 2012;10:7457-7474. DOI: 10.1039/C2OB25835H.

Wright, G.D., Molecular mechanisms of antibiotic resistance. Chem Commun (Camb). Apr. 14, 2011;47(14):4055-61. doi: 10.1039/c0cc05111j. Epub Feb. 1, 2011.

Wröbel et al., Reactivity and substituent effects in the cyclization of N-aryl-2-nitrosoanilines to phenazines. Tetrahedron Lett. Apr. 2017;73(22):3147-52. doi: 10.1016/j.tet.2017.04.046.

Wu et al., Biofilms in Chronic Wounds: Pathogenesis and Diagnosis. Trends Biotechnol. May 2019;37(5):505-517. doi: 10.1016/j.tibtech.2018.10.011. Epub Nov. 26, 2018.

Wu et al., Synthetic furanones inhibit quorum-sensing and enhance bacterial clearance in Pseudomonas aeruginosa lung infection in mice. J Antimicrob Chemother. Jun. 2004;53(6):1054-61. Epub Apr. 29, 2004.

Xiao et al., Progress towards a stable cephalosporin-halogenated phenazine conjugate for antibacterial prodrug applications. Bioorg Med Chem Lett. Nov. 15, 2020;30(22):127515. doi: 10.1016/j.bmcl.2020.127515. Epub Aug. 27, 2020. Author Manuscript, 11 pages.

Yan et al., Surviving as a Community: Antibiotic Tolerance and Persistence in Bacterial Biofilms. Cell Host Microbe. Jul. 10, 2019;26(1):15-21. doi: 10.1016/j.chom.2019.06.002. Author Manuscript, 15 pages.

Yang et al., A Highly Potent Class of Halogenated Phenazine Antibacterial and Biofilm-Eradicating Agents Accessed Through a Modular Wohl-Aue Synthesis. Sci Rep. May 17, 2017;7(1):2003. doi: 10.1038/s41598-017-01045-3.

Yang et al., Design, synthesis and biological evaluation of a halogenated phenazine-erythromycin conjugate prodrug for antibacterial applications. Org Biomol Chem. Feb. 25, 2021;19(7):1483-1487. doi: 10.1039/d0ob02428g. Author Manuscript, 9 pages.

Young et al., Confronting the scientific obstacles to global control of tuberculosis. J Clin Invest. Apr. 1, 2008;118(4):1255-1265. doi: 10.1172/JCI34614.

Zhang et al., Synthesis and Biological Evaluation of Novel 2-Methoxypyridylamino-Substituted Riminophenazine Derivatives as Antituberculosis Agents. Molecules 2014; 19(4):4380-4394; doi: 10.3390/molecules19044380.

Zoysa et al., Antimicrobial Peptides with Potential for Biofilm Eradication: Synthesis and Structure Activity Relationship Studies of Battacin Peptides. J. Med. Chem., 2015;58(2):625-639. DOI: 10.1021/jm501084q.

U.S. Appl. No. 15/744,319, filed Jan. 12, 2018, Huigens et al.
U.S. Appl. No. 15/107,531, filed Jun. 23, 2016, Huigens et al.
U.S. Appl. No. 15/762,456, filed Mar. 22, 2018, Huigens et al.
U.S. Appl. No. 16/486,694, filed Aug. 16, 2019, Huigens et al.
PCT/US2016/042439, Sep. 20, 2016, Invitation to Pay Additional Fees.
PCT/US2016/042439, Jan. 5, 2017, International Search Report and Written Opinion.
PCT/US2016/042439, Jan. 25, 2018, International Preliminary Report on Patentability.
PCT/US2014/072165, Jul. 13, 2015, International Search Report and Written Opinion.
PCT/US2014/072165, Jul. 7, 2016, International Preliminary Report on Patentability.
PCT/US2016/053295, Mar. 27, 2017, Invitation to Pay Additional Fees.
PCT/US2016/053295, Jun. 9, 2017, International Search Report and Written Opinion.
PCT/US2016/053295, Apr. 5, 2018, International Preliminary Report on Patentability.
PCT/US2018/018538, May 4, 2018, International Search Report and Written Opinion.
PCT/US2018/018538, Aug. 29, 2019, International Preliminary Report on Patentability.

\* cited by examiner

3-SUBSTITUTED PHENAZINE DERIVATIVES AS ANTIMICROBIAL AGENTS

RELATED APPLICATIONS

The present application claims priority under 35 U.S.C. § 119(e) to U.S. Provisional Patent Application No. 63/160,336, filed Mar. 12, 2021, which is incorporated herein by reference.

GOVERNMENT SUPPORT

This invention was made with government support under GM128621 awarded by the National Institutes of Health. The government has certain rights in the invention.

BACKGROUND OF THE INVENTION

Novel agents that target multidrug resistant bacteria are of critical importance due to significant clinical challenges posed by these important human pathogens.[1-5] During infection, bacteria can rapidly develop resistance to conventional antibiotic therapies using a multitude of mechanisms, which include: (1) target mutation to impede antibiotic binding, (2) alterations in membrane chemistry to reduce drug penetration, (3) increased efflux pump activity to reduce intracellular concentrations of antibiotic, (4) overproduction of antibacterial target, and (5) enzymatic deactivation of antibiotics.[1,5-10] In contrast to resistance, free-floating planktonic bacteria communicate through quorum sensing to coordinate virulent behaviors,[11-13] including the formation of surface-attached biofilm communities composed of enriched populations of dormant persistent cells innately tolerant to antibiotics.[14-20] Bacterial biofilms are credited as the primary cause of chronic and recurring infections.[1,20-23] As such, new agents capable of targeting antibiotic-resistant bacteria through mechanisms that eradicate surface-attached biofilms are of considerable interest to human health.

Despite extraordinary chemical diversity, conventional antibiotics operate through relatively few modes of action.[5,6] Multiple classes of antibiotics inhibit bacterial ribosomes to impede protein synthesis (e.g., macrolides, tetracyclines, aminoglycosides) while other classes inhibit cell wall synthesis (e.g., beta-lactams, glycopeptides).[1,5,6] In addition, select antibiotic therapies inhibit DNA synthesis (e.g., quinolones), RNA polymerase (e.g., rifamycin), and folate synthesis (e.g., sulfonamides), while polymyxins target and disrupt bacterial membranes.[1,5,6]

Significant efforts to identify novel antibiotics that operate through unique modes of action have been made to overcome resistant and tolerant bacterial infections. A few recent discoveries in the antibiotic arena include the identification of teixobactin (targeting lipid II)[24], darobactin (inhibits BamA, an essential chaperone and translocator that folds outer membrane proteins)[25], G0775 (synthetic arylomycin that covalently modifies and inhibits LepB, a membrane-bound protease that cleaves signal sequences from preproteins)[26], the development of eNTRy rules to guide synthetic conversion of Gram-positive antibacterials into broad-spectrum agents,[27-29] and new group A streptogramin antibiotic analogues that overcome virginiamycin acetyltransferase (Vat) resistance.[30] In addition, recent progress has been made to identify agents that can effectively treat persister/biofilm infections in mouse models, including: ClpP protease-activating agent ADEP-4 (synthetic acyldepsipeptide)[31] and membrane-disrupting retinoid CD437.[32]

We have identified a series of halogenated phenazines (HP) that demonstrate antibacterial and biofilm eradication activities through a unique mechanism (FIG. 1).[33-39] For example, we have identified phenazine antibiotics (e.g., pyocyanin, phenazine-1-carboxylic acid) utilized by *Pseudomonas aeruginosa* to eradicate established *Staphylococcus aureus* infections during Cystic Fibrosis (CF) disease progression.[40-43] Interspecies competition between *P. aeruginosa* and *S. aureus* has been reported.[40,42] We have also identified a series of phenazine antibiotics and non-natural phenazines, which were tested for antibacterial activities against *S. aureus* and *S. epidermidis*.[33] We discovered that 2-bromo-1-hydroxyphenazine 1, initially isolated from a marine *Streptomyces* strain, displayed potent antibacterial activities against *S. aureus* among the naturally-occurring phenazines in our collection (1, MIC=6.25 μM against *S. aureus* & *S. epidermidis*). Since our initially discovery that 1 exhibits good antibacterial activities against Gram-positive pathogens, we have synthesized a diversity of HPs 2 that have shown potency and utility as probes to better understand biofilm viability.

SUMMARY OF THE INVENTION

The present invention provides novel halogenated phenazine derivatives (HPs, HP analogues), such as compounds of Formulae (I):

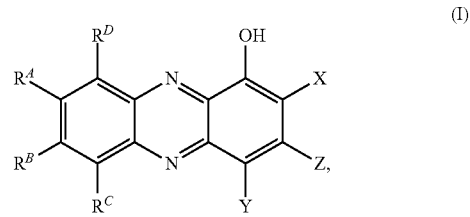

(I)

and salts, hydrates, solvates, polymorphs, co-crystals, tautomers, stereoisomers, isotopically labeled compounds, and prodrugs thereof.

Exemplary compounds of the invention include, but are not limited to:

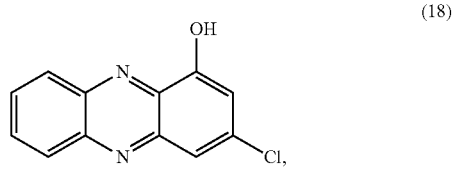

(18)

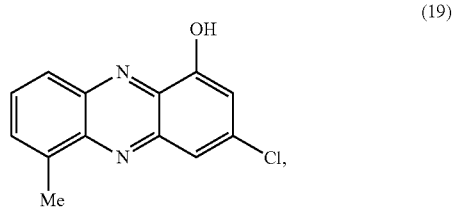

(19)

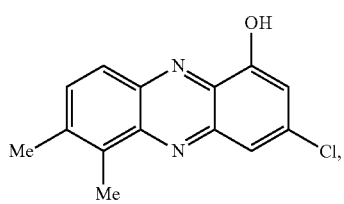
(20)
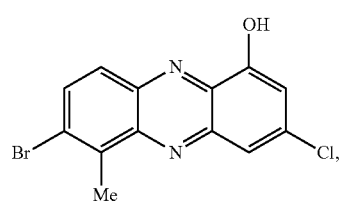
(21)
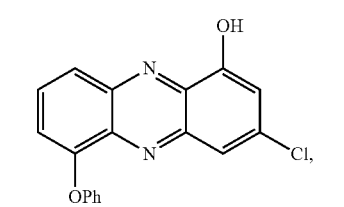
(22)
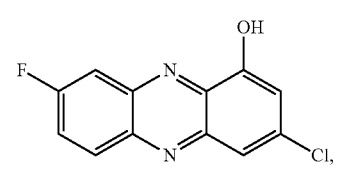
(23)
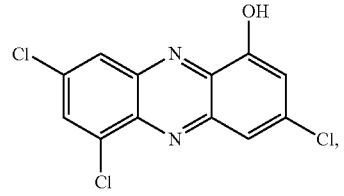
(24)
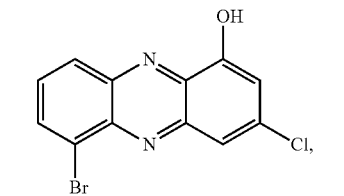
(25)
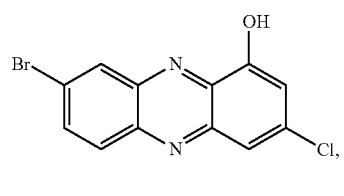
(26)
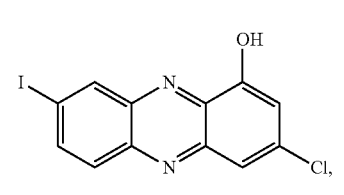
(27)
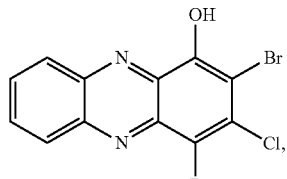
(28)
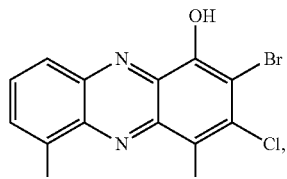
(29)
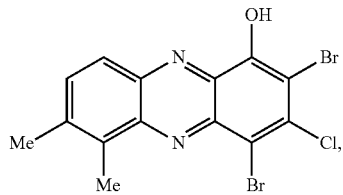
(30)
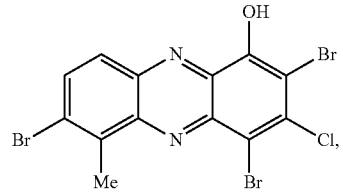
(31)
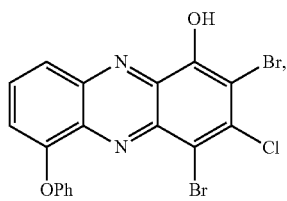
(32)
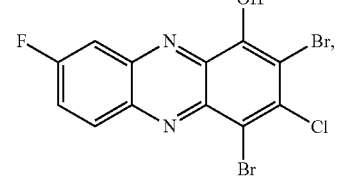
(33)
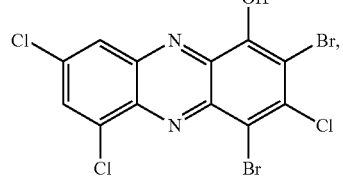
(34)
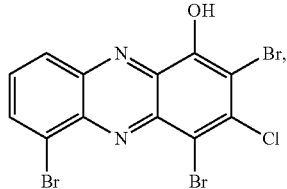
(35)

(36) 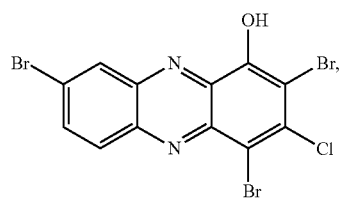

(37) 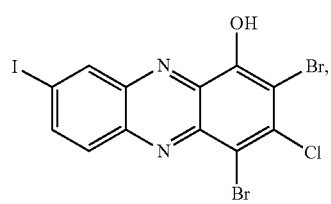

(42) 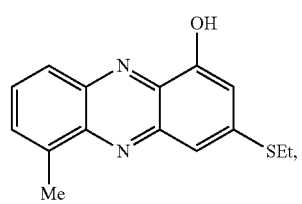

(43) 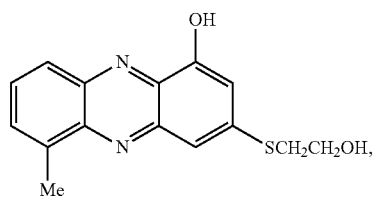

(44) 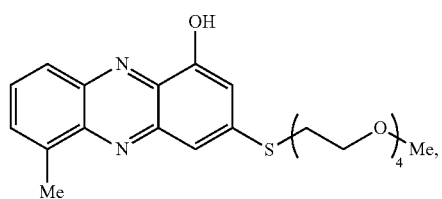

(45) 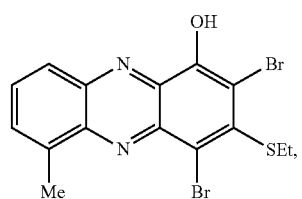

(46) 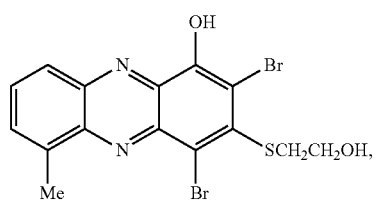

(47) 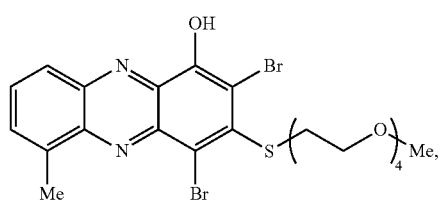

(150) 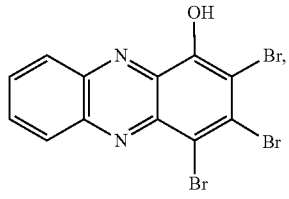

and pharmaceutically acceptable salts, solvates, hydrates, polymorphs, co-crystals, tautomers, stereoisomers, isotopically labeled compounds, and prodrugs thereof.

The compounds of the invention may exhibit antimicrobial activity (e.g., antibacterial activity). Without wishing to be bound by any particular theory, it is thought that the compounds of the invention may act by a microbial warfare strategy (e.g., a reactive oxygen species (ROS)-based competition strategy) similar to the one employed by *Pseudomonas aeruginosa* (*P. aeruginosa*). The inventive compounds may generate ROS in, near, or around a microorganism (e.g., bacterium, mycobacterium, archaeon, protist, fungus, or parasite), which may be toxic to the microorganism. Moreover, the inventive compounds may be able to reduce, inhibit, and/or remove biofilms (e.g., *Staphylococcus aureus* biofilms (e.g., MRSA biofilms) and/or *Staphylococcus epidermidis* biofilms (e.g., MRSE biofilms)). The inventive compounds preferably have minimal or no adverse side effects. In certain embodiments, the inventive compounds have low cytotoxicity with respect to mammalian cells and/or demonstrate low hemolysis activity. Compared with known compounds, the compounds described herein may be more potent, have wider therapeutic window, and/or may be more soluble in water.

In another aspect, the present invention provides compositions including a compound of the invention and optionally an excipient. In certain embodiments, the composition includes an effective amount of the compound for disinfecting a surface. In certain embodiments, the composition is a pharmaceutical composition including a compound of the invention and optionally a pharmaceutically acceptable excipient. In certain embodiments, a pharmaceutical composition of the invention includes an effective amount of a compound of the invention for administration to a subject. In certain embodiments, the pharmaceutical composition is useful in a method of the invention (e.g., a method of treating a microbial infection, preventing a microbial infection, inhibiting the growth of a microorganism, inhibiting the reproduction of a microorganism, killing a microorganism, inhibiting the formation and/or growth of a biofilm, reducing or removing a biofilm, or disinfecting a surface). In certain embodiments, the microorganism is a microorganism described herein. In certain embodiments, the microorganism is a bacterium. In certain embodiments, the bacterium is a Gram-positive bacterium (e.g., a *Staphylococcus* species or *Enterococcus* species). In certain embodiments, the bacterium is a Gram-negative bacterium (e.g., an *Acinetobacter* species). In certain embodiments, the microorganism is a mycobacterium (e.g., a strain of *Mycobacterium tuberculosis*).

Another aspect of the present invention relates to methods of treating and/or preventing a microbial infection in a subject in need thereof, the method including administering to the subject a therapeutically or prophylactically effective amount of a compound or pharmaceutical composition of the invention. In certain embodiments, the microbial infection is treated and/or prevented by the inventive methods. The microbial infections that may be treated and/or prevented by the inventive methods include, but are not limited to, microbial respiratory tract infections, microbial gastrointestinal tract infections, microbial urogenital tract infections, microbial bloodstream infections, microbial ear infections, microbial skin infections, microbial oral infections, microbial dental infections, microbial wound or surgical site infections, microbial infections associated with cystic fibrosis, and microbial infections associated with implanted devices. In certain embodiments, the microbial infection described herein is a bacterial infection. In certain embodiments, the bacterium causing the bacterial infections is a Gram-positive bacterium (e.g., a *Staphylococcus* species or *Enterococcus* species). In certain embodiments, the bacterium causing the bacterial infections is a Gram-negative bacterium (e.g., an *Acinetobacter* species). In certain embodiments, the microbial infection described herein is a mycobacterial infection (e.g., an infection caused by *Mycobacterium tuberculosis*). In certain embodiments, the subject is a human. In certain embodiments, the subject is a human with cystic fibrosis. In certain embodiments, the subject is a non-human animal.

In another aspect, the present invention provides methods of inhibiting the growth of a microorganism (e.g., a bacterium, mycobacterium, archaeon, protist, fungus, or parasite) in vitro or in vivo.

In yet another aspect, the present invention provides methods of inhibiting the reproduction of a microorganism (e.g., a bacterium, mycobacterium, archaeon, protist, fungus, or parasite) in vitro or in vivo.

In yet another aspect, the present invention provides methods of killing a microorganism (e.g., a bacterium, mycobacterium, archaeon, protist, fungus, or parasite) in intro or in vivo.

In certain embodiments, an inventive method includes contacting a microorganism (e.g., bacterium, mycobacterium, archaeon, protist, fungus, or parasite) with a compound or pharmaceutical composition of the invention in an amount effective at inhibiting the growth and/or reproduction of or killing the microorganism.

Another aspect of the invention relates to methods of inhibiting the formation and/or growth of, reducing, or removing a biofilm, the method including contacting the biofilm with an effective amount of a compound or pharmaceutical composition of the invention. In certain embodiments, the biofilm includes a microorganism (e.g., a bacterium, mycobacterium, archaeon, protist, fungus, or parasite). In certain embodiments, the biofilm includes bacteria. The biofilm may include one or more species of bacteria and/or other microorganisms.

Another aspect of the present invention relates to methods of disinfecting a surface, the methods including contacting the surface with an effective amount of a compound or composition of the invention. In certain embodiments, the surface is a biological surface (e.g., skin). In certain embodiments, the surface is a non-biological surface.

Another aspect of the present invention relates to kits comprising a container with a compound or composition (e.g., pharmaceutical composition) of the invention. The kits of the invention may include a single dose or multiple doses of the compound or pharmaceutical composition thereof. The provided kits may be useful in a method of the invention (e.g., a method of treating a microbial infection, preventing a microbial infection, inhibiting the growth of a microorganism (e.g., bacterium, mycobacterium, archaeon, protist, fungus, or parasite), inhibiting the reproduction of a microorganism, killing a microorganism, inhibiting the formation and/or growth of a biofilm, reducing or removing a biofilm, or disinfecting a surface). A kit of the invention may further include instructions for using the kit (e.g., instructions for using the compound or composition (e.g., pharmaceutical composition) included in the kit).

In another aspect, the present invention provides uses of the compounds and pharmaceutical compositions of the invention for manufacturing a medicament for treating and/or preventing a microbial infection.

In another aspect, the present invention provides the compounds and pharmaceutical compositions of the invention for use in methods of preventing and/or treating a microbial infection.

In another aspect, the present invention provides the compounds and pharmaceutical compositions of the invention for treating and/or preventing a microbial infection.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, Examples, and Claims.

Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, the bond ⁓ is a single bond, the dashed line - - - is a single bond or absent, and the bond ═ or ≡ is a single or double bond.

Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

When a range of values ("range") is listed, it is intended to encompass each value and subrange within the range. A range is inclusive of the values at the two ends of the range unless otherwise provided. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl" or "$C_{1-20}$ heteroalkyl"). In certain embodiments, a heteroalkyl group refers to a saturated group having from 1 to 12 carbon atoms and 1 or more heteroatoms within the parent chain ("hetero$C_{1-12}$ alkyl"). In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 20 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C═C double bond for which the stereochemistry is not specified (e.g., —CH═CHCH$_3$ or

)

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 20 carbon atoms, at least one double bond, and 1 or more heteroatoms within the parent chain ("heteroC$_{2-20}$ alkenyl" or "C$_{2-20}$ heteroalkenyl"). In certain embodiments, a heteroalkenyl group refers to a group having from 2 to 12 carbon atoms, at least one double bond, and 1 or more heteroatoms within the parent chain ("heteroC$_{2-12}$ alkenyl"). In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 20 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 20 carbon atoms, at least one triple bond, and 1 or more heteroatoms within the parent chain ("heteroC$_{2-20}$ alkynyl" or "C$_{2-20}$ heteralkynyl"). In certain embodiments, a heteroalkynyl group refers to a group having from 2 to 12 carbon atoms, at least one triple bond, and 1 or more heteroatoms within the parent chain ("heteroC$_{2-12}$ alkynyl"). In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl. In certain embodiments, the carbocyclyl is substituted or unsubstituted, 3- to 8-membered, and monocyclic. In certain embodiments, the carbocyclyl is substituted or unsubstituted, 5- to 14-membered, and bicyclic. In certain embodiments, the carbocyclyl is substituted or unsubstituted, 6- to 14-membered, and tricyclic.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 8-membered, monocyclic heterocyclyl, wherein 1, 2, or 3 atoms in the heterocyclic ring system are independently oxygen, nitrogen, or sulfur, as valency permits. In certain embodiments, the heterocyclyl is substituted or unsubstituted, 5- to 14-membered, bicyclic heterocyclyl, wherein 1, 2, 3, or 4 atoms in the heterocyclic ring system are independently oxygen, nitrogen, or sulfur, as valency permits. In certain embodiments, the heterocyclyl is substituted or unsubstituted, 6- to 14-membered, tricyclic heterocyclyl, wherein 1, 2, 3, or 4 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" or "fully saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

In certain embodiments, when one or more carbons atom of the substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl are substituted with one or more substituents, the substituents are "carbon atom substituents." In certain embodiments, each carbon atom substituent is, independently, selected from halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;
  or two geminal hydrogen atoms on a carbon atom are replaced with the group =O, =S, =NN(R$^{bb}$)$_2$, =NNR$^{bb}$C(=O)R$^{aa}$—, =NNR$^{bb}$C(=O)OR$^{aa}$, =NNR$^{bb}$S(=O)$_2$R$^{aa}$, =NR$^{bb}$, or =NOR$^{cc}$;
  each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;
  each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$alkyl, C$_{1-10}$ perhaloalkyl, C$_{2-10}$alkenyl, C$_{2-10}$alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;
  each instance of R$^{cc}$ is, independently, selected from hydrogen, C$_{1-10}$alkyl, C$_{1-10}$ perhaloalkyl, C$_{2-10}$ alkenyl, C$_{2-10}$alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;
  each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ee}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, and 5-10 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ groups are joined to form =O or =S;
  each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;
  each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, and 5-10 membered heteroaryl, or two R$^{ff}$ groups are joined to form a 3-10 membered heterocyclyl or 5-10 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;
  each instance of R$^{gg}$ is, independently, selected from halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, and 5-10 membered heteroaryl; or two geminal R$^{gg}$ groups are joined to form O or =S; and
  X$^-$ is a counterion.

In certain embodiments, the carbon atom substituents are independently halogen, substituted (e.g., substituted with one or more halogen) or unsubstituted C$_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R$^{aa}$, or —NR$^{bb}$C(=O)N(R$^{bb}$)$_2$. In certain embodiments, the carbon atom substituents are independently halogen, substituted (e.g., substituted with one or more halogen) or unsubstituted C$_{1-6}$ alkyl, —OR$^{aa}$, —SR$^{aa}$, —N($R^{bb}$)$_2$, —CN, —SCN, —NO$_2$, —C(=O)$R^{aa}$, —CO$_2$$R^{aa}$, —C(=O)N($R^{bb}$)$_2$, —OC(=O)$R^{aa}$, —OCO$_2$$R^{aa}$, —OC(=O)N($R^{bb}$)$_2$, —N$R^{bb}$C(=O)$R^{aa}$, —N$R^{bb}$CO$_2$$R^{aa}$, or —N$R^{bb}$C(=O)N($R^{bb}$)$_2$, wherein $R^{aa}$ is hydrogen, substituted (e.g., substituted with one or more halogen) or unsubstituted $C_{1-6}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group (e.g., Bn, Boc, Cbz, Fmoc, trifluoroacetyl, triphenylmethyl, acetyl, or Ts). In certain embodiments, the carbon atom substituents are independently halogen, substituted (e.g., substituted with one or more halogen) or unsubstituted $C_{1-6}$ alkyl, —O$R^{aa}$, S$R^{aa}$, —N($R^{bb}$)$_2$, —CN, —SCN, or —NO$_2$. In certain embodiments, the carbon atom substituents are independently halogen, substituted (e.g., substituted with one or more halogen moieties) or unsubstituted $C_{1-6}$ alkyl, —O$R^{aa}$, —S$R^{aa}$, —N($R^{bb}$)$_2$, —CN, —SCN, or —NO$_2$, wherein $R^{aa}$ is hydrogen, substituted (e.g., substituted with one or more halogen) or unsubstituted $C_{1-6}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group (e.g., Bn, Boc, Cbz, Fmoc, trifluoroacetyl, triphenylmethyl, acetyl, or Ts).

In certain embodiments, the molecular weight of a carbon atom substituent is lower than 250, lower than 200, lower than 150, lower than 100, or lower than 50 g/mol. In certain embodiments, a carbon atom substituent consists of carbon, hydrogen, fluorine, chlorine, bromine, iodine, oxygen, sulfur, nitrogen, and/or silicon atoms. In certain embodiments, a carbon atom substituent consists of carbon, hydrogen, fluorine, chlorine, bromine, iodine, oxygen, sulfur, and/or nitrogen atoms. In certain embodiments, a carbon atom substituent consists of carbon, hydrogen, fluorine, chlorine, bromine, and/or iodine atoms. In certain embodiments, a carbon atom substituent consists of carbon, hydrogen, fluorine, and/or chlorine atoms.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O)S$R^{aa}$, —OC(=O)$R^{aa}$, —OCO$_2$$R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N($R^{bb}$)$_2$, —OS(=O)$R^{aa}$, —OSO$_2$$R^{aa}$, —OSi($R^{aa}$)$_3$, —OP($R^{cc}$)$_2$, —OP($R^{aa}$)$_3$, —OP(=O)$_2$$R^{aa}$, —OP(=O)($R^{aa}$)$_2$, —OP(=O)(O$R^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —S$R^{aa}$, —S=S$R^{aa}$, —SC(=S)S$R^{aa}$, —SC(=O)S$R^{aa}$, —SC(=O)O$R^{aa}$, and —SC(=O)$R^{aa}$, wherein $R^{aa}$ and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2$$R^{aa}$, —NHC(=O)N($R^{bb}$)$_2$, —NHC(=N$R^{bb}$)N($R^{bb}$)$_2$, —NHSO$_2$$R^{aa}$, —NHP(=O)(O$R^{cc}$)$_2$, and —NHP(=O)(N$R^{bb}$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2$$R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2$$R^{aa}$, —N$R^{bb}$P(=O)(O$R^{cc}$)$_2$, and —N$R^{bb}$P(=O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$X$^-$, wherein $R^{bb}$ and X are as defined herein.

The term "sulfonyl" refers to a group selected from —SO$_2$N($R^{bb}$)$_2$, —SO$_2$$R^{aa}$, and —SO$_2$O$R^{aa}$, wherein $R^{aa}$ and $R^{bb}$ are as defined herein.

The term "sulfinyl" refers to the group —S(=O)$R^{aa}$, wherein $R^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—CO$_2$H), aldehydes (—CHO), esters (—CO$_2$$R^{aa}$, —C(=O)S$R^{aa}$, —C(=S)S$R^{aa}$), amides (—C(=O)N($R^{bb}$)$_2$, —C(=O)N$R^{bb}$SO$_2$$R^{aa}$, —C(=S)N($R^{bb}$)$_2$), and imines (—C(=N$R^{bb}$)$R^{aa}$, —C(=N$R^{bb}$)O$R^{aa}$, —C(=N$R^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "boronyl" refers to boranes, boronic acids, boronic esters, borinic acids, and borinic esters, e.g., boronyl groups of the formula —B($R^{aa}$)$_2$, —B(O$R^{cc}$)$_2$, and —B$R^{aa}$(O$R^{cc}$), wherein $R^{aa}$ and $R^{cc}$ are as defined herein.

The term "phosphino" refers to the group —P($R^{cc}$)$_3$, wherein $R^{cc}$ is as defined herein. An exemplary phosphino group is triphenylphosphine.

The term "phosphono" refers to the group —O(P=O)(O$R^{cc}$)$R^{aa}$, wherein $R^{aa}$ and $R^{cc}$ are as defined herein.

The term "phosphoramido" refers to the group —O(P=O)(N$R^{bb}$)$_2$, wherein each $R^{bb}$ is as defined herein.

The term "stannyl" refers to the group —Sn($R^{cc}$)$_3$, wherein $R^{cc}$ is as defined herein.

The term "germyl" refers to the group —Ge($R^{cc}$)$_3$, wherein $R^{cc}$ is as defined herein.

The term "arsenyl" refers to the group —As($R^{cc}$)$_3$, wherein $R^{cc}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. In certain embodiments, when one or more nitrogen atoms of the substituted or unsubstituted heterocyclyl or substituted or unsubstituted heteroaryl are substituted with one or more substituents, the substituents are "nitrogen atom substituents." In certain embodiments, each nitrogen atom substituent is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SRC, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$alkyl, C$_{1-10}$ perhaloalkyl, C$_{2-10}$alkenyl, C$_{2-10}$alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein.

In certain embodiments, the nitrogen atom substituents are independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or a nitrogen protecting group. In certain embodiments, the nitrogen atom substituents are independently substituted (e.g., substituted with one or more halogen) or unsubstituted C$_{1-6}$ alkyl, —C(=O)R$^{aa}$, —CO$_2$R$^{aa}$, —C(=O)N(R$^{bb}$)$_2$, or a nitrogen protecting group, wherein R$^{aa}$ is hydrogen, substituted (e.g., substituted with one or more halogen) or unsubstituted C$_{1-6}$ alkyl, or an oxygen protecting group when attached to an oxygen atom; and each R$^{bb}$ is independently hydrogen, substituted (e.g., substituted with one or more halogen) or unsubstituted C$_{1-6}$ alkyl, or a nitrogen protecting group. In certain embodiments, the nitrogen atom substituents are independently substituted (e.g., substituted with one or more halogen) or unsubstituted C$_{1-6}$ alkyl or a nitrogen protecting group.

In certain embodiments, the substituent present on the nitrogen atom is a nitrogen protecting group (also referred to herein as an "amino protecting group"). Nitrogen protecting groups include —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{2-10}$alkenyl, C$_{2-10}$alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts.

In certain embodiments, the oxygen atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or an oxygen protecting group. In certain embodiments, the oxygen atom substituents are independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, or an oxygen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$) $R^{aa}$, —C(=N$R^{bb}$)O$R^{aa}$, —C(=N$R^{bb}$)N($R^{bb}$)$_2$, —S(=O) $R^{aa}$, —SO$_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxyethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, each of the sulfur atom substituents is independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, a sulfur protecting group, or =O. In certain embodiments, each of the sulfur atom substituents is independently substituted (e.g., substituted with one or more halogen) or unsubstituted $C_{1-6}$ alkyl, —C(=O)$R^{aa}$, —CO$_2R^{aa}$, —C(=O)N($R^{bb}$)$_2$, a sulfur protecting group, or =O, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, each of the sulfur atom substituents is independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). Sulfur protecting groups include —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)OR—, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3$, —P(=O)$_2R^{aa}$, —P(=O)($R^{aa}$)$_2$, —P(=O)(O$R^{cc}$)$_2$, —P(=O)$_2$N($R^{bb}$)$_2$, and —P(=O)(N$R^{bb}$)$_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

In certain embodiments, the oxygen and sulfur atoms of the substituted or unsubstituted heterocyclyl and substituted or unsubstituted heteroaryl are unsubstituted.

In certain embodiments, the molecular weight of a substituent is lower than 250, lower than 200, lower than 150, lower than 100, or lower than 50 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, iodine, oxygen, sulfur, and/or nitrogen atoms. In certain embodiments, a substituent consists of carbon, hydrogen, fluorine, chlorine, bromine, and/or iodine atoms. In certain embodiments, a substituent consists of carbon, hydrogen, fluorine, and/or chlorine atoms. In certain embodiments, a substituent comprises 0, 1, 2, or 3 hydrogen bond donors. In certain embodiments, a substituent comprises 0, 1, 2, or 3 hydrogen bond acceptors.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

The term "amorphous" or "amorphous form" refers to a form of a solid ("solid form"), the form substantially lacking three-dimensional order. In certain embodiments, an amorphous form of a solid is a solid form that is substantially not crystalline. In certain embodiments, the X-ray powder diffraction (XRPD) pattern of an amorphous form includes a wide scattering band with a peak at 2θ of, e.g., between 20 and 70°, inclusive, using CuKα radiation. In certain embodiments, the XRPD pattern of an amorphous form further includes one or more peaks attributed to crystalline structures. In certain embodiments, the maximum intensity of any one of the one or more peaks attributed to crystalline structures observed at a 2θ of between 20 and 70°, inclusive, is not more than 300-fold, not more than 100-fold, not more than 30-fold, not more than 10-fold, or not more than 3-fold of the maximum intensity of the wide scattering band. In certain embodiments, the XRPD pattern of an amorphous form includes no peaks attributed to crystalline structures.

The term "co-crystal" refers to a crystalline structure comprising at least two different components (e.g., a compound disclosed herein and an acid), wherein each of the components is independently an atom, ion, or molecule. In certain embodiments, none of the components is a solvent. In certain embodiments, at least one of the components is a solvent. A co-crystal of a compound disclosed herein and an acid is different from a salt formed from a compound disclosed herein and the acid. In the salt, a compound disclosed herein is complexed with the acid in a way that proton transfer (e.g., a complete proton transfer) from the acid to a compound disclosed herein easily occurs at room temperature. In the co-crystal, however, a compound disclosed herein is complexed with the acid in a way that proton transfer from the acid to a compound disclosed herein does not easily occur at room temperature. In certain embodiments, in the co-crystal, there is no proton transfer from the acid to a compound disclosed herein. In certain embodiments, in the co-crystal, there is partial proton transfer from the acid to a compound disclosed herein. Co-crystals may be useful to improve the properties (e.g., solubility, stability, and ease of formulation) of a compound disclosed herein.

The term "isotopically labeled compound" refers to a derivative of a compound that only structurally differs from the compound in that at least one atom of the derivative includes at least one isotope enriched above (e.g., enriched 3-, 10-, 30-, 100-, 300-, 1,000-, 3,000- or 10,000-fold above) its natural abundance, whereas each atom of the compound includes isotopes at their natural abundances.

The term "prodrugs" refers to compounds that have cleavable groups and become by solvolysis or under physiological conditions the compounds described herein, which are pharmaceutically active in vivo. Such examples include choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_6$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence. The treatment may be therapeutic treatment (not including prevention or prophylactic treatment).

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "inhibition", "inhibiting", "inhibit," "inhibitory," or "inhibitor" refers to the ability of a compound to reduce, slow, halt, or prevent activity of a particular biological process (e.g., the growth or reproduction) of a microorganism (e.g., a bacterium, mycobacterium, archaeon, protist, fungus, or parasite) relative to vehicle.

The term "minimum inhibitory concentration" or "MIC" refers to the lowest concentration of a compound that will inhibit the visible growth of a microorganism (e.g., a bacterium, mycobacterium, archaeon, protist, fungus, or parasite) after overnight (e.g., about 16 to about 20 hours, or about 16 to about 18 hours) incubation of the microorganism with the compound at about 37° C.

The term "half maximal inhibitory concentration" or "$IC_{50}$" of a compound refers to the concentration of the compound that inhibits the growth of half of an inoculum of a microorganism (e.g., a bacterium, mycobacterium, archaeon, protist, fungus, or parasite).

The term "microorganism" refers to a microscopic organism, which may be a single-cell or multicellular organism. In certain embodiments, the microorganism is a bacterium, mycobacterium, archaeon, protist (e.g., protozoon, alga), fungus (e.g., yeast, mold), or parasite. In certain embodiments, the microorganism is a bacterium. In certain embodiments, the length or diameter of a microorganism is at most about 10 cm, at most about 1 cm, at most about 1 mm, at most about 100 μm, at most about 10 μm, at most about 1 μm, at most about 100 nm, or at most about 10 nm. In certain embodiments, the length or diameter of a microorganism is at most about 10 μm.

The term "biofilm" refers to a group of microorganisms (e.g., bacteria) in which cells of the microorganisms stick to each other on a surface. These adherent cells are frequently embedded within a self-produced matrix of extracellular polymeric substance (EPS). The EPS is a polymeric conglomeration generally composed of extracellular DNA, proteins, and polysaccharides. Biofilms may form on living or non-living surfaces and can be prevalent in natural, industrial, and hospital settings. The cells growing in a biofilm are physiologically distinct from planktonic cells of the same microorganism, which are single-cells that may float or swim in a liquid medium. Biofilms have been found to be involved in a wide variety of microbial infections. Biofilms are formed by numerous Gram-negative and Gram-positive bacterial species. Non-limiting examples include *Bacillus* spp, *Staphylococcus* spp, *Pseudomonas* spp, and *Acinetobacter* spp.

The term "microbial warfare" refers to a first microorganism producing a substance (e.g., an antibiotic) that is toxic to a second microorganism but is not toxic or less toxic, compared to the second microorganism, to the first microorganism. When a second microorganism in close proximity to the first microorganism contacts the substance, the growth and/or reproduction of the second microorganism may be inhibited, or the second microorganism may be killed. As a result, the first microorganism may gain a competitive advantage over the second microorganism in close proximity to the first microorganism in terms of survival, growth, and/or reproduction.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

The term "planktonic" refers to any of the group of passively floating, drifting, or somewhat motile organisms occurring in a liquid medium (e.g., an aqueous solution). This group includes, but is not limited to, microscopic bacteria, algae, or protozoa.

BRIEF DESCRIPTION OF THE DRAWINGS

The accompanying drawings, which constitute a part of this specification, illustrate several embodiments of the invention and together with the description, serve to explain the principles of the invention.

Figure 7A:
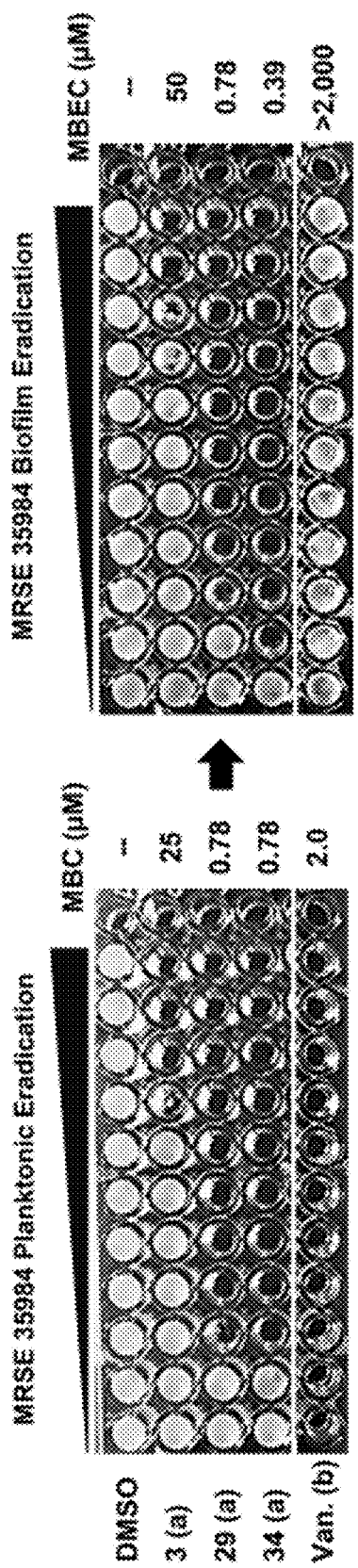
FIGS. 7A to 7B show MRSE 35984 biofilm eradication results with HPs 29 and 34 from CBD assays. Turbidity results to determine planktonic and biofilm eradication (MBC/MBEC values) (FIG. 7A), and biofilm killing from viable cell counts on CBD pegs (FIG. 7B). Test range.
Figure 7B:
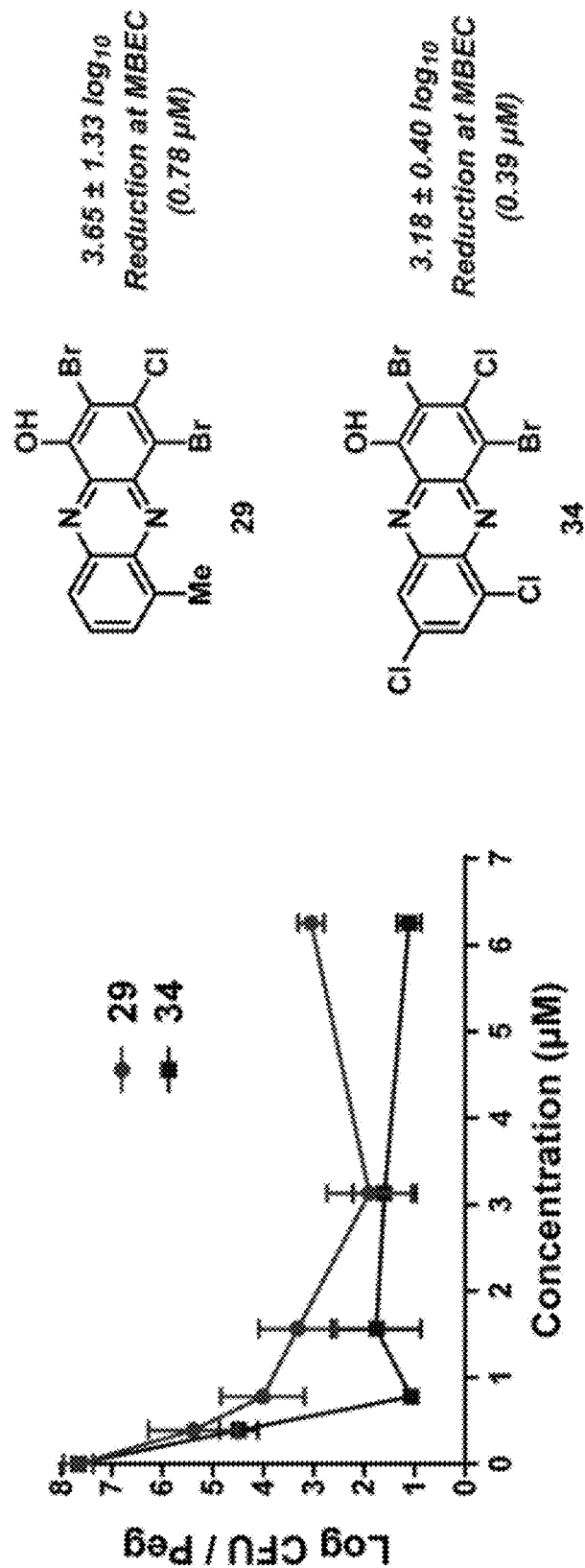

0.2-200 μM (FIG. 7A), 2-2000 μM (2-fold dilutions) (FIG. 7B). Van. denotes Vancomycin.

Figure 8A:
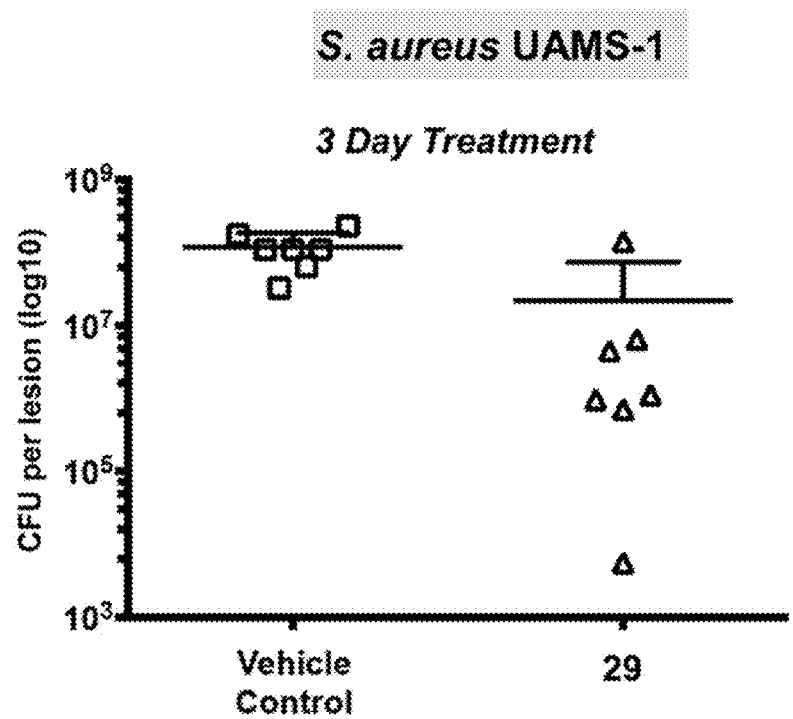
Figure 8B:
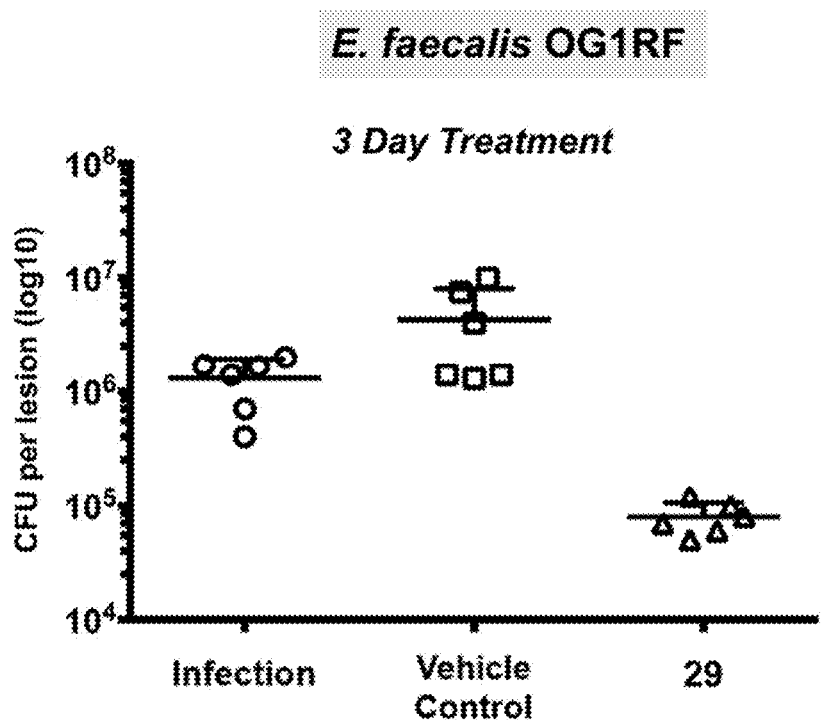

FIGS. 8A to 8B show an in vivo assessment of HP 29 in dorsal wound infections of S. aureus and E. faecalis in mice. FIG. 8A shows HP 29 reduced S. aureus UAMS-1 bacterial load in BALB/c mice (Student's T-test: p value=0.010; 7 mice per group). FIG. 8B shows HP 29 reduced E. faecalis OG1RF bacterial load in C57BL/6J mice (comparing mice treated with 29 and infection control; ANOVA: day 3, p value=0.068).

Figure 9:
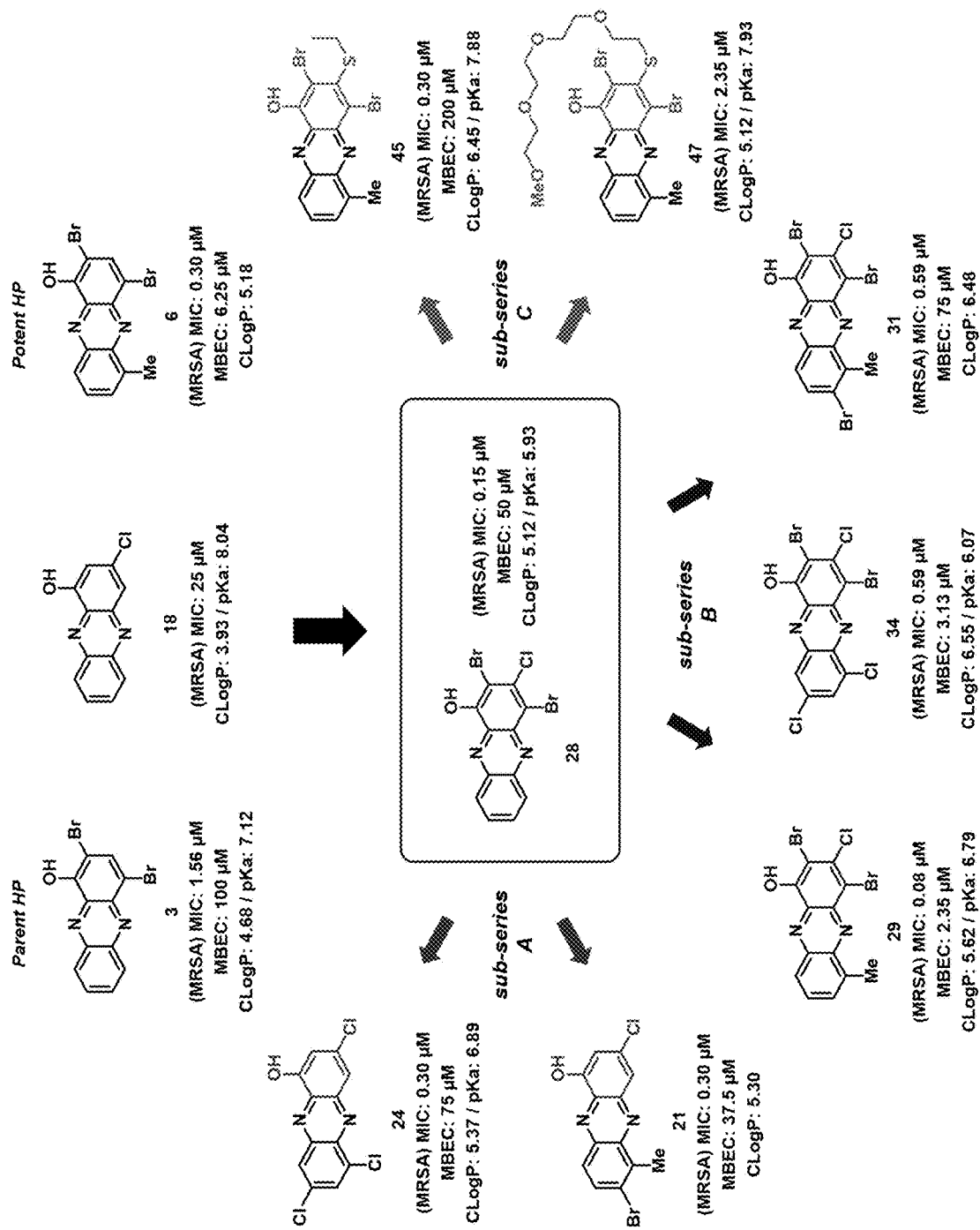

FIG. 9 shows structure-activity relationship profiles for HP analogues functionalized at the 3-position of the HP scaffold. MRSA data refers to MRSA-1707 findings in this SAR figure.

Figure 10:
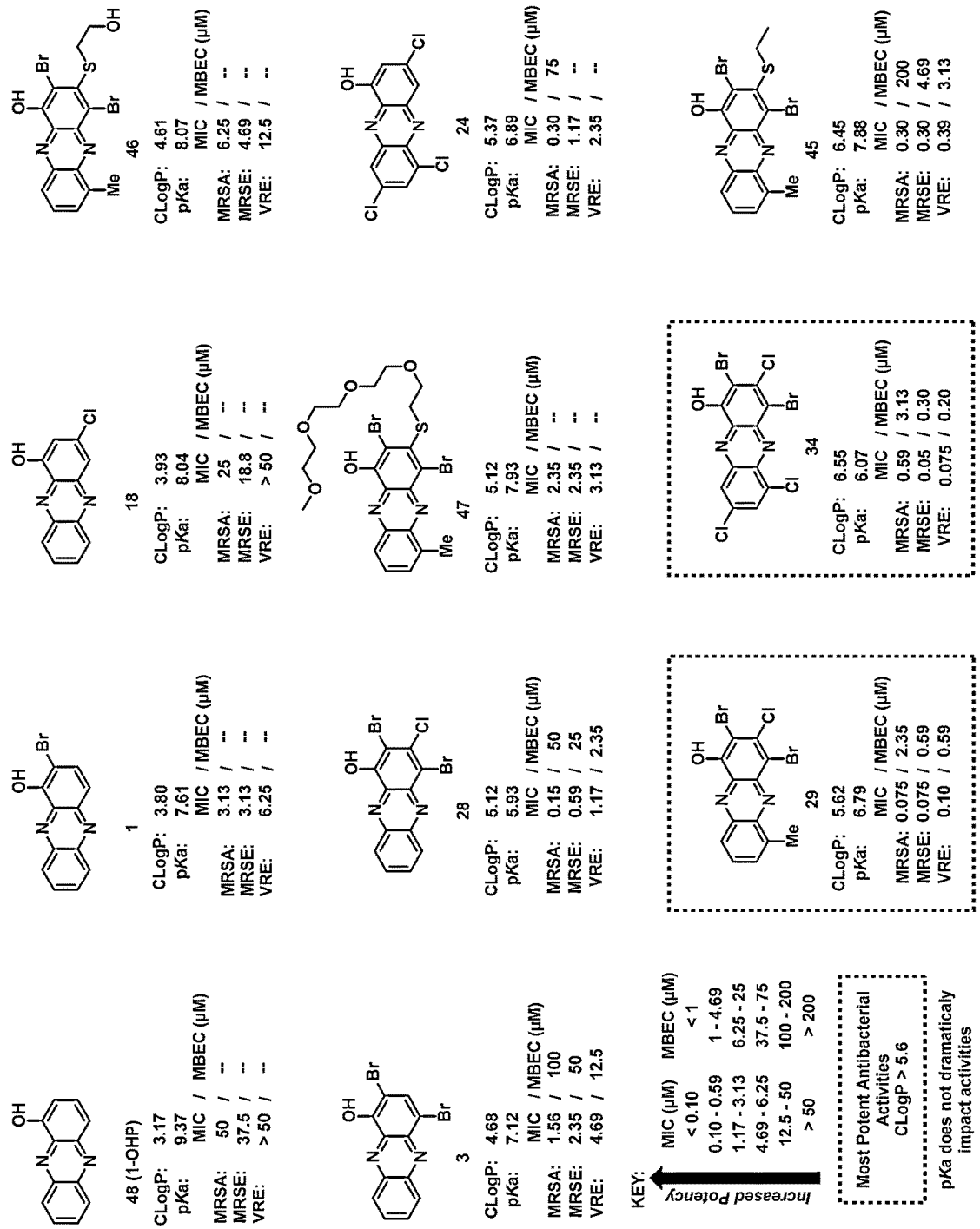

FIG. 10 shows activity profiles with $pK_a$ and C Log P values for select HP analogues.

DETAILED DESCRIPTION OF CERTAIN EMBODIMENTS OF THE INVENTION

Other antimicrobial phenazine derivatives have been reported in U.S. Patent Application Publication Nos. US 2016-0355487, US 2018-0312473, US 2018-0265475, and US 2020-0010432, each of which is incorporated herein by reference. The present invention provides, in one aspect, phenazine derivatives, such as compounds of Formulae (I), and salts (e.g., pharmaceutically acceptable salts), solvates, hydrates, polymorphs, co-crystals, tautomers, stereoisomers, isotopically labeled compounds, and prodrugs thereof. The compounds of the invention are expected to be antimicrobial agents and, without wishing to be bound by any particular theory, may act by a microbial warfare strategy (e.g., a reactive oxygen species (ROS)-based competition strategy). The present invention also provides compositions including pharmaceutical compositions, kits, uses, and methods that involve the compounds of the invention and may be useful in preventing and/or treating a microbial infection in a subject, inhibiting the growth and/or reproduction of a microorganism (e.g., bacterium, mycobacterium, archaeon, protist, fungus, or parasite), killing a microorganism, inhibiting the formation and/or growth of a biofilm, reducing or removing a biofilm, or disinfecting a surface. In certain embodiments, the microorganism is a bacterium. In certain embodiments, the bacterium is a Gram-positive bacterium (e.g., a species of Staphylococcus or Enterococcus). In certain embodiments, the bacterium is a Gram-negative bacterium (e.g., an Acinetobacter species).

Many past successes in antibiotic discovery have been grounded on microbial warfare agents/strategies from microorganisms. Therefore, future antimicrobial treatments may also depend on the discovery and implementation of innovative microbial-inspired antimicrobial strategies. One such strategy is the use of redox-active phenazine antibiotics by Pseudomonas during competition with other bacteria and fungi through the formation of reactive oxygen species (ROS) (A. Price-Whelan, L. E. P. Dietrich, and D. K. Newman, Nat. Chem. Biol., 2006, 2, 71-78; Z. A. Machan, T. L. Pitt, W. White, D. Watson, G. W. Taylor, P. J. Cole, and R. Wilson, J. Med. Microbiol., 1991, 34, 213-217). One example of this competition is in young cystic fibrosis (CF) patients (Z. A. Machan, T. L. Pitt, W. White, D. Watson, G. W. Taylor, P. J. Cole, and R. Wilson, J. Med. Microbiol., 1991, 34, 213-217). Many times, individuals with CF first develop Staphylococcus aureus lung infections when they are young. As the CF patient ages, Pseudomonas aeruginosa co-infects the lung and successfully competes against S. aureus for this niche using redox-active phenazine antibiotics.

Certain phenazine derivatives, such as compounds 301-305 (shown below) are known antimicrobial agents. Pyocyanin (compound 301) is one of the toxins produced by the Gram negative bacterium Pseudomonas aeruginosa. It is thought that Pseudomonas aeruginosa employs a microbial warfare strategy by producing these toxins in competing with other microorganisms (e.g., other bacteria). Pyocyanin is able to oxidize and reduce other molecules (Hassan et al., J. Bacteriology 1980, 141, 156-163) and can kill microbes competing against Pseudomonas aeruginosa as well as mammalian cells of the lungs that Pseudomonas aeruginosa has infected during cystic fibrosis. Due to its redox-active properties, pyocyanin can generate reactive oxygen species (ROS), which may be toxic to bacteria. It has been reported that the reduction potential and redox-cycling capabilities of phenazine are electronically influenced by functional group substitutions on the phenazinyl ring system (Price-Whelan et al., Nat. Chem. Biol., 2006, 2, 71-78; Wang et al., J. Bacteriol., 2010, 192, 365-369). Therefore, the redox-active properties of a phenazine derivative may be altered by structurally modifying the phenazine derivative. However, there is no teaching or suggestion in the art on how a known phenazine may be structurally modified to improve its properties, such as antimicrobial activity.

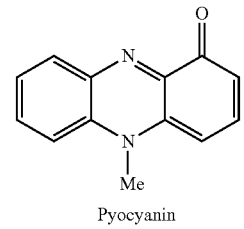

Pyocyanin

301

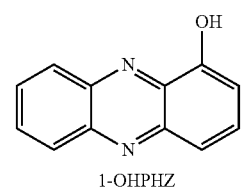

1-OHPHZ

302

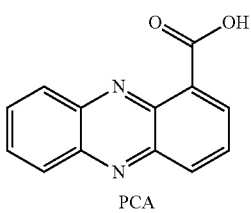

PCA

303

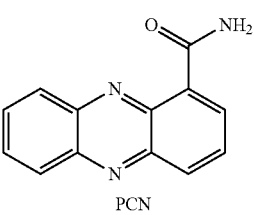

PCN

304

-continued

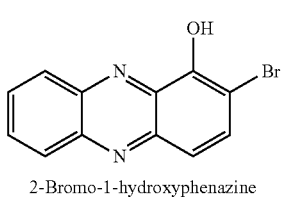

2-Bromo-1-hydroxyphenazine

Pathogenic bacteria demonstrate incredible abilities to overcome and evade conventional antibiotic therapies through the rapid development of resistance and the formation of metabolically dormant, surface-attached biofilm communities. Therefore, synthetically tunable small molecules that can effectively target and eradicate both planktonic and biofilm bacteria through new modes of action are of significant clinical interest. Here, we continue our efforts to explore diverse HP small molecules through the use of N-aryl-2-nitrosoaniline intermediates that provide functionalization of the 3-position of this antibacterial scaffold. During these investigations, we synthesized a diverse series of >20 HP analogues that demonstrate potent in vitro antibacterial and biofilm eradication activities against multiple Gram-positive pathogens (e.g., HP 29, against methicillin-resistant Staphylococcus aureus BAA-1707: minimum inhibitory concentration=0.075 µM; minimum biofilm eradication concentration=2.35 µM). Transcriptional analysis revealed that HPs 3, 28, and 29 induced rapid iron starvation in MRSA BAA-1707 biofilms. In addition, several HPs demonstrated good to excellent activities against the slow-growing pathogen Mycobacterium tuberculosis with HP 34 reporting an MIC of 0.80 µM against strain CDC1551. This collection of HPs provided new SAR insights and HP 29 demonstrated in vivo efficacy against S. aureus and Enterococcus faecalis in dorsal wound models in mice. In conclusion, HPs could lead to critical advances in the treatment of significant infections, including wounds and chronic biofilm-associated infections.

Figure 1:
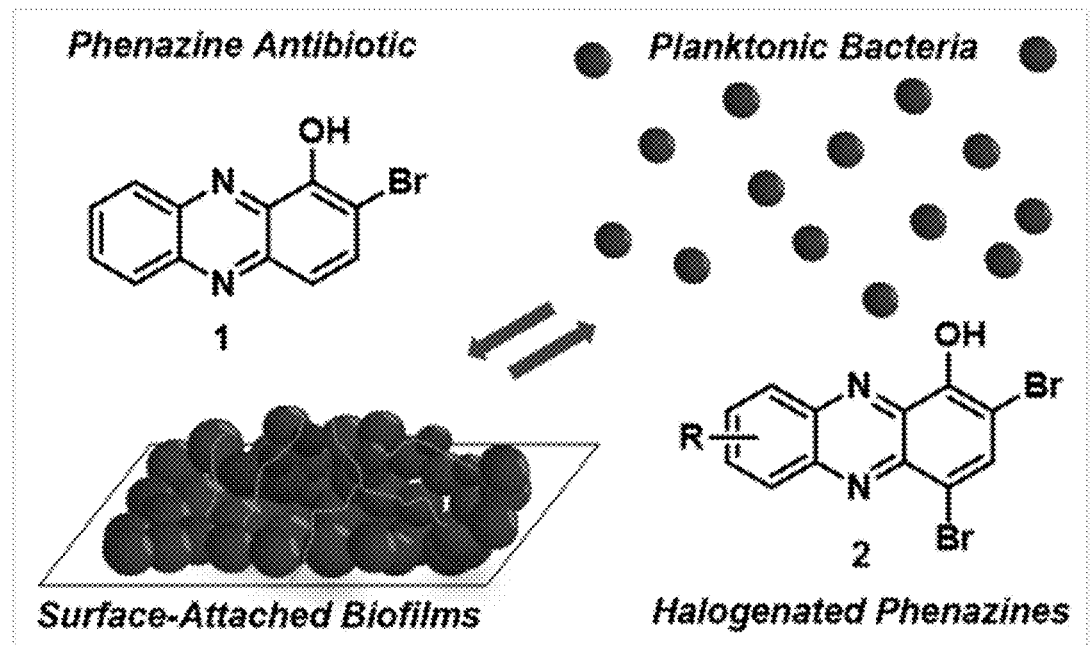
FIG. 1 shows that marine phenazine 2-bromo-1-hydroxyphenazine (1) demonstrates antibacterial activities and shows synthetic analogues (2).
Figure 2:
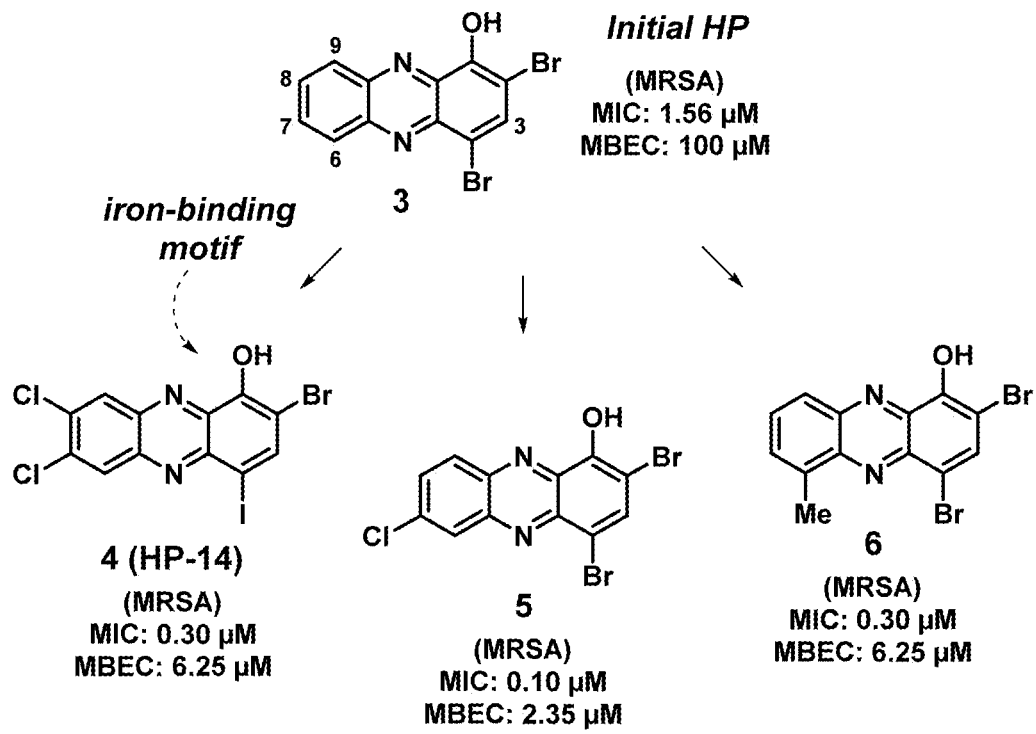
FIG. 2 shows select halogenated phenazine analogues that demonstrate antibacterial and biofilm eradication activities.

Some of our previous studies have focused on the (1) synthesis of diverse HPs to explore structure-activity relationships (SAR, see HPs 3-6; FIG. 2),[36-38] and (2) understanding HP-14's mode of action by transcript profiling using RNA-seq technology.[39] Through the synthesis and microbiological testing of >100 HP analogues, we have shown several substituents in the 6, 7, and 8 positions of the HP scaffold significantly improve antibacterial/biofilm eradication potency. Transcript profiling of established MRSA BAA-1707 biofilms demonstrated that HP-14 rapidly induces the transcription of several gene clusters involved in iron-acquisition (isd, iron-regulated surface determinant; sbn, staphyloferrin B, siderophore; sfa, staphyloferrin A, siderophore; MW0695, ferrichrome ABC transporter)[39], which aligned with our previous findings that HPs bind metal(II) cations, including iron(II).[36-38] Overall, we have identified a synthetically tunable series of HPs that demonstrates potent antibacterial activity against planktonic cells and eradicates biofilms through a rapid iron starvation mode of action.

Figure 3:
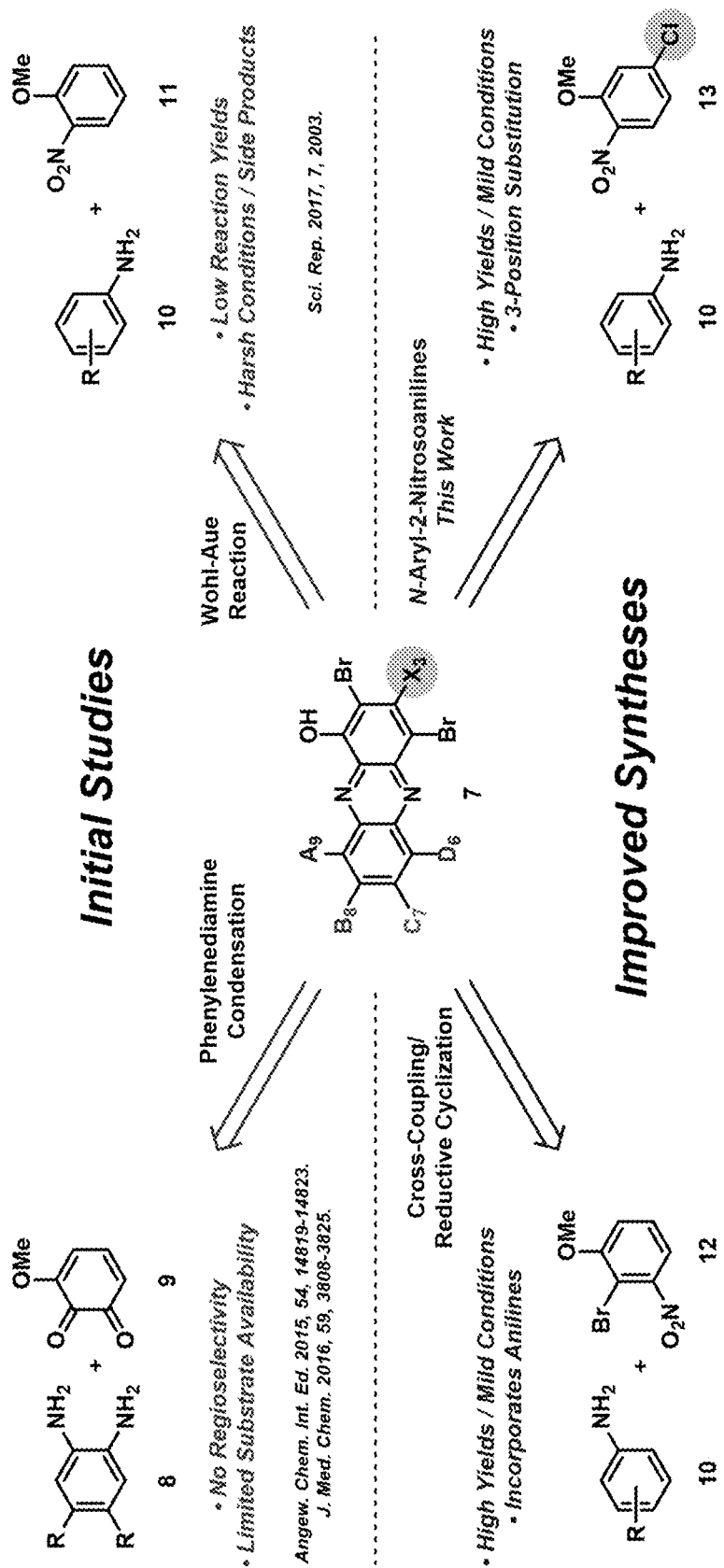
FIG. 3 shows an overview of synthesis strategies utilized to access new HPs for microbiological investigations.

Our efforts towards exploring the HP scaffold began with the condensation of 4,5-disubstutied o-phenylenediamines 8 and quinone 9 to yield 1-methoxyphenazines, which were then subjected to (1) boron tribromide ($BBr_3$) demethylation, and (2) N-bromosuccinimide (NBS) mediated bromination to final HPs 7 (FIG. 3).[3-36] In later work, we fused a series of diverse aniline building blocks 10 with 2-nitroanisole 11 through a Wohl-Aue reaction to access new 1-methoxyphenazine compounds, which were transformed to target HPs for biological investigation.[37] Most recently, we reported the use of 2-bromo-3-nitroanisole 12 in a modular Buchwald-Hartwig cross-coupling reaction with diverse anilines 10 followed by a reductive cyclization under basic conditions to generate new 1-methoxyphenazines that were advanced to new HPs.[38] Here, we report the utilization of N-aryl-2-nitrosoaniline intermediates to enable rapid access to HPs functionalized at the 3-position from anilines 10 and 2-nitro-5-chloroanisole 13 to further explore structure-activity relationships for this potent antibacterial scaffold.

In certain embodiments, the compounds of the invention are improved phenazine derivatives and showed unexpected and superior properties compared to known phenazine derivatives, such as enhanced inhibitory activity against bacteria, e.g., Staphylococcus aureus (S. aureus), Staphylococcus epidermidis (S. epidermidis), and/or Enterococcus faecium. Staphylococcus aureus is a human pathogen that is notorious for life-threatening drug-resistant infections in hospitals and the community (H. F. Chambers and F. R. DeLeo, Nat. Rev. Microbiol., 2009, 7, 629-641). In the United States alone, there are more annual deaths from methicillin-resistant Staphylococcus aureus (MRSA) related microbial infections than AIDS (IDSA Policy Paper d CID 2011:52 (Suppl 5) d S397). Staphylococcus epidermidis is also a pathogen of great importance as it is particularly prevalent in persistent microbial infections associated with catheters (I. Uckay, D. Pittet, P. Vaudaux, H. Sax, D. Lew, and F. Waldvogel, Ann. Med., 2009, 41, 109-119).

Without wishing to be bound by any particular theory, it is thought that the compounds of the invention may act by a microbial warfare strategy (e.g., an ROS-based competition strategy) similar to the one employed by Pseudomonas aeruginosa. The inventive compounds may be capable of undergoing reduction and oxidation (redox) reactions and forming ROS in, near, or around a microorganism (e.g., bacterium, mycobacterium, archaeon, protist, fungus, or parasite). An inventive compound may accept a single electron, yielding a relatively stable anion radical, and may readily undergo a redox cycle. A compound of the invention may be reduced by the nicotinamide adenine dinucleotide ($NADH^+$) in a microorganism and may divert electron flow within the microorganism from the normal cytochrome pathway to an ROS-producing pathway. As a result, the production of ROS, such as $O_2^-$ and $H_2O_2$, which are toxic to the microorganism, may be increased.

Furthermore, compounds disclosed herein may be effective agents for the inhibition of biofilm growth and/or clearance of existing biofilms. Bacterial biofilms are surface-attached bacterial communities that are encased within a secreted matrix of biomolecules (e.g., extracellular DNA, proteins, polysaccharides) known as the extracellular polymeric substance (EPS). Bacterial cells within a biofilm take on a completely different physiology than their free-swimming planktonic counterparts and are notorious for being highly resistant to conventional antibiotic treatments and host immune responses (Donlan, R. M. and Costerton, J. W. Clin. Microbiol. Rev. 2002, 15, 167-193). The National Institutes of Health has reported that biofilms are present in up to 80% of all bacterial infections. Unfortunately, biofilms are notorious for their resistance to conventional antibiotic treatments, and therefore our current arsenal of antibiotics does not include agents that effectively target biofilm machinery or clear established biofilms in a clinical setting. Such antibiofilm agents would lead to significant breakthroughs in how bacterial infections are treated and would result in the effective treatment of many life-threatening bacterial infections.

Bacterial biofilm formation is governed by a signaling process known as quorum sensing, which is used by bacteria to monitor population density and control bacterial virulence (Camilli, A. and Bassler, B. L. *Science* 2006, 311, 1113-1116; Ng, W.-L. and Bassler, B. L. *Annu. Rev. Genet.* 2009, 43, 197-222). Quorum sensing is used by free-swimming, individual planktonic bacteria to coordinate the simultaneous attachment and colonization of a surface followed by biofilm formation and maturation. The coordinated surface attachment of bacteria overwhelms immune responses mounted by host organisms, enabling the successful colonization of surfaces (e.g., tissue surfaces) by bacteria. Bacterial biofilms are known to be greater than 1000-fold more resistant to conventional antibiotics when compared to their planktonic counterparts. Therapeutic strategies targeting quorum sensing and/or biofilm formation and dispersion phenotypes have become a promising antibacterial strategy as small molecules capable of inhibiting bacterial biofilm formation via non-growth inhibitory mechanisms or clearing pre-formed bacterial biofilms are of clinical importance. Without wishing to be bound by any particular theory, compounds described herein may function by disrupting quorum sensing, leading to inhibitors of biofilm formation and clearing of pre-formed biofilms.

The inventive compounds preferably have minimal to no adverse side effects. In certain embodiments, the compounds exhibit low cytotoxicity against mammalian (e.g., human) cells. In certain embodiments, the compounds show low hemolysis activity.

Compounds

One aspect of the invention relates to compounds that are believed to be antimicrobial agents. In certain embodiments, the compounds of the invention are compound of Formula (I):

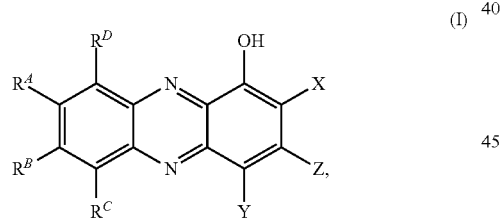

and salts (e.g., pharmaceutically acceptable salts), solvates, hydrates, polymorphs, co-crystals, tautomers, stereoisomers, isotopically labeled compounds, and prodrugs thereof, wherein:

X is hydrogen, halogen, substituted or unsubstituted alkyl, substituted or unsubstituted alkenyl, or substituted or unsubstituted alkynyl;

Z is halogen, substituted methyl, substituted or unsubstituted, $C_{2-12}$ alkyl, substituted or unsubstituted alkenyl, substituted or unsubstituted alkynyl, —$OR^3$, —$N(R^4)_2$, —$SR^5$, —SCN, —$C(=NR^5)R^5$, —$C(=NR^5)OR^5$, —$C(=NR^5)N(R^5)_2$, —C(=O)H, —$C(=O)N(R^5)_2$, —$NO_2$, —$NR^5C(=O)R^5$, —$NR^5C(=O)OR^5$, —$NR^5C(=O)N(R^5)_2$, —$OC(=O)R^5$, —$OC(=O)OR^5$, or —$OC(=O)N(R^5)_2$, wherein:

$R^3$ is substituted or unsubstituted acyl, substituted methyl, substituted or unsubstituted, $C_{2-12}$ alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of $R^4$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, or substituted or unsubstituted heteroaryl, or two instances of $R^4$ are joined to form a substituted or unsubstituted heterocyclic or substituted or unsubstituted heteroaryl ring; and each instance of $R^5$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^5$ are joined to form a substituted or unsubstituted heterocyclic or substituted or unsubstituted heteroaryl ring;

Y is hydrogen, halogen, substituted or unsubstituted alkyl, substituted or unsubstituted alkenyl, or substituted or unsubstituted alkynyl; and each of $R^A$, $R^B$, $R^C$, and $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^1$, —$N(R^1)_2$, —$SR^1$, —CN, —SCN, —$C(=NR^1)R^1$, —$C(=NR^1)OR^1$, —$C(=NR^1)N(R^1)_2$, —$C(=O)R^1$, —$C(=O)OR^1$, —$C(=O)N(R^1)_2$, —$NO_2$, —$NR^1C(=O)R^1$, —$NR^1C(=O)OR^1$, —$NR^1C(=O)N(R^1)_2$, —$OC(=O)R^1$, —$OC(=O)OR^1$, or —$OC(=O)N(R^1)_2$, wherein each instance of $R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^1$ are joined to form a substituted or unsubstituted heterocyclic or substituted or unsubstituted heteroaryl ring;

provided that the compound is not of the formula:

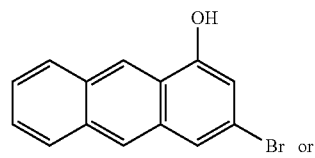

-continued

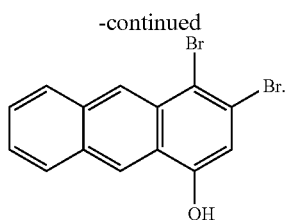

Formula (I) includes substituent X on the phenazinyl ring. In certain embodiments, X is hydrogen. In certain embodiments, X is halogen. In certain embodiments, X is F. In certain embodiments, X is Cl. In certain embodiments, X is Br. In certain embodiments, X is I. In certain embodiments, X is substituted or unsubstituted alkyl (e.g., substituted or unsubstituted $C_{1-6}$ alkyl). In certain embodiments, X is Me. In certain embodiments, X is substituted methyl (e.g., —$CH_2F$, —$CHF_2$, —$CF_3$, or Bn). In certain embodiments, X is Et, substituted ethyl (e.g., fluorinated ethyl (e.g., perfluoroethyl)), Pr, substituted propyl (e.g., fluorinated propyl (e.g., perfluoropropyl)), Bu, substituted butyl (e.g., fluorinated butyl (e.g., perfluorobutyl)), unsubstituted pentyl, substituted pentyl (e.g., fluorinated pentyl (e.g., perfluoropentyl)), unsubstituted hexyl, or substituted hexyl (e.g., fluorinated hexyl (e.g., perfluorohexyl)). In certain embodiments, X is substituted or unsubstituted alkenyl (e.g., substituted or unsubstituted $C_{2-6}$ alkenyl). In certain embodiments, X is substituted or unsubstituted vinyl. In certain embodiments, X is unsubstituted allyl. In certain embodiments, X is substituted allyl. In certain embodiments, X is substituted or unsubstituted alkynyl (e.g., substituted or unsubstituted $C_{2-6}$ alkynyl).

Formula (I) also includes substituent Y on the phenazinyl ring. In certain embodiments, Y is halogen. In certain embodiments, Y is F. In certain embodiments, Y is Cl. In certain embodiments, Y is Br. In certain embodiments, Y is I. In certain embodiments, Y is substituted or unsubstituted alkyl (e.g., substituted or unsubstituted $C_{1-6}$ alkyl). In certain embodiments, Y is Me. In certain embodiments, Y is substituted methyl (e.g., —$CH_2F$, —$CHF_2$, —$CF_3$, or Bn). In certain embodiments, Y is Et, substituted ethyl (e.g., fluorinated ethyl (e.g., perfluoroethyl)), Pr, substituted propyl (e.g., fluorinated propyl (e.g., perfluoropropyl)), Bu, substituted butyl (e.g., fluorinated butyl (e.g., perfluorobutyl)), unsubstituted pentyl, substituted pentyl (e.g., fluorinated pentyl (e.g., perfluoropentyl)), unsubstituted hexyl, or substituted hexyl (e.g., fluorinated hexyl (e.g., perfluorohexyl)). In certain embodiments, Y is n-Bu. In certain embodiments, Y is substituted or unsubstituted alkenyl (e.g., substituted or unsubstituted $C_{2-6}$ alkenyl). In certain embodiments, Y is substituted or unsubstituted vinyl. In certain embodiments, Y is unsubstituted allyl. In certain embodiments, Y is substituted allyl. In certain embodiments, Y is substituted or unsubstituted alkynyl (e.g., substituted or unsubstituted $C_{2-6}$ alkynyl).

In certain embodiments, X is hydrogen, and Y is halogen. In certain embodiments, X is halogen, and Y is hydrogen. In certain embodiments, X is hydrogen; and Y is F. In certain embodiments, X is hydrogen; and Y is Cl. In certain embodiments, X is hydrogen; and Y is Br. In certain embodiments, X is hydrogen; and Y is I. In certain embodiments, X is Cl; and Y is F. In certain embodiments, both X and Y are Cl. In certain embodiments, X is Cl; and Y is Br. In certain embodiments, X is Cl; and Y is I. In certain embodiments, X is Br; and Y is F. In certain embodiments, X is Br; and Y is Cl. In certain embodiments, each X and Y is Br. In certain embodiments, X is Br; and Y is I. In certain embodiments, X is I; and Y is F. In certain embodiments, X is I; and Y is Cl. In certain embodiments, X is I; and Y is Br. In certain embodiments, both X and Y are I. In certain embodiments, X is halogen; and Y is substituted or unsubstituted alkyl (e.g., substituted or unsubstituted $C_{1-6}$ alkyl). In certain embodiments, X is halogen; and Y is substituted or unsubstituted alkenyl (e.g., substituted or unsubstituted $C_{2-6}$ alkenyl). In certain embodiments, X is substituted or unsubstituted alkyl (e.g., substituted or unsubstituted $C_{1-6}$ alkyl); and Y is halogen. In certain embodiments, X is substituted or unsubstituted alkenyl (e.g., substituted or unsubstituted $C_{2-6}$ alkenyl); and Y is halogen. In certain embodiments, X is halogen; and X and Y are the same. In certain embodiments, X is halogen; and X and Y are not the same. In certain embodiments, at least one of X and Y is halogen. In certain embodiments, each X and Y is halogen.

In certain embodiments, Z is fluoro, chloro, iodo, substituted methyl, substituted or unsubstituted, $C_{2-12}$ alkyl, substituted or unsubstituted alkenyl, substituted or unsubstituted alkynyl, —$OR^3$, —$N(R^4)_2$, —$SR^5$, —SCN, —$C(=NR^5)R^5$, —$C(=NR^5)OR^5$, —$C(=NR^5)N(R^5)_2$, —$C(=O)H$, —$C(=O)N(R^5)_2$, —$NO_2$, —$NR^5C(=O)R^5$, —$NR^5C(=O)OR^5$, —$NR^5C(=O)N(R^5)_2$, —$OC(=O)R^5$, —$OC(=O)OR^5$, or —$OC(=O)N(R^5)_2$. In certain embodiments, Z is halogen. In certain embodiments, Z is fluoro, chloro, or iodo. In certain embodiments, Z is chloro. In certain embodiments, Z is bromo. In certain embodiments, Z is not bromo. In certain embodiments, Z is —$SR^5$. In certain embodiments, Z is —S(substituted or unsubstituted alkyl). In certain embodiments, Z is —S(unsubstituted $C_{1-6}$ alkyl) (e.g., —SMe, —SEt, —SPr). In certain embodiments, Z is —S(substituted $C_{1-6}$ alkyl) (e.g., —S—$(CH_2CH_2O)_{1-6}$—H, —S—$(CH_2CH_2O)_{1-6}$-Me). In certain embodiments, Z is —$OR^3$. In certain embodiments, Z is —$N(R^4)_2$.

In certain embodiments, $R^3$ is substituted methyl. In certain embodiments, $R^3$ is substituted or unsubstituted, $C_{2-12}$ alkyl. In certain embodiments, $R^3$ is substituted or unsubstituted acyl. In certain embodiments, $R^3$ is substituted or unsubstituted alkenyl (e.g., substituted or unsubstituted $C_{2-6}$ alkenyl) or substituted or unsubstituted alkynyl (e.g., substituted or unsubstituted $C_{2-6}$ alkynyl). In certain embodiments, $R^3$ is substituted or unsubstituted carbocyclyl (e.g., substituted or unsubstituted, 3- to 7-membed, monocyclic carbocyclyl comprising zero, one, or two double bonds in the carbocyclic ring system), substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur), substituted or unsubstituted aryl (e.g., substituted or unsubstituted phenyl), substituted or unsubstituted heteroaryl (e.g., substituted or unsubstituted, 5- to 6-membed, monocyclic heteroaryl, wherein one, two, three, or four atoms in the heteroaryl ring system are independently nitrogen, oxygen, or sulfur).

Formula (I) may include one or more instances of substituent $R^4$. When Formula (I) includes two or more instances of $R^4$, any two instances of $R^4$ may be the same or different from each other. In certain embodiments, at least one instance of $R^4$ is H. In certain embodiments, each instance of $R^4$ is H. In certain embodiments, at least one instance of $R^4$ is substituted or unsubstituted alkyl (e.g., substituted or unsubstituted $C_{1-6}$ alkyl (e.g., Me)). In certain embodiments, at least one instance of $R^4$ is substituted or unsubstituted acyl. In certain embodiments, at least one instance of $R^4$ is substituted or unsubstituted alkenyl (e.g., substituted or unsubstituted $C_{2-6}$ alkenyl) or substituted or unsubstituted alkynyl (e.g., substituted or unsubstituted $C_{2-6}$ alkynyl). In certain embodiments, at least one instance of $R^4$ is substituted or unsubstituted carbocyclyl (e.g., substituted or unsubstituted, 3- to 7-membed, monocyclic carbocyclyl comprising zero, one, or two double bonds in the carbocyclic ring system), substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur), or substituted or unsubstituted heteroaryl (e.g., substituted or unsubstituted, 5- to 6-membed, monocyclic heteroaryl, wherein one, two, three, or four atoms in the heteroaryl ring system are independently nitrogen, oxygen, or sulfur). In certain embodiments, two instances of $R^4$ are joined to form a substituted or unsubstituted heterocyclic or substituted or unsubstituted heteroaryl ring.

Formula (I) may include one or more instances of substituent $R^5$. When Formula (I) includes two or more instances of $R^5$, any two instances of $R^5$ may be the same or different from each other. In certain embodiments, at least one instance of $R^5$ is H. In certain embodiments, each instance of $R^5$ is H. In certain embodiments, at least one instance of $R^5$ is substituted or unsubstituted alkyl (e.g., substituted or unsubstituted $C_{1-6}$ alkyl (e.g., Me)). In certain embodiments, at least one instance of $R^5$ is substituted or unsubstituted acyl. In certain embodiments, at least one instance of $R^5$ is substituted or unsubstituted alkenyl (e.g., substituted or unsubstituted $C_{2-6}$ alkenyl) or substituted or unsubstituted alkynyl (e.g., substituted or unsubstituted $C_{2-6}$ alkynyl). In certain embodiments, at least one instance of $R^5$ is substituted or unsubstituted carbocyclyl (e.g., substituted or unsubstituted, 3- to 7-membed, monocyclic carbocyclyl comprising zero, one, or two double bonds in the carbocyclic ring system), substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur), substituted or unsubstituted aryl (e.g., substituted or unsubstituted phenyl), or substituted or unsubstituted heteroaryl (e.g., substituted or unsubstituted, 5- to 6-membed, monocyclic heteroaryl, wherein one, two, three, or four atoms in the heteroaryl ring system are independently nitrogen, oxygen, or sulfur). In certain embodiments, at least one instance of $R^5$ is a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^5$ are joined to form a substituted or unsubstituted heterocyclic or substituted or unsubstituted heteroaryl ring.

Formula (I) also includes substituent $R^A$ on the phenazinyl ring. In certain embodiments, $R^A$ is hydrogen. In certain embodiments, $R^A$ is not hydrogen. In certain embodiments, $R^A$ is halogen. In certain embodiments, $R^A$ is F. In certain embodiments, $R^A$ is Cl. In certain embodiments, $R^A$ is Br. In certain embodiments, $R^A$ is I. In certain embodiments, $R^A$ is halogen or substituted or unsubstituted alkyl. In certain embodiments, $R^A$ is halogen or unsubstituted $C_{1-6}$ alkyl. In certain embodiments, $R^A$ is substituted or unsubstituted alkyl. In certain embodiments, $R^A$ is substituted or unsubstituted $C_{1-6}$ alkyl. In certain embodiments, $R^A$ is Me. In certain embodiments, $R^A$ is substituted methyl (e.g., —CH$_2$F, —CHF$_2$, —CF$_3$, or Bn). In certain embodiments, $R^A$ is Et, substituted ethyl (e.g., fluorinated ethyl (e.g., perfluoroethyl)), Pr, substituted propyl (e.g., fluorinated propyl (e.g., perfluoropropyl)), Bu, or substituted butyl (e.g., fluorinated butyl (e.g., perfluorobutyl)). In certain embodiments, $R^A$ is substituted or unsubstituted alkenyl (e.g., substituted or unsubstituted $C_2$-6 alkenyl). In certain embodiments, $R^A$ is substituted or unsubstituted alkynyl (e.g., substituted or unsubstituted $C_{2-6}$ alkynyl). In certain embodiments, $R^A$ is substituted or unsubstituted carbocyclyl (e.g., substituted or unsubstituted, 3- to 7-membed, monocyclic carbocyclyl comprising zero, one, or two double bonds in the carbocyclic ring system). In certain embodiments, $R^A$ is substituted or unsubstituted cyclopropyl, substituted or unsubstituted cyclobutyl, substituted or unsubstituted cyclopentyl, or substituted or unsubstituted cyclohexyl. In certain embodiments, $R^A$ is substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^A$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^A$ is substituted or unsubstituted aryl (e.g., substituted or unsubstituted, 6- to 10-membered aryl). In certain embodiments, $R^A$ is unsubstituted phenyl. In certain embodiments, $R^A$ is substituted phenyl. In certain embodiments, $R^A$ is substituted or unsubstituted naphthyl. In certain embodiments, $R^A$ is substituted or unsubstituted heteroaryl. In certain embodiments, $R^A$ is substituted or unsubstituted, 5- to 6-membed, monocyclic heteroaryl, wherein one, two, three, or four atoms in the heteroaryl ring system are independently nitrogen, oxygen, or sulfur. In certain embodiments, $R^A$ is substituted or unsubstituted, 9- to 10-membed, bicyclic heteroaryl, wherein one, two, three, or four atoms in the heteroaryl ring system are independently nitrogen, oxygen, or sulfur. In certain embodiments, $R^A$ is —OR$^1$ (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, $R^A$ is —OMe. In certain embodiments, $R^A$ is —SR$^1$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^A$ is —N(R$^1$)$_2$ (e.g., —NH$_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, $R^A$ is —CN or —SCN. In certain embodiments, $R^A$ is —NO$_2$. In certain embodiments, $R^A$ is —C(=NR$^1$)R$^1$, —C(=NR$^1$)OR$^1$, or —C(=NR$^1$)N(R$^1$)$_2$. In certain embodiments, $R^A$ is —C(=O)R$^1$ (e.g., —C(=O)(substituted or unsubstituted alkyl) (e.g., —C(=O)Me) or —C(=O)(substituted or unsubstituted phenyl)). In certain embodiments, $R^A$ is —C(=O)OR$^1$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^A$ is —C(=O)N($R^1$)$_2$ (e.g., —C(=O)NH$_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^A$ is —NR$^1$C(=O)R$^1$ (e.g., —NHC(=O)(substituted or unsubstituted C$_{1-6}$ alkyl) (e.g., —NHC(=O)Me) or —NHC(=O)(substituted or unsubstituted phenyl)). In certain embodiments, $R^A$ is —NR$^1$C(=O)OR$^1$. In certain embodiments, $R^A$ is —NR$^1$C(=O)N(R$^1$)$_2$ (e.g., —NHC(=O)NH$_2$, —NHC(=O)NH(substituted or unsubstituted C$_{1-6}$ alkyl) (e.g., —NHC(=O)NHMe)). In certain embodiments, $R^A$ is —OC(=O)R$^1$ (e.g., —OC(=O)(substituted or unsubstituted alkyl) or —OC(=O)(substituted or unsubstituted phenyl)), —OC(=O)OR$^1$ (e.g., —OC(=O)O(substituted or unsubstituted alkyl) or —OC(=O)O(substituted or unsubstituted phenyl)), or —OC(=O)N(R$^1$)$_2$ (e.g., —OC(=O)NH$_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

Formula (I) may include one or more instances of substituent $R^1$. When Formula (I) includes two or more instances of $R^1$, any two instances of $R^1$ may be the same or different from each other. In certain embodiments, at least one instance of $R^1$ is H. In certain embodiments, each instance of $R^1$ is H. In certain embodiments, at least one instance of $R^1$ is substituted or unsubstituted alkyl (e.g., substituted or unsubstituted C$_{1-6}$ alkyl (e.g., Me)). In certain embodiments, at least one instance of $R^1$ is substituted or unsubstituted acyl, substituted or unsubstituted alkenyl (e.g., substituted or unsubstituted C$_{2-6}$ alkenyl), substituted or unsubstituted alkynyl (e.g., substituted or unsubstituted C$_{2-6}$ alkynyl), substituted or unsubstituted carbocyclyl (e.g., substituted or unsubstituted, 3- to 7-membed, monocyclic carbocyclyl comprising zero, one, or two double bonds in the carbocyclic ring system), substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur), substituted or unsubstituted aryl (e.g., substituted or unsubstituted phenyl), substituted or unsubstituted heteroaryl (e.g., substituted or unsubstituted, 5- to 6-membed, monocyclic heteroaryl, wherein one, two, three, or four atoms in the heteroaryl ring system are independently nitrogen, oxygen, or sulfur), a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. In certain embodiments, two instances of $R^1$ are joined to form a substituted or unsubstituted heterocyclic or substituted or unsubstituted heteroaryl ring.

Formula (I) also includes substituent $R^B$ on the phenazinyl ring. In certain embodiments, $R^B$ is hydrogen. In certain embodiments, $R^B$ is not hydrogen. In certain embodiments, $R^B$ is halogen. In certain embodiments, $R^B$ is F. In certain embodiments, $R^B$ is Cl. In certain embodiments, $R^B$ is Br. In certain embodiments, $R^B$ is I. In certain embodiments, $R^B$ is halogen or substituted or unsubstituted alkyl. In certain embodiments, $R^B$ is halogen or unsubstituted C$_{1-6}$ alkyl. In certain embodiments, $R^B$ is substituted or unsubstituted alkyl. In certain embodiments, $R^B$ is substituted or unsubstituted C$_{1-6}$ alkyl. In certain embodiments, $R^B$ is Me. In certain embodiments, $R^B$ is substituted methyl (e.g., —CH$_2$F, —CHF$_2$, —CF$_3$, or Bn). In certain embodiments, $R^B$ is Et, substituted ethyl (e.g., fluorinated ethyl (e.g., perfluoroethyl)), Pr, substituted propyl (e.g., fluorinated propyl (e.g., perfluoropropyl)), Bu, or substituted butyl (e.g., fluorinated butyl (e.g., perfluorobutyl)). In certain embodiments, $R^B$ is substituted or unsubstituted alkenyl (e.g., substituted or unsubstituted C$_{2-6}$ alkenyl). In certain embodiments, $R^B$ is substituted or unsubstituted alkynyl (e.g., substituted or unsubstituted C$_{2-6}$ alkynyl). In certain embodiments, $R^B$ is substituted or unsubstituted carbocyclyl (e.g., substituted or unsubstituted, 3- to 7-membed, monocyclic carbocyclyl comprising zero, one, or two double bonds in the carbocyclic ring system). In certain embodiments, $R^B$ is substituted or unsubstituted cyclopropyl, substituted or unsubstituted cyclobutyl, substituted or unsubstituted cyclopentyl, or substituted or unsubstituted cyclohexyl. In certain embodiments, $R^B$ is substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^B$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^B$ is substituted or unsubstituted aryl (e.g., substituted or unsubstituted, 6- to 10-membered aryl). In certain embodiments, $R^B$ is unsubstituted phenyl. In certain embodiments, $R^B$ is substituted phenyl. In certain embodiments, $R^B$ is substituted or unsubstituted naphthyl. In certain embodiments, $R^B$ is substituted or unsubstituted heteroaryl. In certain embodiments, $R^B$ is substituted or unsubstituted, 5- to 6-membed, monocyclic heteroaryl, wherein one, two, three, or four atoms in the heteroaryl ring system are independently nitrogen, oxygen, or sulfur. In certain embodiments, $R^B$ is substituted or unsubstituted, 9- to 10-membed, bicyclic heteroaryl, wherein one, two, three, or four atoms in the heteroaryl ring system are independently nitrogen, oxygen, or sulfur. In certain embodiments, $R^B$ is —OR$^1$ (e.g., —OH, —O(substituted or unsubstituted C$_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, $R^B$ is —OMe. In certain embodiments, $R^B$ is —SR$^1$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)). In certain embodiments, $R^B$ is —N(R$^1$)$_2$ (e.g., —NH$_2$, —NH(substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, $R^B$ is —CN or —SCN. In certain embodiments, $R^B$ is —NO$_2$. In certain embodiments, $R^B$ is —C(=NR$^1$)R$^1$, —C(=NR$^1$)OR$^1$, or —C(=NR$^1$)N(R$^1$)$_2$. In certain embodiments, $R^B$ is —C(=O)R$^1$ (e.g., —C(=O)(substituted or unsubstituted alkyl) (e.g., —C(=O)Me) or —C(=O)(substituted or unsubstituted phenyl)). In certain embodiments, $R^B$ is —C(=O)OR$^1$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^B$ is —C(=O)N($R^1$)$_2$ (e.g., —C(=O)NH$_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^B$ is —NR$^1$C(=O)R$^1$ (e.g., —NHC(=O)(substituted or unsubstituted $C_{1-6}$ alkyl) (e.g., —NHC(=O)Me) or —NHC(=O)(substituted or unsubstituted phenyl)). In certain embodiments, $R^B$ is —NR$^1$C(=O)OR$^1$. In certain embodiments, $R^B$ is —NR$^1$C(=O)N(R)$_2$ (e.g., —NHC(=O)NH$_2$, —NHC(=O)NH(substituted or unsubstituted $C_{1-6}$ alkyl) (e.g., —NHC(=O)NHMe)). In certain embodiments, $R^B$ is —OC(=O)R$^1$ (e.g., —OC(=O)(substituted or unsubstituted alkyl) or —OC(=O)(substituted or unsubstituted phenyl)), —OC(=O)OR$^1$ (e.g., —OC(=O)O(substituted or unsubstituted alkyl) or —OC(=O)O(substituted or unsubstituted phenyl)), or —OC(=O)N($R^1$)$_2$ (e.g., —OC(=O)NH$_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

Formula (I) also includes substituent $R^C$ on the phenazinyl ring. In certain embodiments, $R^C$ is hydrogen. In certain embodiments, $R^C$ is not hydrogen. In certain embodiments, $R^C$ is halogen. In certain embodiments, $R^C$ is F. In certain embodiments, $R^C$ is Cl. In certain embodiments, $R^C$ is Br. In certain embodiments, $R^C$ is I. In certain embodiments, $R^C$ is halogen or substituted or unsubstituted alkyl. In certain embodiments, $R^C$ is halogen or unsubstituted $C_{1-6}$ alkyl. In certain embodiments, $R^C$ is substituted or unsubstituted alkyl. In certain embodiments, $R^C$ is substituted or unsubstituted $C_{1-6}$ alkyl. In certain embodiments, $R^C$ is Me. In certain embodiments, $R^C$ is substituted methyl (e.g., —CH$_2$F, —CHF$_2$, —CF$_3$, or Bn). In certain embodiments, $R^C$ is Et, substituted ethyl (e.g., fluorinated ethyl (e.g., perfluoroethyl)), Pr, substituted propyl (e.g., fluorinated propyl (e.g., perfluoropropyl)), Bu, or substituted butyl (e.g., fluorinated butyl (e.g., perfluorobutyl)). In certain embodiments, $R^C$ is substituted or unsubstituted alkenyl (e.g., substituted or unsubstituted $C_{2-6}$ alkenyl). In certain embodiments, $R^C$ is substituted or unsubstituted alkynyl (e.g., substituted or unsubstituted $C_{2-6}$ alkynyl). In certain embodiments, $R^C$ is substituted or unsubstituted carbocyclyl (e.g., substituted or unsubstituted, 3- to 7-membed, monocyclic carbocyclyl comprising zero, one, or two double bonds in the carbocyclic ring system). In certain embodiments, $R^C$ is substituted or unsubstituted cyclopropyl, substituted or unsubstituted cyclobutyl, substituted or unsubstituted cyclopentyl, or substituted or unsubstituted cyclohexyl. In certain embodiments, $R^C$ is substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^C$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^C$ is substituted or unsubstituted aryl (e.g., substituted or unsubstituted, 6- to 10-membered aryl). In certain embodiments, $R^C$ is unsubstituted phenyl. In certain embodiments, $R^C$ is substituted phenyl. In certain embodiments, $R^C$ is substituted or unsubstituted naphthyl. In certain embodiments, $R^C$ is substituted or unsubstituted heteroaryl. In certain embodiments, $R^C$ is substituted or unsubstituted, 5- to 6-membed, monocyclic heteroaryl, wherein one, two, three, or four atoms in the heteroaryl ring system are independently nitrogen, oxygen, or sulfur. In certain embodiments, $R^C$ is substituted or unsubstituted, 9- to 10-membed, bicyclic heteroaryl, wherein one, two, three, or four atoms in the heteroaryl ring system are independently nitrogen, oxygen, or sulfur. In certain embodiments, $R^C$ is halogen, substituted or unsubstituted alkyl, or —OR$^1$. In certain embodiments, $R^C$ is halogen, substituted or unsubstituted alkyl, —O(substituted or unsubstituted alkyl), or —O(substituted or unsubstituted phenyl). In certain embodiments, $R^C$ is —OR$^1$ (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, $R^C$ is —OMe. In certain embodiments, $R^C$ is —SR$^1$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^C$ is —N($R^1$)$_2$ (e.g., —NH$_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, $R^C$ is —CN or —SCN. In certain embodiments, $R^C$ is —NO$_2$. In certain embodiments, $R^C$ is —C(=NR$^1$)R$^1$, —C(=NR$^1$)OR$^1$, or —C(=NR$^1$)N($R^1$)$_2$. In certain embodiments, $R^C$ is —C(=O)R$^1$ (e.g., —C(=O)(substituted or unsubstituted alkyl) (e.g., —C(=O)Me) or —C(=O)(substituted or unsubstituted phenyl)). In certain embodiments, $R^C$ is —C(=O)OR$^1$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^C$ is —C(=O)N($R^1$)$_2$ (e.g., —C(=O)NH$_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^C$ is —NR$^1$C(=O)R$^1$ (e.g., —NHC(=O)(substituted or unsubstituted $C_{1-6}$ alkyl) (e.g., —NHC(=O)Me) or —NHC(=O)(substituted or unsubstituted phenyl)). In certain embodiments, $R^C$ is —NR$^1$C(=O)OR$^1$. In certain embodiments, $R^C$ is —NR$^1$C(=O)N($R^1$)$_2$ (e.g., —NHC(=O)NH$_2$, —NHC(=O)NH(substituted or unsubstituted $C_{1-6}$ alkyl) (e.g., —NHC(=O)NHMe)). In certain embodiments, $R^C$ is —OC(=O)R$^1$ (e.g., —OC(=O)(substituted or unsubstituted alkyl) or —OC(=O)(substituted or unsubstituted phenyl)), —OC(=O)OR$^1$ (e.g., —OC(=O)O(substituted or unsubstituted alkyl) or —OC(=O)O(substituted or unsubstituted phenyl)), or —OC(=O)N($R^1$)$_2$ (e.g., —OC(=O)NH$_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

Formula (I) also includes substituent $R^D$ on the phenazinyl ring. In certain embodiments, $R^D$ is hydrogen. In certain embodiments, $R^D$ is not hydrogen. In certain embodiments, $R^D$ is halogen. In certain embodiments, $R^D$ is F. In certain embodiments, $R^D$ is Cl. In certain embodiments, $R^D$ is Br. In certain embodiments, $R^D$ is I. In certain embodiments, $R^D$ is halogen or substituted or unsubstituted alkyl. In certain embodiments, $R^D$ is halogen or unsubstituted $C_{1-6}$ alkyl. In certain embodiments, $R^D$ is substituted or unsubstituted alkyl. In certain embodiments, $R^D$ is substituted or unsubstituted $C_{1-6}$ alkyl. In certain embodiments, $R^D$ is Me. In certain embodiments, $R^D$ is substituted methyl (e.g., —CH$_2$F, —CHF$_2$, —CF$_3$, or Bn). In certain embodiments, $R^D$ is Et, substituted ethyl (e.g., fluorinated ethyl (e.g., perfluoroethyl)), Pr, substituted propyl (e.g., fluorinated propyl (e.g., perfluoropropyl)), Bu, or substituted butyl (e.g., fluorinated butyl (e.g., perfluorobutyl)). In certain embodiments, $R^D$ is substituted or unsubstituted alkenyl (e.g., substituted or unsubstituted $C_2$-6 alkenyl). In certain embodiments, $R^D$ is substituted or unsubstituted alkynyl (e.g., substituted or unsubstituted $C_{2-6}$ alkynyl). In certain embodiments, $R^D$ is substituted or unsubstituted carbocyclyl (e.g., substituted or unsubstituted, 3- to 7-membed, monocyclic carbocyclyl comprising zero, one, or two double bonds in the carbocyclic ring system). In certain embodiments, $R^D$ is substituted or unsubstituted cyclopropyl, substituted or unsubstituted cyclobutyl, substituted or unsubstituted cyclopentyl, or substituted or unsubstituted cyclohexyl. In certain embodiments, $R^D$ is substituted or unsubstituted heterocyclyl (e.g., substituted or unsubstituted, 3- to 7-membed, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^D$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^D$ is substituted or unsubstituted aryl (e.g., substituted or unsubstituted, 6- to 10-membered aryl). In certain embodiments, $R^D$ is unsubstituted phenyl. In certain embodiments, $R^D$ is substituted phenyl. In certain embodiments, $R^D$ is substituted or unsubstituted naphthyl. In certain embodiments, $R^D$ is substituted or unsubstituted heteroaryl. In certain embodiments, $R^D$ is substituted or unsubstituted, 5- to 6-membed, monocyclic heteroaryl, wherein one, two, three, or four atoms in the heteroaryl ring system are independently nitrogen, oxygen, or sulfur. In certain embodiments, $R^D$ is substituted or unsubstituted, 9- to 10-membed, bicyclic heteroaryl, wherein one, two, three, or four atoms in the heteroaryl ring system are independently nitrogen, oxygen, or sulfur. In certain embodiments, $R^D$ is —OR$^1$ (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, $R^D$ is —OMe. In certain embodiments, $R^D$ is —SR$^1$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^D$ is —N(R$^1$)$_2$ (e.g., —NH$_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, $R^D$ is —CN or —SCN. In certain embodiments, $R^D$ is —NO$_2$. In certain embodiments, $R^D$ is —C(=NR$^1$)R$^1$, —C(=NR$^1$)OR$^1$, or —C(=NR$^1$)N(R$^1$)$_2$. In certain embodiments, $R^D$ is —C(=O)R$^1$ (e.g., —C(=O)(substituted or unsubstituted alkyl) (e.g., —C(=O)Me) or —C(=O)(substituted or unsubstituted phenyl)). In certain embodiments, $R^D$ is —C(=O)OR$^1$ (e.g., —C(=O)OH, —C(=O)O(substituted or unsubstituted alkyl) (e.g., —C(=O)OMe), or —C(=O)O(substituted or unsubstituted phenyl)). In certain embodiments, $R^D$ is —C(=O)N(R$^1$)$_2$ (e.g., —C(=O)NH$_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, $R^D$ is —NR$^1$C(=O)R$^1$ (e.g., —NHC(=O)(substituted or unsubstituted $C_{1-6}$ alkyl) (e.g., —NHC(=O)Me) or —NHC(=O)(substituted or unsubstituted phenyl)). In certain embodiments, $R^D$ is —NR$^1$C(=O)OR$^1$. In certain embodiments, $R^D$ is —NR$^1$C(=O)N(R$^1$)$_2$ (e.g., —NHC(=O)NH$_2$, —NHC(=O)NH(substituted or unsubstituted $C_{1-6}$ alkyl) (e.g., —NHC(=O)NHMe)). In certain embodiments, $R^D$ is —OC(=O)R$^1$ (e.g., —OC(=O)(substituted or unsubstituted alkyl) or —OC(=O)(substituted or unsubstituted phenyl)), —OC(=O)OR$^1$ (e.g., —OC(=O)O(substituted or unsubstituted alkyl) or —OC(=O)O(substituted or unsubstituted phenyl)), or —OC(=O)N(R$^1$)$_2$ (e.g., —OC(=O)NH$_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

In certain embodiments, the compound is of the formula:

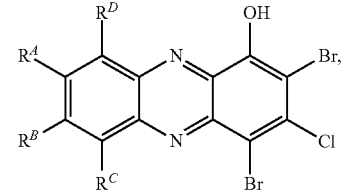

or a salt, solvate, hydrate, polymorph, co-crystal, tautomer, stereoisomer, isotopically labeled compound, or prodrug thereof.

In certain embodiments, the compound is of the formula:

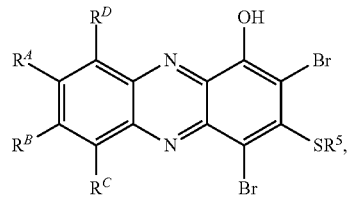

or a salt, solvate, hydrate, polymorph, co-crystal, tautomer, stereoisomer, isotopically labeled compound, or prodrug thereof.

In certain embodiments, the compound is of the formula:

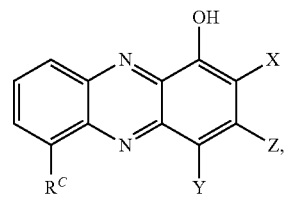

or a salt, solvate, hydrate, polymorph, co-crystal, tautomer, stereoisomer, isotopically labeled compound, or prodrug thereof, provided that $R^C$ is not hydrogen.

In certain embodiments, the compound is of the formula:

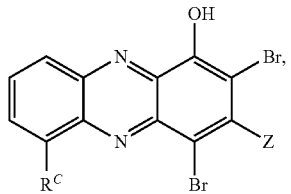
(5)

or a salt, solvate, hydrate, polymorph, co-crystal, tautomer, stereoisomer, isotopically labeled compound, or prodrug thereof, provided that $R^C$ is not hydrogen.

In certain embodiments, the compound is of the formula:

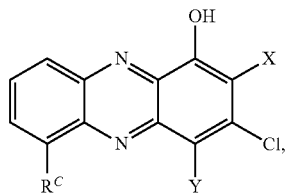

or a salt, solvate, hydrate, polymorph, co-crystal, tautomer, stereoisomer, isotopically labeled compound, or prodrug thereof, provided that $R^C$ is not hydrogen.

In certain embodiments, the compound is of the formula:

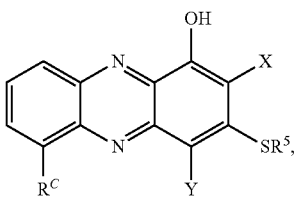

or a salt, solvate, hydrate, polymorph, co-crystal, tautomer, stereoisomer, isotopically labeled compound, or prodrug thereof, provided that $R^C$ is not hydrogen.

In certain embodiments, the compound is of the formula:

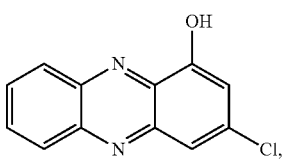
(18)

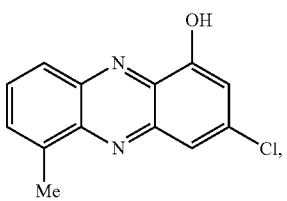
(19)

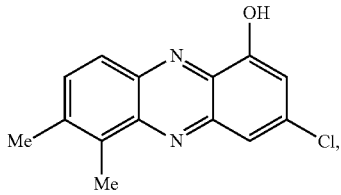
(20)

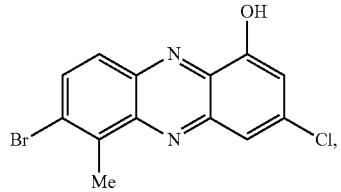
(21)

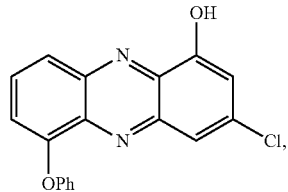
(22)

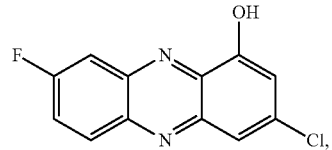
(23)

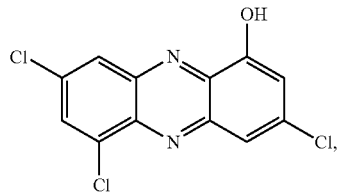
(24)

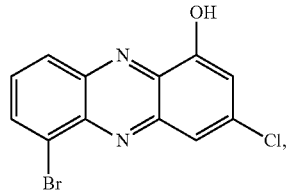
(25)

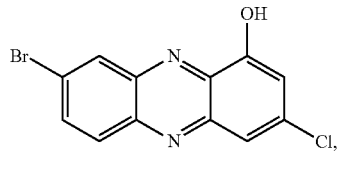
(26)

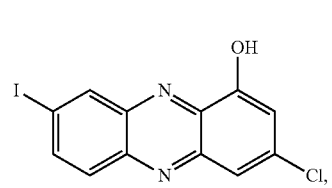
(27)

(28) 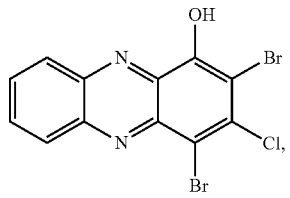
(29) 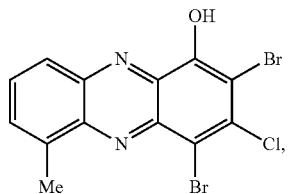
(30) 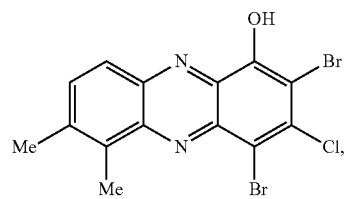
(31) 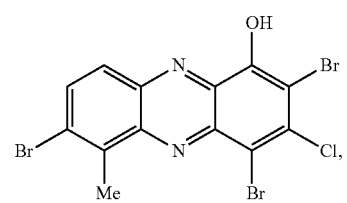
(32) 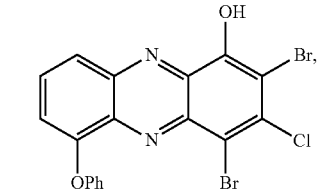
(33) 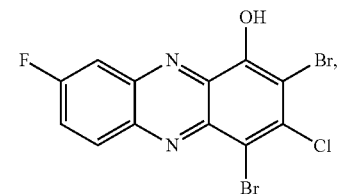
(34) 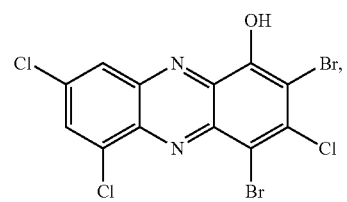
(35) 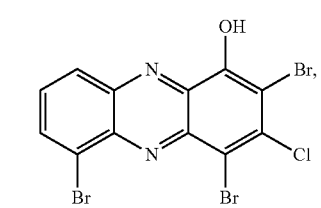
(36) 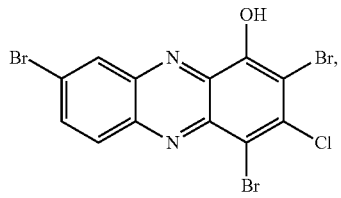
(37) 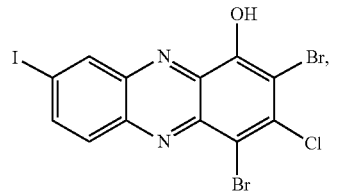
(42) 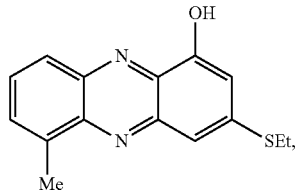
(43) 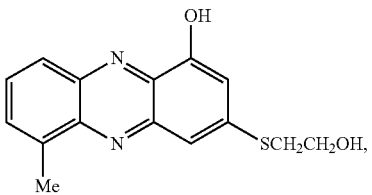
(44) 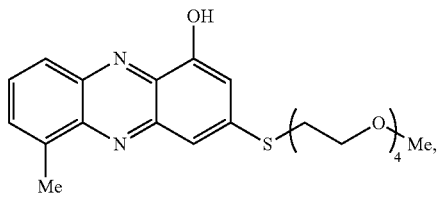
(45) 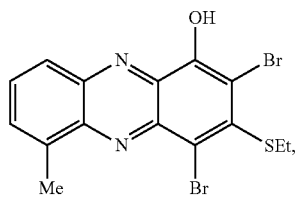
(46) 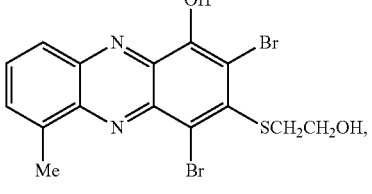
(47) 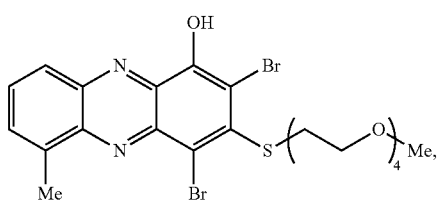

or a salt, solvate, hydrate, polymorph, co-crystal, tautomer, stereoisomer, isotopically labeled compound, or prodrug thereof.

In certain embodiments, the compound is Compound No. 28, or a salt, solvate, hydrate, polymorph, co-crystal, tautomer, stereoisomer, isotopically labeled compound, or prodrug thereof. In certain embodiments, the compound is Compound No. 29, or a salt, solvate, hydrate, polymorph, co-crystal, tautomer, stereoisomer, isotopically labeled compound, or prodrug thereof. In certain embodiments, the compound is Compound No. 34, or a salt, solvate, hydrate, polymorph, co-crystal, tautomer, stereoisomer, isotopically labeled compound, or prodrug thereof.

In certain embodiments, the compound is of the formula:

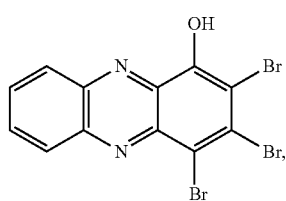

(150)

or a salt, solvate, hydrate, polymorph, co-crystal, tautomer, stereoisomer, isotopically labeled compound, or prodrug thereof.

In certain embodiments, the compounds of the invention are the compounds described herein, and salts (e.g., pharmaceutically acceptable salts), solvates, hydrates, polymorphs, co-crystals, tautomers, stereoisomers, isotopically labeled compounds, and prodrugs thereof. In certain embodiments, the prodrug is a prodrug (e.g., ester prodrug) of the hydroxy moiety at the 1-postion of the compounds described herein. The prodrugs may enhance physicochemical properties, mitigate off-target metal binding that could lead to toxicity, and release via bacteria-specific mechanisms.[37,38,56,57] In certain embodiments, the compounds of the invention are the compounds described herein, and pharmaceutically acceptable salts thereof. In certain embodiments, the compounds of the invention are the compounds described herein, and pharmaceutically acceptable salts thereof. In certain embodiments, the compounds of the invention are the compounds of Formula (I), and pharmaceutically acceptable salts, solvates, hydrates, polymorphs, co-crystals, tautomers, stereoisomers, isotopically labeled compounds, and prodrugs thereof. In certain embodiments, the compounds of the invention are the compounds of Formula (I), and salts (e.g., pharmaceutically acceptable salts) thereof. In certain embodiments, the compounds of the invention are the compounds of Formula (I), and pharmaceutically acceptable salts, tautomers, and isotopically labeled compounds thereof. When at least one of X, Z, and Y is halogen, a compound described herein may be referred to as an HP.

In certain embodiments, the compounds of the invention are substantially pure. In certain embodiments, a compound of the invention is at least about 90%, at least about 95%, at least about 97%, at least about 98%, at least about 99%, or at least about 99.5% free of impurities.

The compounds of the invention have been found to be antimicrobial agents (e.g., antibacterial agents). Without wishing to be bound by a particular theory, the compounds of the invention may be redox-active and may generate reactive oxygen species (ROS). The inventive compounds may thus act as microbial warfare agents and inhibit the growth and/or reproduction of or kill a microorganism (e.g., bacterium, mycobacterium, archaeon, protist, fungus, or parasite) by oxidizing and/or reducing molecules (e.g., catalase, cytokine, nicotinamide adenine dinucleotide phosphate (NADPH), and nicotinamide adenine dinucleotide phosphate ($NADP^+$)) in, near, or around the microorganism. The activity of a compound of the invention against a microorganism may be measured by the minimum inhibitory concentration (MIC) of the compound in inhibiting the viability, growth, or replication of the microorganism. In certain embodiments, the MIC of a compound of the invention is an MIC in inhibiting the viability the microorganism. In certain embodiments, the MIC value of an inventive compound in inhibiting a microorganism is at most about 1 nM, at most about 3 nM, at most about 10 nM, at most about 30 nM, at most about 100 nM, at most about 300 nM, at most about 1 µM, at most about 3 µM, at most about 10 µM, at most about 30 µM, or at most about 100 µM. In certain embodiments, the MIC value of an inventive compound in inhibiting a microorganism is at least about 1 nM, at least about 3 nM, at least about 10 nM, at least about 30 nM, at least about 100 nM, at least about 300 nM, at least about 1 µM, at least about 3 µM, at least about 10 µM, or at least about 30 µM. In certain embodiments, MIC values are measured according to the guidelines of the Clinical and Laboratory Standards Institute (CLSI) (which is incorporated herein by reference) (e.g., a broth microdilution method). In certain embodiments, MIC values are measured by a method described herein.

The activity of a compound of the invention against a microorganism may also be measured by the half maximal inhibitory concentration ($IC_{50}$) of the compound in inhibiting the viability, growth, or replication of the microorganism. In certain embodiments, the $IC_{50}$ of a compound of the invention is an MIC in inhibiting the viability the microorganism. In certain embodiments, the $IC_{50}$ value of an inventive compound in inhibiting a microorganism is at most about 1 nM, at most about 3 nM, at most about 10 nM, at most about 30 nM, at most about 100 nM, at most about 300 nM, at most about 1 µM, at most about 3 µM, at most about 10 µM, at most about 30 µM, or at most about 100 µM. In certain embodiments, the $IC_{50}$ value of an inventive compound in inhibiting a microorganism is at least about 1 nM, at least about 3 nM, at least about 10 nM, at least about 30 nM, at least about 100 nM, at least about 300 nM, at least about 1 µM, at least about 3 µM, at least about 10 µM, or at least about 30 µM. In certain embodiments, $IC_{50}$ values are measured according to the guidelines of the CLSI (e.g., a microdilution method). In certain embodiments, $IC_{50}$ values are measured by a method described herein.

The compounds of the invention may selectively inhibit the growth and/or reproduction of or kill a microorganism. In certain embodiments, a compound of the invention is more active in inhibiting the growth and/or reproduction of or killing a first microorganism (e.g., a microorganism described herein) than in inhibiting the growth and/or reproduction of or killing a host cell. In certain embodiments, a compound of the invention is more active in inhibiting the growth and/or reproduction of or killing a first microorganism than in inhibiting the growth and/or reproduction of or killing a second microorganism. The selectivity of an inventive compound in inhibiting the growth and/or reproduction of or killing a first microorganism over a host cell or a second microorganism may be determined by the quotient of the MIC value of the inventive compound in inhibiting the growth and/or reproduction of or killing the host cell or second microorganism over the MIC value of the inventive compound in inhibiting the growth and/or reproduction of or killing the first microorganism. The selectivity of an inventive compound in inhibiting the growth and/or reproduction of or killing a first microorganism over a host cell or a second microorganism may also be determined by the quotient of the $IC_{50}$ value of the inventive compound in inhibiting the growth and/or reproduction of or killing the host cell or second microorganism over the $IC_{50}$ value of the inventive compound in inhibiting the growth and/or reproduction of or killing the first microorganism. In certain embodiments, the selectivity of an inventive compound in inhibiting the growth and/or reproduction of or killing a first microorganism over a host cell or a second microorganism is at least about 3-fold, at least about 10-fold, at least about 30-fold, at least about 100-fold, at least about 1,000-fold, at least about 10,000-fold, or at least about 100,000-fold.

The compounds of the invention may show low cytotoxicity toward mammalian cells (e.g., cytotoxicity $IC_{50}$ against HeLa cells being greater than 100 μM). The compounds of the invention may show low hemolysis activity (e.g., not more than 1%, not more than 2%, not more than 4%, or not more than 6% hemolysis of red blood cells (RBCs) when treated with the compound at 200 μM).

Compositions, Kits, and Administration

The present invention also provides compositions (e.g., pharmaceutical compositions) comprising a compound of the invention, and optionally an excipient (e.g., pharmaceutically acceptable excipient).

In certain embodiments, a composition of the invention is useful for disinfecting a surface. In certain embodiments, the compound of the invention is provided in an effective amount in the composition. In certain embodiments, the amount of the compound included in the composition is effective for killing at least 80%, at least 90%, at least 95%, at least 99%, at least 99.9%, or at least 99.99% of the microorganisms on the surface. In certain embodiments, the amount of the compound included in the composition is effective for killing at most 90%, at most 95%, at most 99%, at most 99.9%, at most 99.99%, or at most 99.999% of the microorganisms on the surface. A composition of the invention may include one or more excipients (e.g., water, detergent, bleach, surfactant) (e.g., pharmaceutically acceptable excipients).

In certain embodiments, a composition of the invention is a composition (e.g., pharmaceutical composition) comprising a compound of the invention and optionally a pharmaceutically acceptable excipient. In certain embodiments, the compound of the invention is provided in an effective amount in the pharmaceutical composition. In certain embodiments, the effective amount of the compound is a therapeutically effective amount. In certain embodiments, the effective amount of the compound is a prophylactically effective amount. The pharmaceutical compositions of the invention may be useful in the inventive methods. In certain embodiments, the pharmaceutical compositions are useful in treating a microbial infection (e.g., a bacterial infection or mycobacterial infection). In certain embodiments, the pharmaceutical compositions are useful in preventing a microbial infection (e.g., a bacterial infection or mycobacterial infection). In certain embodiments, the pharmaceutical compositions are useful in inhibiting the growth of a microorganism (e.g., a microorganism described herein). In certain embodiments, the pharmaceutical compositions are useful in inhibiting the reproduction of a microorganism. In certain embodiments, the pharmaceutical compositions are useful in killing a microorganism. In certain embodiments, the pharmaceutical compositions are useful in inhibiting the formation and/or growth of a biofilm. In certain embodiments, the pharmaceutical compositions are useful in reducing or removing a biofilm. In certain embodiments, the pharmaceutical compositions are useful in disinfecting a surface. In certain embodiments, the pharmaceutical compositions are useful in cleaning a surface.

Pharmaceutical compositions described herein can be prepared by any method known in the art of pharmacology. In general, such preparatory methods include the steps of bringing the compound of the invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a microbial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that a compound or composition, as described herein, can be administered in combination with one or more additional pharmaceutical agents. In certain embodiments, the additional pharmaceutical agent is different from a compound of the invention, or a pharmaceutically acceptable salt, solvate, hydrate, polymorph, co-crystal, tautomer, stereoisomer, isotopically labeled compound, or prodrug thereof. The compounds or compositions can be administered in combination with additional pharmaceutical agents to improve their potency, efficacy, and/or bioavailability, reduce and/or modify their metabolism, inhibit their excretion, and/or modify their distribution within the body. It will also be appreciated that the therapy employed may achieve a desired effect for the same disorder, and/or it may achieve different effects. In certain embodiments, the combination of a compound of the invention and an additional pharmaceutical agent shows a synergistic effect.

The compound or composition can be administered concurrently with, prior to, or subsequent to, one or more additional pharmaceutical agents, which are different from the compound or composition and may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents in combination be utilized at levels that do not exceed the levels at which they are utilized individually. In some embodiments, the levels utilized in combination will be lower than those utilized individually.

Exemplary additional pharmaceutical agents include, but are not limited to, antibiotics (e.g., antibacterial agents, antiviral agents, anti-fungal agents), anti-inflammatory agents, anti-pyretic agents, and pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a chelator of a metal ion or metal atom. In certain embodiments, the additional pharmaceutical agent is a chelator of a divalent metal ion (e.g., Mg(II), Ca(II), Sr(II), Mn(II), Fe(II), Co(II), Ni(II), Cu(II), or Zn(II)). In certain embodiments, the additional pharmaceutical agent is a chelator of Cu(II), Mg(II), or Fe(II). In certain embodiments, the additional pharmaceutical agent is disodium 4,5-dihydroxy-1,3-benzenedisulfonate (TIRON). In certain embodiments, the additional pharmaceutical agent is 2,2'-dipyridyl, desferrioxamine (DFO, DESFERAL), deferasirox (EXJADE), deferiprone (L1, FERRIPROX), FERALEX-G, CaNa$_3$DTPA, dexrazoxane, a phosphorothioate-oligonucleotide, desferrithiocin, or desazadesferrithiocin, or a derivative thereof. In certain embodiments, the additional pharmaceutical agent is an antibiotic. In certain embodiments, the additional pharmaceutical agent is an antibiotic effective against a microorganism described herein. In certain embodiments, the additional pharmaceutical agent is an antibiotic effective against a bacterium. In certain embodiments, the additional pharmaceutical agent is an antibiotic effective against a Gram-positive bacterium (e.g., a *Staphylococcus* species or *Enterococcus* species). In certain embodiments, the additional pharmaceutical agent is an antibiotic effective against a Gram-negative bacterium (e.g., an *Acinetobacter* species). In certain embodiments, the additional pharmaceutical agent is an antibiotic effective against a multidrug-resistant bacterium. In certain embodiments, the additional pharmaceutical agent is a β-lactam antibiotic. In certain embodiments, the additional pharmaceutical agent is a penicillin (e.g., a penam, such as an aminopenicillin (e.g., amoxicillin, an ampicillin (e.g., pivampicillin, hetacillin, bacampicillin, metampicillin, talampicillin), epicillin), a carboxypenicillin (e.g., a carbenicillin (e.g., carindacillin), ticarcillin, temocillin), a ureidopenicillin (e.g., azlocillin, piperacillin, mezlocillin), a mecillinam (e.g., pivmecillinam), sulbenicillin, benzylpenicillin, clometocillin, benzathine benzylpenicillin, procaine benzylpenicillin, azidocillin, penamecillin, phenoxymethylpenicillin, propicillin, benzathine phenoxymethylpenicillin, pheneticillin, a cloxacillin (e.g., dicloxacillin, flucloxacillin), oxacillin, methicillin, nafcillin), a penem (e.g., faropenem), a carbapenem (e.g., biapenem, ertapenem, an antipseudomonal (e.g., doripenem, imipenem, meropenem), panipenem), a cephalosporin (e.g., a cephem, such as cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, a cephamycin (e.g, cefoxitin, cefotetan, cefmetazole), a carbacephem (e.g., loracarbef), cefixime, ceftriaxone, an antipseudomonal (e.g., ceftazidime, cefoperazone), cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, an oxacephem (e.g., flomoxef, latamoxef), cefepime, cefozopran, cefpirome, cefquinome, ceftobiprole, ceftaroline fosamil, ceftiofur, cefquinome, cefovecin), a monobactam (e.g., aztreonam, tigemonam, carumonam, nocardicin A), an aminoglycoside (e.g., amikacin, gentamicin, kanamycin, neomycin, netilmicin, tobramycin, paromomycin, spectinomycin), an ansamycin (e.g., geldanamycin, herbimycin, rifaximin), a glycopeptide (e.g., teicoplanin, vancomycin, telavancin), a lincosamide (e.g., clindamycin, lincomycin), a lipopeptide (e.g., daptomycin), a macrolide (e.g., azithromycin, clarithromycin, dirithromycin, erythromycin, roxithromycin, troleandomycin, telithromycin, spiramycin), a nitrofuran (e.g., furazolidone, nitrofurantoin), an oxazolidonone (e.g., linezolid, posizolid, radezolid, torezolid), a polypeptide (e.g., bacitracin, colistin, polymyxin B), a quinolone (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin), a sulfonamide (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim, sulfonamidochrysoidine), a tetracycline (e.g., demeclocycline, doxycycline, minocycline, oxytetracycline, tetracycline), clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim. In certain embodiments, the additional pharmaceutical agent is an antiviral agent. In certain embodiments, the additional pharmaceutical agent is (−)-Oseltamivir, j-D-ribofuranose, 1-acetate 2,3,5-tribenzoate, 1-Docosanol, 2-Amino-6-chloropurine, 5-Iodo-2'-deoxyuridine, 6-Chloropurine, Abacavir sulfate, Abacavir-epivir mixt., Acyclovir, Acyclovir sodium, Adefovir dipivoxil, Amantadine (e.g., Amantadine hydrochloride), Amantadine hydrochloride, anti-HIV agent (e.g., Abacavir, Amprenavir, Atazanavir, Azidothymidine, Bryostatin (e.g., Bryostatin 1, Bryostatin 10, Bryostatin 11, Bryostatin 12, Bryostatin 13, Bryostatin 14, Bryostatin 15, Bryostatin 16, Bryostatin 17, Bryostatin 18, Bryostatin 19, Bryostatin 2, Bryostatin 20, Bryostatin 3, Bryostatin 4, Bryostatin 5, Bryostatin 6, Bryostatin 7, Bryostatin 8, Bryostatin 9), Dideoxycytidine, Dideoxyinosine, Efavirenz, Indinavir, Lamivudine, Lopinavir, Nevirapine, Ritonavir, Saquinavir, Stavudine, Tenofovir), Azauridine, ombivir, Deoxynojirimycin, Docosanol, Fomivirsen sodium, Foscarnet, Ganciclovir, Integrase inhibitors (e.g., 5CITEP, Chloropeptin I, Complestatin, Dolutegravir, Elvitegravir, L 708906, L 731988, MK 2048, Raltegravir, Raltegravir potassium), MK 5172, MK 8742, Palivizumab, Pegylated interferon alfa-2b, Phosphonoacetic acid, Ribavirin, Simeprevir, Sofosbuvir, Tubercidin, Vidarabine, or virus entry inhibitor (e.g., Enfuvirtide, Maraviroc). In certain embodiments, the additional pharmaceutical agent is a fungicide. In certain embodiments, the additional pharmaceutical agent is (−)-Fumagillin, (−)-Metalaxyl, 1,2,5-Fluorocytosine, Acrisorcin, Anilazine, Antifouling agent, Azoxystrobin, Benomyl, Bordeaux mixture, Captan, Carbendazim, Caspofungin acetate, Chlorothalonil, Clotrimazole, Dichlofluanid, Dinocap, Dodine, Fenhexamid, Fenpropimorph, Ferbam, Fluconazole, Fosetyl Al, Griseofulvin, Guanidine (e.g., Agmatine, Amiloride hydrochloride, Biguanide (e.g., Imidodicarbonimidic diamide, N,N-dimethyl-, hydrochloride (1:1) (e.g., Metformin hydrochloride), Metformin), Cimetidine, Guanethidine, Guanfacine, Guanidine, Guanidinium, Methylguanidine, Sulfaguanidine), Iprobenfos, Iprodione, Isoprothiolane, Itraconazole, Ketoconazole, Mancozeb, Metalaxyl, Metiram, Miconazole, Natamycin, Nystatin, Oxycarboxine, Pentachloronitrobenzene, Prochloraz, Procymidone, Propiconazole, Pyrazophos, Reduced viscotoxin A3, Salicylanilide, Tebuconazole, Terbinafine, Thiabendazole, Thiophanate, Thiophanate methyl, Triadimefon, Vinclozolin, or Voriconazole. In certain embodiments, the additional pharmaceutical agent is a protozoacide. In certain embodiments, the additional pharmaceutical agent is Amebicide, Antimalarial (e.g., Artemisinin, Chloroquine (e.g., Chloroquine phosphate), Mefloquine, Sulfadoxine), Coccidiostat, Leishmanicide, Trichomonacide, or Trypanosomicide (e.g., Eflornithine). In certain embodiments, the additional pharmaceutical agent is a parasiticide. In certain embodiments, the additional pharmaceutical agent is antihelmintic (e.g., Abamectin, Dimethylformocarbothialdine, Niclosamide, Schistosomicide), protozoacide (e.g., Amebicide, antimalarial (e.g., Artemisinin, chloroquine (e.g., chloroquine phosphate), Mefloquine, Sulfadoxine), coccidiostat, leishmanicide, trichomonacide, or trypanosomicide (e.g., Eflornithine)).

In certain embodiments, the pharmaceutical composition is substantially free (e.g., at least 70% free, at least 80% free, at least 90% free, at least 95% free, at least 99% free, or at least 99.9% free) of a metal ion or metal atom. In certain embodiments, the pharmaceutical composition is substantially free of a divalent metal ion (e.g., Mg(II), Ca(II), Sr(II), Mn(II), Fe(II), Co(II), Ni(II), Cu(II), or Zn(II)). In certain embodiments, the pharmaceutical composition is substantially free of Cu(II), Mg(II), or Fe(II).

Also encompassed by the invention are kits (e.g., pharmaceutical packs). The kits may comprise a compound or composition (e.g., pharmaceutical composition) of the invention and instructions for using the compound or composition. The kits may comprise a container (e.g., a vial, ampule, bottle, syringe, dispenser package, tube, inhaler, and/or other suitable container). In some embodiments, a kit of the invention further includes a second container comprising an excipient (e.g., pharmaceutically acceptable excipient) for dilution or suspension of an inventive compound or composition. In some embodiments, the compound or composition of the invention provided in a first container and a second container are combined to form one unit dosage form.

In one aspect, the present invention provides kits including a first container comprising a compound or composition of the invention. In certain embodiments, a kit of the invention includes a first container comprising a compound of Formula (I), or a pharmaceutically acceptable salt thereof, or a composition thereof.

In certain embodiments, the kits are useful in treating a microbial infection in a subject in need thereof. In certain embodiments, the kits are useful in preventing a microbial infection in a subject in need thereof. In certain embodiments, the microbial infection is a bacterial infection. In certain embodiments, the bacterial infection is an infection caused by a Gram-positive bacterium. In certain embodiments, the bacterial infection is an infection caused by a Gram-negative bacterium. In certain embodiments, the microbial infection is a mycobacterial infection. In certain embodiments, the kits are useful in inhibiting the growth of a microorganism. In certain embodiments, the kits are useful in inhibiting the reproduction of a microorganism. In certain embodiments, the kits are useful in killing a microorganism. In certain embodiments, the kits are useful in inhibiting the formation and/or growth of a biofilm. In certain embodiments, the kits are useful in reducing or removing a biofilm. In certain embodiments, the kits are useful in disinfecting a surface. In certain embodiments, the kits are useful for screening a library of compounds to identify a compound that is useful in the methods of the invention. In certain embodiments, the kit further includes instructions for using the compound or pharmaceutical composition included in the kit (e.g., for administering to a subject in need of treatment of a microbial infection a compound or pharmaceutical composition of the invention, for contacting a microorganism with a compound or pharmaceutical composition of the invention, or for contacting a biofilm with a compound or pharmaceutical composition of the invention). The kits may also include information as required by a regulatory agency such as the U.S. Food and Drug Administration (FDA). In certain embodiments, the information included in the kits is prescribing information. In certain embodiments, the kits and instructions provide for treating a microbial infection in a subject in need thereof. In certain embodiments, the kits and instructions provide for preventing a microbial infection in a subject in need thereof. In certain embodiments, the kits and instructions provide for inhibiting the growth of a microorganism. In certain embodiments, the kits and instructions provide for inhibiting the reproduction of a microorganism. In certain embodiments, the kits and instructions provide for killing a microorganism. In certain embodiments, the kits and instructions provide for inhibiting the formation and/or growth of a biofilm. In certain embodiments, the kits and instructions provide for reducing or removing a biofilm. In certain embodiments, the kits and instructions provide for disinfecting a surface. In certain embodiments, the kits and instructions provide for screening a library of compounds to identify a compound that is useful in the methods of the invention. The kit of the invention may include one or more additional agents described herein (e.g., additional pharmaceutical agents) as a separate composition.

Methods of Treatment and Uses

The present invention also provides methods for treating a microbial infection (e.g., bacterial infection or mycobacterial infection) in a subject in need thereof, the methods comprising administering to the subject in need thereof an effective amount of:

a compound of Formula (I):

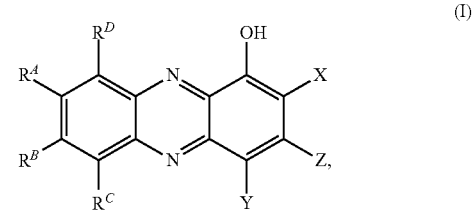

or a pharmaceutically acceptable salt, solvate, hydrate, polymorph, co-crystal, tautomer, stereoisomer, isotopically labeled compound, or prodrug thereof; or the composition of described herein;

wherein:

X is hydrogen, halogen, substituted or unsubstituted alkyl, substituted or unsubstituted alkenyl, or substituted or unsubstituted alkynyl;

Z is halogen, substituted or unsubstituted alkyl, substituted or unsubstituted alkenyl, substituted or unsubstituted alkynyl, —OR$^3$, —N(R$^4$)$_2$, —SR$^5$, —CN, —SCN, —C(=NR$^5$)R$^5$, —C(=NR$^5$)OR$^5$, —C(=NR$^5$)N(R$^5$)$_2$, —C(=O)R$^5$, —C(=O)OR$^5$, —C(=O)N(R$^5$)$_2$, —NO$_2$, —NR$^5$C(=O)R$^5$, —NR$^5$C(=O)OR$^5$, —NR$^5$C(=O)N(R$^5$)$_2$, —OC(=O)R$^5$, —OC(=O)OR$^5$, or —OC(=O)N(R$^5$)$_2$, wherein each instance of R$^3$, R$^4$, and R$^5$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R⁴ are joined to form a substituted or unsubstituted heterocyclic or substituted or unsubstituted heteroaryl ring, or two instances of R⁵ are joined to form a substituted or unsubstituted heterocyclic or substituted or unsubstituted heteroaryl ring;

Y is halogen, substituted or unsubstituted alkyl, substituted or unsubstituted alkenyl, or substituted or unsubstituted alkynyl; and each of $R^A$, $R^B$, $R^C$, and $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR¹, —N(R¹)₂, —SR¹, —CN, —SCN, —C(=NR¹)R¹, —C(=NR¹)OR¹, —C(=NR¹)N(R¹)₂, —C(=O)R¹, —C(=O)OR¹, —C(=O)N(R¹)₂, —NO₂, —NR¹C(=O)R¹, —NR¹C(=O)OR¹, —NR¹C(=O)N(R¹)₂, —OC(=O)R¹, —OC(=O)OR¹, or —OC(=O)N(R¹)₂, wherein each instance of R¹ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R¹ are joined to form a substituted or unsubstituted heterocyclic or substituted or unsubstituted heteroaryl ring;

provided that the compound is not of the formula:

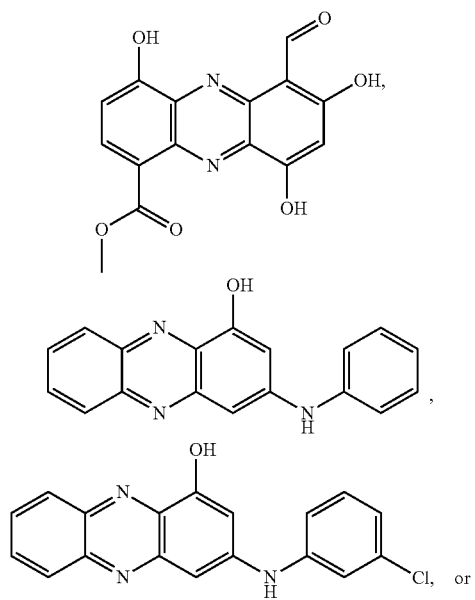

-continued

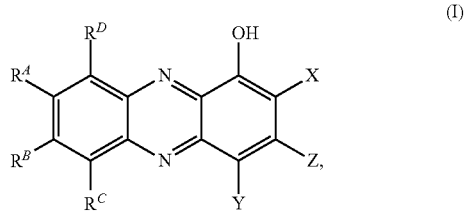

The present invention also provides methods for preventing a microbial infection (e.g., bacterial infection or mycobacterial infection) in a subject in need thereof, the methods comprising administering to the subject in need thereof an effective amount of:

a compound of Formula (I):

(I)

[Structure of Formula (I) showing phenazine core with $R^D$, OH, $R^A$, X, $R^B$, Z, $R^C$, Y substituents]

or a pharmaceutically acceptable salt, solvate, hydrate, polymorph, co-crystal, tautomer, stereoisomer, isotopically labeled compound, or prodrug thereof; or the composition (e.g., pharmaceutical composition) described herein;

wherein:

X is hydrogen, halogen, substituted or unsubstituted alkyl, substituted or unsubstituted alkenyl, or substituted or unsubstituted alkynyl;

Z is halogen, substituted or unsubstituted alkyl, substituted or unsubstituted alkenyl, substituted or unsubstituted alkynyl, —OR³, —N(R⁴)₂, —SR⁵, —CN, —SCN, —C(=NR⁵)R⁵, —C(=NR⁵)OR⁵, —C(=NR⁵)N(R⁵)₂, —C(=O)R⁵, —C(=O)OR⁵, —C(=O)N(R⁵)₂, —NO₂, —NR⁵C(=O)R⁵, —NR⁵C(=O)OR⁵, —NR⁵C(=O)N(R⁵)₂, —OC(=O)R⁵, —OC(=O)OR⁵, or —OC(=O)N(R⁵)₂, wherein each instance of R³, R⁴, and R⁵ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R⁴ are joined to form a substituted or unsubstituted heterocyclic or substituted or unsubstituted heteroaryl ring, or two instances of R⁵ are joined to form a substituted or unsubstituted heterocyclic or substituted or unsubstituted heteroaryl ring;

Y is halogen, substituted or unsubstituted alkyl, substituted or unsubstituted alkenyl, or substituted or unsubstituted alkynyl; and each of $R^A$, $R^B$, $R^C$, and $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^1$, —N(R$^1$)$_2$, —SR$^1$, —CN, —SCN, —C(=NR$^1$)R$^1$, —C(=NR$^1$)OR$^1$, —C(=NR$^1$)N(R$^1$)$_2$, —C(=O)R$^1$, —C(=O)OR$^1$, —C(=O)N(R$^1$)$_2$, —NO$_2$, —NR$^1$C(=O)R$^1$, —NR$^1$C(=O)OR$^1$, —NR$^1$C(=O)N(R$^1$)$_2$, —OC(=O)R$^1$, —OC(=O)OR$^1$, or —OC(=O)N(R$^1$)$_2$, wherein each instance of R$^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^1$ are joined to form a substituted or unsubstituted heterocyclic or substituted or unsubstituted heteroaryl ring;

provided that the compound is not of the formula:

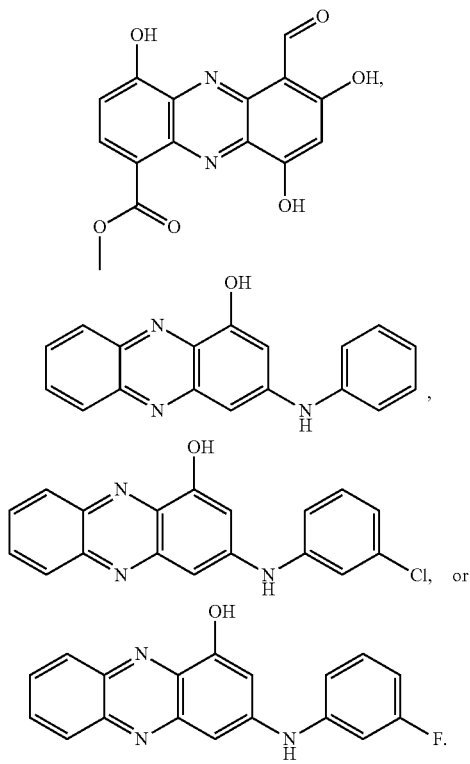

In certain embodiments, the microbial infection is treated by the inventive methods. In certain embodiments, the present invention further provides methods for preventing a microbial infection (e.g., bacterial infection or mycobacterial infection) in a subject in need thereof. In certain embodiments, the microbial infection is prevented by the inventive methods.

In certain embodiments, the subject described herein is an animal. In certain embodiments, the subject is a non-human animal. In certain embodiments, the subject is a mammal. In certain embodiments, the subject is a human. In certain embodiments, the subject is a human aged 18 or older. In certain embodiments, the subject is a human with cystic fibrosis. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent, dog, or non-human primate. In certain embodiments, the subject is a non-human transgenic animal, such as a transgenic mouse or transgenic pig.

In certain embodiments, the methods of the invention include administering to a subject in need thereof an effective amount of a compound of the invention. In certain embodiments, the methods of the invention include administering to a subject in need thereof an effective amount of a pharmaceutical composition of the invention. In certain embodiments, the methods of the invention include administering to a subject in need thereof an effective amount of a compound of Formula (I), or a pharmaceutically acceptable salt thereof, or a pharmaceutical composition thereof. In certain embodiments, the methods of the invention include administering to a subject in need thereof a therapeutically effective amount of a compound of the invention, or a pharmaceutical composition thereof. In certain embodiments, the methods of the invention include administering to a subject in need thereof a prophylactically effective amount of a compound of the invention, or a pharmaceutical composition thereof.

In certain embodiments, the microbial infection that is treated and/or prevented by the inventive methods or using the inventive compounds or pharmaceutical compositions thereof is caused by a multidrug-resistant microorganism and/or a microorganism resistant to methicillin, penicillin, ciprofloxacin, rifampin, vancomycin, daptomycin, linezolid, an antibiotic described herein, or a combination thereof. In certain embodiments, the microbial infection is a microbial respiratory tract infection. In certain embodiments, the microbial infection is microbial pneumonia. In certain embodiments, the microbial infection is microbial sinusitis. In certain embodiments, the microbial infection is tuberculosis (TB). In certain embodiments, the microbial infection is microbial Crohn's disease, paratuberculosis, Buruli ulcer, leprosy, or aquarium granuloma. In certain embodiments, the microbial infection is a microbial gastrointestinal tract infection. In certain embodiments, the microbial infection is microbial diarrhea. In certain embodiments, the microbial infection is a microbial urogenital tract infection. In certain embodiments, the microbial infection is a microbial bloodstream infection. In certain embodiments, the microbial infection is microbial hemolytic uremic syndrome. In certain embodiments, the microbial infection is microbial endocarditis. In certain embodiments, the microbial infection is a microbial ear infection. In certain embodiments, the microbial infection is a microbial skin infection (e.g., microbial acne vulgaris). In certain embodiments, the microbial infection is a microbial oral infection. In certain embodiments, the microbial infection is a microbial dental infection. In certain embodiments, the microbial infection is gingivitis. In certain embodiments, the microbial infection is dental plaque caused by a microorganism. In certain embodiments, the microbial infection is microbial meningitis. In certain embodiments, the microbial infection is a microbial wound or surgical site infection. In certain embodiments, the microbial infection is a microbial burn wound infection. In certain embodiments, the microbial infection is a microbial infection associated with cystic fibrosis. In certain embodiments, the microbial infection is a microbial infection associated with an implanted device. In certain embodiments, the microbial infection is a microbial infection associated with a dental implant. In certain embodiments, the microbial infection is a microbial infection associated with a catheter. In certain embodiments, the microbial infection is a microbial infection associated with a heart valve. In certain embodiments, the microbial infection is a microbial infection associated with an intrauterine device. In certain embodiments, the microbial infection is a microbial infection associated with a joint prosthesis. In certain embodiments, the microbial infection is a bacterial infection. In certain embodiments, the bacterial infection is caused by a Gram-positive bacterium (e.g., a Gram-positive bacterium described herein). In certain embodiments, the bacterial infection is caused by a Gram-negative bacterium (e.g., a Gram-negative bacterium described herein). In certain embodiments, the bacterial infection is caused by a multi-drug-resistant bacterium. In certain embodiments, the bacterial infection is caused by a strain of *Staphylococcus aureus*. In certain embodiments, the bacterial infection is a methicillin-resistant *Staphylococcus aureus* (MRSA)-related infection. In certain embodiments, the bacterial infection is caused by a strain of *Staphylococcus epidermidis* (e.g., MRSE). In certain embodiments, the bacterial infection is an MRSE-related infection. In certain embodiments, the bacterial infection is caused by a strain of *Enterococcus faecium*. In certain embodiments, the bacterial infection is caused by *Acinetobacter baumannii* (*A. baumannii*). In certain embodiments, the microbial infection is a mycobacterial infection. In certain embodiments, the microbial infection is caused by a mycobacterium (e.g., a strain of *Mycobacterium tuberculosis*). In certain embodiments, the microbial infection is caused by an archaeon. In certain embodiments, the microbial infection is caused by a protist. In certain embodiments, the microbial infection is caused by a protozoon. In certain embodiments, the microbial infection is caused by an alga. In certain embodiments, the microbial infection is caused by a fungus. In certain embodiments, the microbial infection is caused by yeast. In certain embodiments, the microbial infection is caused by a mold. In certain embodiments, the microbial infection is caused by a parasite. In certain embodiments, the microbial infection is a microbial infection associated with a biofilm.

Another aspect of the present invention relates to methods of inhibiting the growth of a microorganism using a compound of the invention, or a pharmaceutical composition thereof. In certain embodiments, an inventive method selectively inhibits the growth of a first microorganism (e.g., a microorganism described herein), compared to the inhibition of the growth of a host cell or a second microorganism. In certain embodiments, the growth of a microorganism is inhibited by the inventive methods. In certain embodiments, the growth of a first microorganism is selectively inhibited by the inventive methods, compared to the inhibition of the growth of a host cell or a second microorganism.

Another aspect of the present invention relates to methods of inhibiting the reproduction of a microorganism using a compound of the invention, or a pharmaceutical composition thereof. In certain embodiments, an inventive method selectively inhibits the reproduction of a first microorganism (e.g., a microorganism described herein), compared to the inhibition of the reproduction of a host cell or a second microorganism. In certain embodiments, the reproduction of a microorganism is inhibited by the inventive methods. In certain embodiments, the reproduction of a first microorganism is selectively inhibited by the inventive methods, compared to the inhibition of the reproduction of a host cell or a second microorganism.

Another aspect of the present invention relates to methods of inhibiting the viability of a microorganism using a compound of the invention, or a pharmaceutical composition thereof. In certain embodiments, an inventive method selectively inhibits the viability of a first microorganism (e.g., a microorganism described herein), compared to the inhibition of the viability of a host cell or a second microorganism. In certain embodiments, the viability of a microorganism is inhibited by the inventive methods. In certain embodiments, the viability of a first microorganism is selectively inhibited by the inventive methods, compared to the inhibition of the viability of a host cell or a second microorganism.

Another aspect of the present invention relates to methods of killing a microorganism using a compound of the invention, or a pharmaceutical composition thereof. In certain embodiments, an inventive method selectively kills a first microorganism (e.g., a microorganism described herein), compared to the killing of a host cell or a second microorganism. In certain embodiments, a microorganism is killed by the inventive methods. In certain embodiments, a first microorganism is selectively killed by the inventive methods, compared to the killing of a host cell or a second microorganism.

In certain embodiments, the methods of inhibiting the growth of the microorganism, inhibiting the reproduction of the microorganism, inhibiting the viability of the microorganism, or killing the microorganism comprise contacting the microorganism with an effective amount of:

a compound of Formula (I):

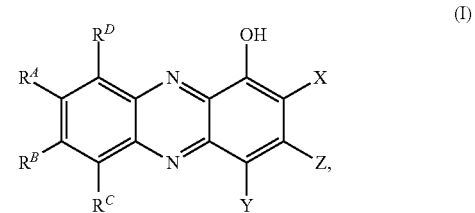

(I)

or a salt (e.g., pharmaceutically acceptable salt), solvate, hydrate, polymorph, co-crystal, tautomer, stereoisomer, isotopically labeled compound, or prodrug thereof; or the composition described herein;

wherein:

X is hydrogen, halogen, substituted or unsubstituted alkyl, substituted or unsubstituted alkenyl, or substituted or unsubstituted alkynyl;

Z is halogen, substituted or unsubstituted alkyl, substituted or unsubstituted alkenyl, substituted or unsubstituted alkynyl, $-OR^3$, $-N(R^4)_2$, $-SR^5$, $-CN$, $-SCN$, $-C(=NR^5)R^5$, $-C(=NR^5)OR^5$, $-C(=NR^5)N(R^5)_2$, $-C(=O)R^5$, $-C(=O)OR^5$, $-C(=O)N(R^5)_2$, $-NO_2$, $-NR^5C(=O)R^5$, $-NR^5C(=O)OR^5$, $-NR^5C(=O)N(R^5)_2$, $-OC(=O)R^5$, $-OC(=O)OR^5$, or $-OC(=O)N(R^5)_2$, wherein each instance of $R^3$, $R^4$, and $R^5$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R⁴ are joined to form a substituted or unsubstituted heterocyclic or substituted or unsubstituted heteroaryl ring, or two instances of R⁵ are joined to form a substituted or unsubstituted heterocyclic or substituted or unsubstituted heteroaryl ring;

Y is halogen, substituted or unsubstituted alkyl, substituted or unsubstituted alkenyl, or substituted or unsubstituted alkynyl; and each of $R^A$, $R^B$, $R^C$, and $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR¹, —N(R¹)₂, —SR¹, —CN, —SCN, —C(=NR¹)R¹, —C(=NR¹)OR¹, —C(=NR¹)N(R¹)₂, —C(=O)R¹, —C(=O)OR¹, —C(=O)N(R¹)₂, —NO₂, —NR¹C(=O)R¹, —NR¹C(=O)OR¹, —NR¹C(=O)N(R¹)₂, —OC(=O)R¹, —OC(=O)OR¹, or —OC(=O)N(R¹)₂, wherein each instance of R¹ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R¹ are joined to form a substituted or unsubstituted heterocyclic or substituted or unsubstituted heteroaryl ring;

provided that the compound is not of the formula:

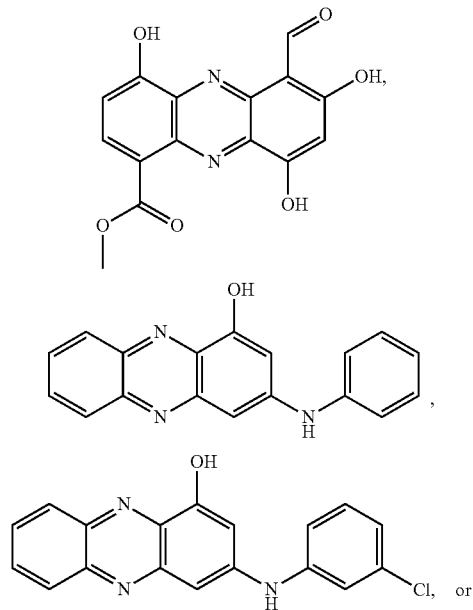

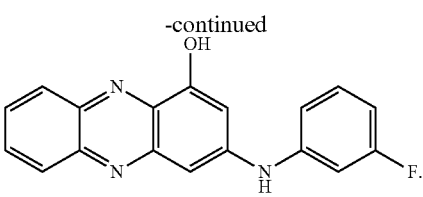

In certain embodiments, the methods of the invention include contacting a microorganism with an effective amount of a compound of the invention. In certain embodiments, the methods of the invention include contacting a microorganism with an effective amount of a composition (e.g., pharmaceutical composition) of the invention. In certain embodiments, the methods of the invention include contacting a microorganism with an effective amount of a compound of Formula (I), or a pharmaceutically acceptable salt thereof, or a pharmaceutical composition thereof. In certain embodiments, the methods of the invention include contacting a microorganism with a therapeutically effective amount of a compound of the invention, or a pharmaceutical composition thereof. In certain embodiments, the methods of the invention include contacting a microorganism with a prophylactically effective amount of a compound of the invention, or a pharmaceutical composition thereof.

In a growth process of a microorganism (e.g., a bacterium), the microorganism may secrete viscous substances to form a biofilm. A biofilm is typically formed on a living or non-living, solid or liquid surface. In certain embodiments, a biofilm is formed on the surface of a biological sample (e.g., a tooth, oral soft tissue, middle ear, gastrointestinal tract, urogenital tract, respiratory tract, or eye). In certain embodiments, a biofilm is formed on the surface of an implanted device (e.g., a dental implant, catheter, heart valve, intrauterine device, or joint prosthesis). In certain embodiments, the biofilm is in vitro. In certain embodiments, the biofilm is in vivo. In certain embodiments, the biofilm described herein comprises a microorganism. In certain embodiments, the biofilm comprises a microorganism (e.g., bacterium). In certain embodiments, the biofilm comprises a strain of *Staphylococcus aureus* (e.g., a methicillin-resistant strain of *Staphylococcus aureus*). In certain embodiments, the biofilm comprises a strain of *Staphylococcus epidermidis* (e.g., a strain of MRSE). Free-floating microorganisms may accumulate on a surface, and the resulting biofilm may grow. In a biofilm, the concentration of microorganisms may be high and/or the resistance of the microorganisms in the biofilm to antimicrobial agents may be high. Antimicrobials may be inactivated or fail to penetrate into the biofilm. Therefore, microbial infections associated with a biofilm (e.g., microbial infections caused by a biofilm) are typically more difficult to treat than microbial infections not associated with a biofilm.

Another aspect of the present invention relates to methods of inhibiting the formation of a biofilm using a compound of the invention, or a pharmaceutical composition thereof. In certain embodiments, the formation of a biofilm is inhibited by the inventive methods.

Another aspect of the present invention relates to methods of inhibiting the growth of a biofilm using a compound of the invention, or a pharmaceutical composition thereof. In certain embodiments, the growth of a biofilm is inhibited by the inventive methods.

Another aspect of the present invention relates to methods of reducing a biofilm using a compound of the invention, or a pharmaceutical composition thereof. In certain embodiments, a biofilm is reduced by the inventive methods, e.g., reduced by at least 10%, at least 20%, at least 30%, at least 50%, at least 70%, at least 90%, at least 99%, at least 99.9%, or at least 99.99%, in terms of the volume of the biofilm. In certain embodiments, a biofilm is reduced by the inventive methods by not more than 10%, not more than 20%, not more than 30%, not more than 50%, not more than 70%, not more than 90%, not more than 99%, not more than 99.9%, or not more than 99.99%, in terms of the volume of the biofilm. In certain embodiments, a biofilm is reduced by the inventive methods by at least 10%, at least 20%, at least 30%, at least 50%, at least 70%, at least 90%, at least 99%, at least 99.9%, or at least 99.99%, in terms of the number of microorganisms (e.g., bacteria) in the biofilm. In certain embodiments, a biofilm is reduced by the inventive methods by not more than 10%, not more than 20%, not more than 30%, not more than 50%, not more than 70%, not more than 90%, not more than 99%, not more than 99.9%, or not more than 99.99%, in terms of the number of microorganisms (e.g., bacteria) in the biofilm.

Another aspect of the present invention relates to methods of clearing a biofilm (e.g., eradicating a biofilm (e.g., reducing the volume of the biofilm by at least 99% and/or killing essentially all (e.g., at least 99%) of the microorganisms (e.g., bacteria) in the biofilm)) using a compound of the invention, or a pharmaceutical composition thereof. In certain embodiments, a biofilm is removed by the inventive methods. In certain embodiments, a biofilm reduced or removed by a method of the invention does not regrow one day, two days, four days, one week, two weeks, three weeks, or one month subsequent to the biofilm being subject to the method.

In certain embodiments, the methods of inhibiting the formation of the biofilm, inhibiting the growth of the biofilm, reducing the biofilm, or clearing the biofilm in the subject comprise administering to the subject an effective amount of:
a compound of Formula (I):

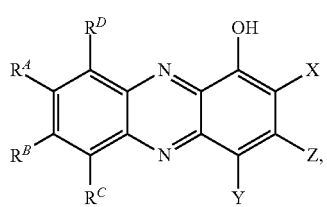

or a pharmaceutically acceptable salt, solvate, hydrate, polymorph, co-crystal, tautomer, stereoisomer, isotopically labeled compound, or prodrug thereof; or
the composition of described herein;
wherein:
X is hydrogen, halogen, substituted or unsubstituted alkyl, substituted or unsubstituted alkenyl, or substituted or unsubstituted alkynyl;
Z is halogen, substituted or unsubstituted alkyl, substituted or unsubstituted alkenyl, substituted or unsubstituted alkynyl, $-OR^3$, $-N(R^4)_2$, $-SR^5$, $-CN$, $-SCN$, $-C(=NR^5)R^5$, $-C(=NR^5)OR^5$, $-C(=NR^5)N(R^5)_2$, $-C(=O)R^5$, $-C(=O)OR^5$, $-C(=O)N(R^5)_2$, $-NO_2$, $-NR^5C(=O)R^5$, $-NR^5C(=O)OR^5$, $-NR^5C(=O)N(R^5)_2$, $-OC(=O)R^5$, $-OC(=O)OR^5$, or $-OC(=O)N(R^5)_2$, wherein each instance of $R^3$, $R^4$, and $R^5$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^4$ are joined to form a substituted or unsubstituted heterocyclic or substituted or unsubstituted heteroaryl ring, or two instances of $R^5$ are joined to form a substituted or unsubstituted heterocyclic or substituted or unsubstituted heteroaryl ring;

Y is halogen, substituted or unsubstituted alkyl, substituted or unsubstituted alkenyl, or substituted or unsubstituted alkynyl; and each of $R^A$, $R^B$, $R^C$, and $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^1$, $-N(R^1)_2$, $-SR^1$, $-CN$, $-SCN$, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, $-NO_2$, $-NR^1C(=O)R^1$, $-NR^1C(=O)OR^1$, $-NR^1C(=O)N(R^1)_2$, $-OC(=O)R^1$, $-OC(=O)OR^1$, or $-OC(=O)N(R^1)_2$, wherein each instance of $R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^1$ are joined to form a substituted or unsubstituted heterocyclic or substituted or unsubstituted heteroaryl ring;

provided that the compound is not of the formula:

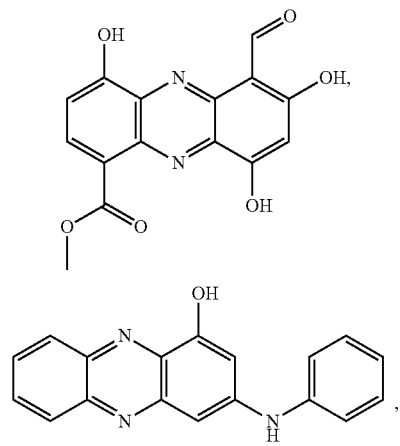

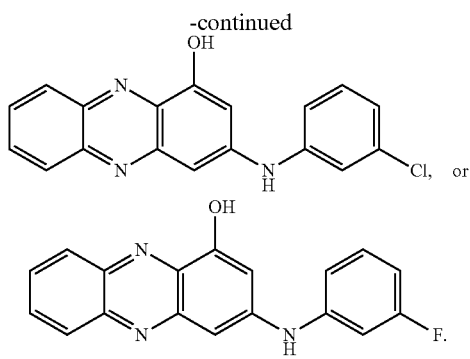

In certain embodiments, the methods of the invention include contacting a biofilm with an effective amount of a compound of the invention. In certain embodiments, the methods of the invention include contacting a biofilm with an effective amount of a pharmaceutical composition of the invention. In certain embodiments, the methods of the invention include contacting a biofilm with an effective amount of a compound of Formula (I), or a pharmaceutically acceptable salt thereof, or a pharmaceutical composition thereof. In certain embodiments, the methods of the invention include contacting a biofilm with a therapeutically effective amount of a compound of the invention, or a pharmaceutical composition thereof. In certain embodiments, the methods of the invention include contacting a biofilm with a prophylactically effective amount of a compound of the invention, or a pharmaceutical composition thereof.

Another aspect of the present invention relates to methods of disinfecting a surface, the methods comprising contacting the surface with an effective amount of:

a compound of Formula (I):

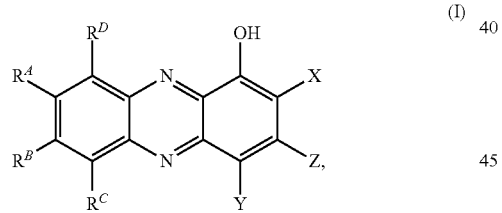

or a pharmaceutically acceptable salt, solvate, hydrate, polymorph, co-crystal, tautomer, stereoisomer, isotopically labeled compound, or prodrug thereof; or the composition (e.g., pharmaceutical composition) described herein;

wherein:

X is hydrogen, halogen, substituted or unsubstituted alkyl, substituted or unsubstituted alkenyl, or substituted or unsubstituted alkynyl;

Z is halogen, substituted or unsubstituted alkyl, substituted or unsubstituted alkenyl, substituted or unsubstituted alkynyl, —OR$^3$, —N(R$^4$)$_2$, —SR$^5$, —CN, —SCN, —C(=NR$^5$)R$^5$, —C(=NR$^5$)OR$^5$, —C(=NR$^5$)N(R$^5$)$_2$, —C(=O)R$^5$, —C(=O)OR$^5$, —C(=O)N(R$^5$)$_2$, —NO$_2$, —NR$^5$C(=O)R$^5$, —NR$^5$C(=O)OR$^5$, —NR$^5$C(=O)N(R$^5$)$_2$, —OC(=O)R$^5$, —OC(=O)OR$^5$, or —OC(=O)N(R$^5$)$_2$, wherein each instance of R$^3$, R$^4$, and R$^5$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^4$ are joined to form a substituted or unsubstituted heterocyclic or substituted or unsubstituted heteroaryl ring, or two instances of R$^5$ are joined to form a substituted or unsubstituted heterocyclic or substituted or unsubstituted heteroaryl ring;

Y is halogen, substituted or unsubstituted alkyl, substituted or unsubstituted alkenyl, or substituted or unsubstituted alkynyl; and each of R$^A$, R$^B$, R$^C$, and R$^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^1$, —N(R$^1$)$_2$, —SR$^1$, —CN, —SCN, —C(=NR$^1$)R$^1$, —C(=NR$^1$)OR$^1$, —C(=NR$^1$)N(R$^1$)$_2$, —C(=O)R$^1$, —C(=O)OR$^1$, —C(=O)N(R$^1$)$_2$, —NO$_2$, —NR$^1$C(=O)R$^1$, —NR$^1$C(=O)OR$^1$, —NR$^1$C(=O)N(R$^1$)$_2$, —OC(=O)R$^1$, —OC(=O)OR$^1$, or —OC(=O)N(R$^1$)$_2$, wherein each instance of R$^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^1$ are joined to form a substituted or unsubstituted heterocyclic or substituted or unsubstituted heteroaryl ring;

provided that the compound is not of the formula:

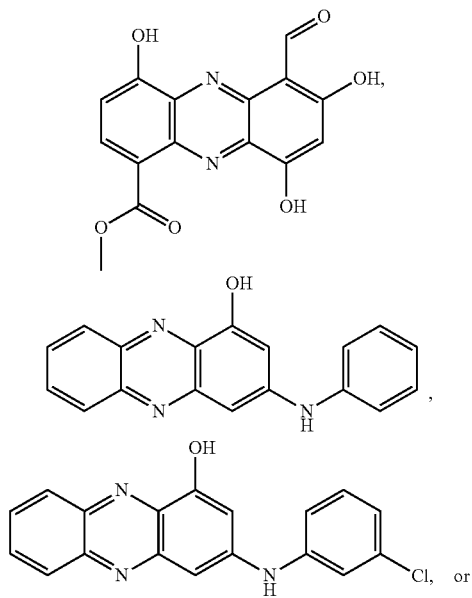

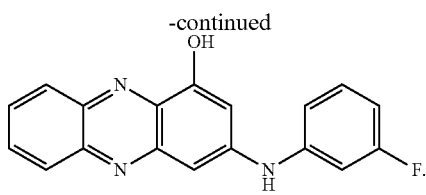

In certain embodiments, the methods of the invention comprise contacting the surface with an effective amount of a compound of the invention. In certain embodiments, the methods of the invention comprise contacting the surface with an effective amount of a composition (e.g., pharmaceutical composition) of the invention. In certain embodiments, the number of viable microorganisms on the surface is reduced after the surface is contacted with the compound or composition. In certain embodiments, the surface is a biological surface, such as skin (e.g., skin of: the hands, feet, arms, legs, face, neck, torso, or cavity (e.g., oral cavity)) of a subject. In certain embodiments, the surface is a non-biological surface (e.g., a surface in a household, industrial, or medical setting, such as a surface of: a kitchen, bathroom, table top, floor, wall, window, utensil, cutlery, crockery, or medical device). A non-biological surface may be a surface of a solid material, such as plastic, wood, bamboo, metal, ceramic, glass, concrete, stone, paper, fabric, or a combination thereof. A non-biological surface may be painted or non-painted, or coated or non-coated. In certain embodiments, the amount of the compound or composition is effective for killing at least 80%, at least 90%, at least 95%, at least 99%, at least 99.9%, or at least 99.99% of the microorganisms on the surface.

In certain embodiments, the microorganism described herein is a bacterium. In certain embodiments, the microorganism is multidrug-resistant. In certain embodiments, the microorganism is resistant to methicillin, penicillin, ciprofloxacin, rifampin, vancomycin, daptomycin, linezolid, or a combination thereof. In certain embodiments, the microorganism is associated with a biofilm (e.g., present in and/or on a biofilm, able to form a biofilm, and/or able to increase the size of a biofilm). In certain embodiments, the bacterium is a Gram-positive bacterium. In certain embodiments, the bacterium is a multidrug-resistant bacterium. In certain embodiments, the bacterium is a *Staphylococcus* species. In certain embodiments, the bacterium is a *Staphylococcus aureus* (*S. aureus*) strain (e.g., ATCC 25923). In certain embodiments, the bacterium is methicillin-resistant *Staphylococcus aureus* (MRSA). In certain embodiments, the bacterium is the methicillin-resistant *Staphylococcus aureus* clinical isolate (MRSA-2, a clinical isolate from a patient treated at Shands Hospital; obtained from the Emerging Pathogens Institute at the University of Florida), such as the methicillin-resistant *Staphylococcus aureus* clinical isolate reported in Abouelhassan et al., Bioorg. Med. Chem. Lett., 2014, 24, 5076. In certain embodiments, the bacterium is a *Staphylococcus epidermidis* (*S. epidermidis*) strain (e.g., ATCC 12228 or ATCC 35984). In certain embodiments, the bacterium is an MRSE strain. In certain embodiments, the bacterium is a *Staphylococcus auricularis, Staphylococcus carnosus, Staphylococcus condimenti, Staphylococcus massiliensis, Staphylococcus piscifermentans, Staphylococcus simulans, Staphylococcus capitis, Staphylococcus caprae, Staphylococcus saccharolyticus, Staphylococcus devriesei, Staphylococcus haemolyticus, Staphylococcus hominis, Staphylococcus chromogenes, Staphylococcus felis, Staphylococcus delphini, Staphylococcus hyicus, Staphylococcus intermedius, Staphylococcus lutrae, Staphylococcus microti, Staphylococcus muscae, Staphylococcus pseudintermedius, Staphylococcus rostri, Staphylococcus schleiferi, Staphylococcus lugdunensis, Staphylococcus arlettae, Staphylococcus cohnii, Staphylococcus equorum, Staphylococcus gallinarum, Staphylococcus kloosii, Staphylococcus leei, Staphylococcus nepalensis, Staphylococcus saprophyticus, Staphylococcus succinus, Staphylococcus xylosus, Staphylococcus fleurettii, Staphylococcus lentus, Staphylococcus sciuri, Staphylococcus stepanovicii, Staphylococcus vitulinus, Staphylococcus simulans, Staphylococcus pasteuri,* or *Staphylococcus warneri* strain. In certain embodiments, the bacterium is a *Streptococcus* species. In certain embodiments, the bacterium is a *Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus mitis, Streptococcus mutans, Streptococcus oralis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans,* or *Streptococcus zooepidemicus* strain. In certain embodiments, the bacterium is a strain of *Streptococcus pneumoniae*. In certain embodiments, the bacterium is an *Enterococcus* species. In certain embodiments, the bacterium is an *Enterococcus avium, Enterococcus durans, Enterococcus faecalis, Enterococcus faecium, Enterococcus gallinarum, Enterococcus hirae,* or *Enterococcus solitarius* strain. In certain embodiments, the bacterium is an *Enterococcus faecium* strain (e.g., a vancomycin-resistant strain of *Enterococcus faecium* (VRE); ATCC 700221). In certain embodiments, the bacterium is a *Listeria* species. In certain embodiments, the bacterium is a *Listeria fleischmannii, Listeria grayi, Listeria innocua, Listeria ivanovii, Listeria marthii, Listeria monocytogenes, Listeria rocourtiae, Listeria seeligeri, Listeria weihenstephanensis,* or *Listeria welshimeri* strain. In certain embodiments, the bacterium is a *Clostridium* species. In certain embodiments, the bacterium is a *Clostridium acetobutylicum, Clostridium argentinense, Clostridium aerotolerans, Clostridium baratii, Clostridium beijerinckii, Clostridium bifermentans, Clostridium botulinum, Clostridium butyricum, Clostridium cadaveris, Clostridium cellulolyticum, Clostridium chauvoei, Clostridium clostridioforme, Clostridium colicanis, Clostridium difficile, Clostridium estertheticum, Clostridium fallax, Clostridium feseri, Clostridium formicaceticum, Clostridium histolyticum, Clostridium innocuum, Clostridium kluyveri, Clostridium ljungdahlii, Clostridium lavalense, Clostridium leptum, Clostridium novyi, Clostridium oedematiens, Clostridium paraputrificum, Clostridium perfringens* (Alias: *Clostridium welchii*), *Clostridium phytofermentans, Clostridium piliforme, Clostridium ragsdalei, Clostridium ramosum, Clostridium scatologenes, Clostridium septicum, Clostridium sordellii, Clostridium sporogenes, Clostridium sticklandii, Clostridium tertium, Clostridium tetani, Clostridium thermocellum, Clostridium thermosaccharolyticum,* or *Clostridium tyrobutyricum* strain. In certain embodiments, the bacterium is a Gram-negative bacterium. In certain embodiments, the bacterium is a bacterium described herein, provided that the bacterium is not a Gram-negative bacterium. In certain embodiments, the Gram-negative bacterium is an *Escherichia* species. In certain embodiments, the Gram-negative bacterium is an *Escherichia coli* (*E. coli*) strain (e.g., ATCC 33475, K-12, CFT073, ATCC 43895). In certain embodiments, the Gram-negative bacterium is an *Escherichia albertii* strain, *Escherichia blattae* strain, *Escherichia fergusonii* strain, *Escherichia hermannii* strain, or *Escherichia vulneris* strain. In certain embodiments, the Gram-negative bacterium is a *Pseudomonas* species. In certain embodiments, the Gram-negative bacterium is a *Pseudomonas aeruginosa* strain. In certain embodiments, the Gram-negative bacterium is a *Pseudomonas alcaligenes* strain, *Pseudomonas anguilliseptica* strain, *Pseudomonas argentinensis* strain, *Pseudomonas borbori* strain, *Pseudomonas citronellolis* strain, *Pseudomonas flavescens* strain, *Pseudomonas mendocina* strain, *Pseudomonas nitroreducens* strain, *Pseudomonas oleovorans* strain, *Pseudomonas pseudoalcaligenes* strain, *Pseudomonas resinovorans* strain, *Pseudomonas straminea* strain, *Pseudomonas chlororaphis* strain, *Pseudomonas fluorescens* strain, *Pseudomonas pertucinogena* strain, *Pseudomonas putida* strain, *Pseudomonas stutzeri* strain, or *Pseudomonas syringae* strain. In certain embodiments, the Gram-negative bacterium is a *Klebsiella* species. In certain embodiments, the Gram-negative bacterium is a *Klebsiella granulomatis* strain, *Klebsiella oxytoca* strain, *Klebsiella pneumoniae* strain, *Klebsiella terrigena* strain, or *Klebsiella planticola* strain. In certain embodiments, the Gram-negative bacterium is a strain of *Klebsiella pneumoniae* (*K. pneumoniae*). In certain embodiments, the Gram-negative bacterium is a *Salmonella* species. In certain embodiments, the Gram-negative bacterium is a *Salmonella bongori* strain or *Salmonella enterica* strain, e.g., *Salmonella typhi*. In certain embodiments, the Gram-negative bacterium is an *Acinetobacter* species. In certain embodiments, the Gram-negative bacterium is an *Acinetobacter baumannii* strain. In certain embodiments, the Gram-negative bacterium is an *Acinetobacter baylyi* strain, *Acinetobacter bouvetii* strain, *Acinetobacter calcoaceticus* strain, *Acinetobacter gerneri* strain, *Acinetobacter grimontii* strain, *Acinetobacter haemolyticus* strain, *Acinetobacter johnsonii* strain, *Acinetobacter junii* strain, *Acinetobacter lwoffii* strain, *Acinetobacter parvus* strain, *Acinetobacter pittii* strain, *Acinetobacter radioresistens* strain, *Acinetobacter schindleri* strain, *Acinetobacter tandoii* strain, *Acinetobacter tjernbergiae* strain, *Acinetobacter towneri* strain, *Acinetobacter ursingii* strain, or *Acinetobacter gyllenbergii* strain. In certain embodiments, the microorganism is a mycobacterium. In certain embodiments, the microorganism is a strain of *Mycobacterium tuberculosis*.

In certain embodiments, the microorganism is a strain of: *Mycobacterium bovis*, *Mycobacterium bovis* BCG, *Mycobacterium africanum*, *Mycobacterium canetti*, *Mycobacterium caprae*, *Mycobacterium microti*, *Mycobacterium Pinnipedii*, *Mycobacterium avium*, *Mycobacterium avium* paratuberculosis, *Mycobacterium avium silvaticum*, *Mycobacterium avium hominissuis*, *Mycobacterium colombiense*, *Mycobacterium indicus pranii*, *Mycobacterium gastri*, *Mycobacterium kansasii*, *Mycobacterium hiberniae*, *Mycobacterium nonchromogenicum*, *Mycobacterium terrae*, *Mycobacterium triviale*, *Mycobacterium ulcerans*, *Mycobacterium pseudoshottsii*, *Mycobacterium shottsii*, *Mycobacterium triplex*, *Mycobacterium genavense*, *Mycobacterium florentinum*, *Mycobacterium lentiflavum*, *Mycobacterium palustre*, *Mycobacterium kubicae*, *Mycobacterium parascrofulaceum*, *Mycobacterium heidelbergense*, *Mycobacterium interjectum*, *Mycobacterium simiae*, *Mycobacterium bohemicum*, *Mycobacterium botniense*, *Mycobacterium branderi*, *Mycobacterium celatum*, *Mycobacterium chimaera*, *Mycobacterium conspicuum*, *Mycobacterium cookii*, *Mycobacterium doricum*, *Mycobacterium farcinogenes*, *Mycobacterium haemophilum*, *Mycobacterium heckeshornense*, *Mycobacterium intracellulare*, *Mycobacterium lacus*, *Mycobacterium leprae*, *Mycobacterium lepraemurium*, *Mycobacterium lepromatosis*, *Mycobacterium malmoense*, *Mycobacterium marinum*, *Mycobacterium monacense*, *Mycobacterium montefiorense*, *Mycobacterium murale*, *Mycobacterium nebraskense*, *Mycobacterium saskatchewanense*, *Mycobacterium scrofulaceum*, *Mycobacterium shimoidei*, *Mycobacterium szulgai*, *Mycobacterium tusciae*, *Mycobacterium xenopi*, *Mycobacterium yongonense*, *Mycobacterium intermedium*, *Mycobacterium abscessus*, *Mycobacterium chelonae*, *Mycobacterium bolletii*, *Mycobacterium fortuitum*, *Mycobacterium fortuitum* subsp. *acetamidolyticum*, *Mycobacterium boenickei*, *Mycobacterium peregrinum*, *Mycobacterium porcinum*, *Mycobacterium senegalense*, *Mycobacterium septicum*, *Mycobacterium neworleansense*, *Mycobacterium houstonense*, *Mycobacterium mucogenicum*, *Mycobacterium mageritense*, *Mycobacterium brisbanense*, *Mycobacterium cosmeticum*, *Mycobacterium parafortuitum*, *Mycobacterium austroafricanum*, *Mycobacterium diernhoferi*, *Mycobacterium hodleri*, *Mycobacterium neoaurum*, *Mycobacterium frederiksbergense*, *Mycobacterium aurum*, *Mycobacterium vaccae*, *Mycobacterium chitae*, *Mycobacterium fallax*, *Mycobacterium confluentis*, *Mycobacterium flavescens*, *Mycobacterium madagascariense*, *Mycobacterium phlei*, *Mycobacterium smegmatis Mycobacterium goodii*, *Mycobacterium wolinskyi*, *Mycobacterium thermoresistibile*, *Mycobacterium gadium*, *Mycobacterium komossense*, *Mycobacterium obuense*, *Mycobacterium sphagni*, *Mycobacterium agri*, *Mycobacterium aichiense*, *Mycobacterium alvei*, *Mycobacterium arupense*, *Mycobacterium brumae*, *Mycobacterium canariasense*, *Mycobacterium chubuense*, *Mycobacterium conceptionense*, *Mycobacterium duvalii*, *Mycobacterium elephantis*, *Mycobacterium gilvum*, *Mycobacterium hassiacum*, *Mycobacterium holsaticum*, *Mycobacterium immunogenum*, *Mycobacterium massiliense*, *Mycobacterium moriokaense*, *Mycobacterium psychrotolerans*, *Mycobacterium pyrenivorans*, *Mycobacterium vanbaalenii*, *Mycobacterium pulveris*, *Mycobacterium arosiense*, *Mycobacterium aubagnense*, *Mycobacterium caprae*, *Mycobacterium chlorophenolicum*, *Mycobacterium fluoroanthenivorans*, *Mycobacterium kumamotonense*, *Mycobacterium novocastrense*, *Mycobacterium parmense*, *Mycobacterium phocaicum*, *Mycobacterium poriferae*, *Mycobacterium rhodesiae*, *Mycobacterium seoulense*, or *Mycobacterium tokaiense*.

In certain embodiments, the microorganism described herein is an archaeon. In certain embodiments, the microorganism is a protist. In certain embodiments, the microorganism is a protozoon. In certain embodiments, the microorganism is an alga. In certain embodiments, the microorganism is a fungus. In certain embodiments, the microorganism is yeast. In certain embodiments, the microorganism is a mold. In certain embodiments, the microorganism is a parasite.

In certain embodiments, the microorganism described herein is in vitro. In certain embodiments, the microorganism is in vivo.

In certain embodiments, a method of the invention is an in vitro method. In certain embodiments, a method of the invention is an in vivo method.

In another aspect, the present invention provides uses of the compounds, compositions, and pharmaceutical compositions of the invention for manufacturing a medicament for treating a microbial infection (e.g., bacterial infection or mycobacterial infection).

In another aspect, the present invention provides uses of the compounds, compositions, and pharmaceutical compositions of the invention for manufacturing a medicament for preventing a microbial infection (e.g., bacterial infection or mycobacterial infection).

In another aspect, the present invention provides the compounds, compositions, and pharmaceutical compositions of the invention for use in treating a microbial infection (e.g., bacterial infection or mycobacterial infection).

3-position of this scaffold. We came across an interesting method reported by Wróbel and co-workers utilizing aniline starting materials to access N-aryl-2-nitrosoaniline intermediates (e.g. 14, Scheme 1) which were then cyclized to phenazines upon treatment with silylating agent N,O-bis(trimethylsilyl)acetamide (BSA) in N,N-dimethylformamide.[44,45] In Wróbel's approach, 3-chloro-1-methoxyphenazines (15, R=H) were accessed and we envisioned this as an entry point to investigate novel 3-substituted HPs (e.g. 16).

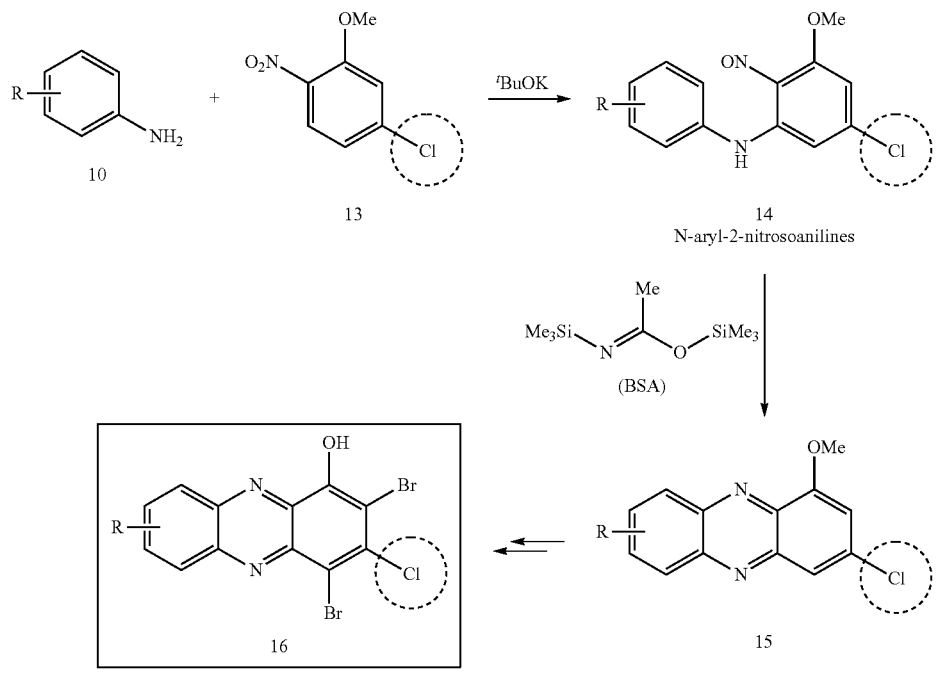

Scheme 1. Utilization of N-aryl-2-nitrosoaniline intermediates for the synthesis of new HPs In another aspect, the present invention provides the compounds, compositions, and pharmaceutical compositions of the invention for use in preventing a microbial infection (e.g., bacterial infection or mycobacterial infection).

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope. A compound described herein may be referred to by using two or more different compound numbers. A compound described herein may be tested two or more times under the same or different conditions for determining a property and, therefore, may show different values of the property.

Example 1. Design and Synthesis of New Halogenated Phenazines Using a Modular Route Our previous efforts to develop HP agents have not included synthetic chemistry that enables exploration at the During the course of these investigations 10 diverse, commercially available anilines 10 were reacted with potassium tert-butoxide ($^t$BuOK) in the presence of 2-nitro-5-chloroanisole 13 to yield N-aryl-2-nitrosoaniline intermediates (Scheme 2). The corresponding N-aryl-2-nitrosoaniline intermediates were each taken on crude and immediately treated with BSA to yield diverse 3-chloro-1-methoxyphenazines 15. This pathway proved to be fruitful as all 10 aniline starting materials were transformed to target phenazines in 34-82% yield (average yield=66%) using this synthetic approach. Select N-aryl-2-nitrosoanilines were confirmed through MS analysis during these investigations, however, they were not fully characterized. Following synthesis of the phenazine nucleus (e.g., 16), each 1-methoxyphenazine was subjected to (1) boron tribromide (BBr$_3$) demethylation to the corresponding 1-hydroxyphenazine (18-27, average yield=98%), and (2) bromination using N-bromosuccinimide (NBS) to generate target HP analogues c28-37, average yield=59%).

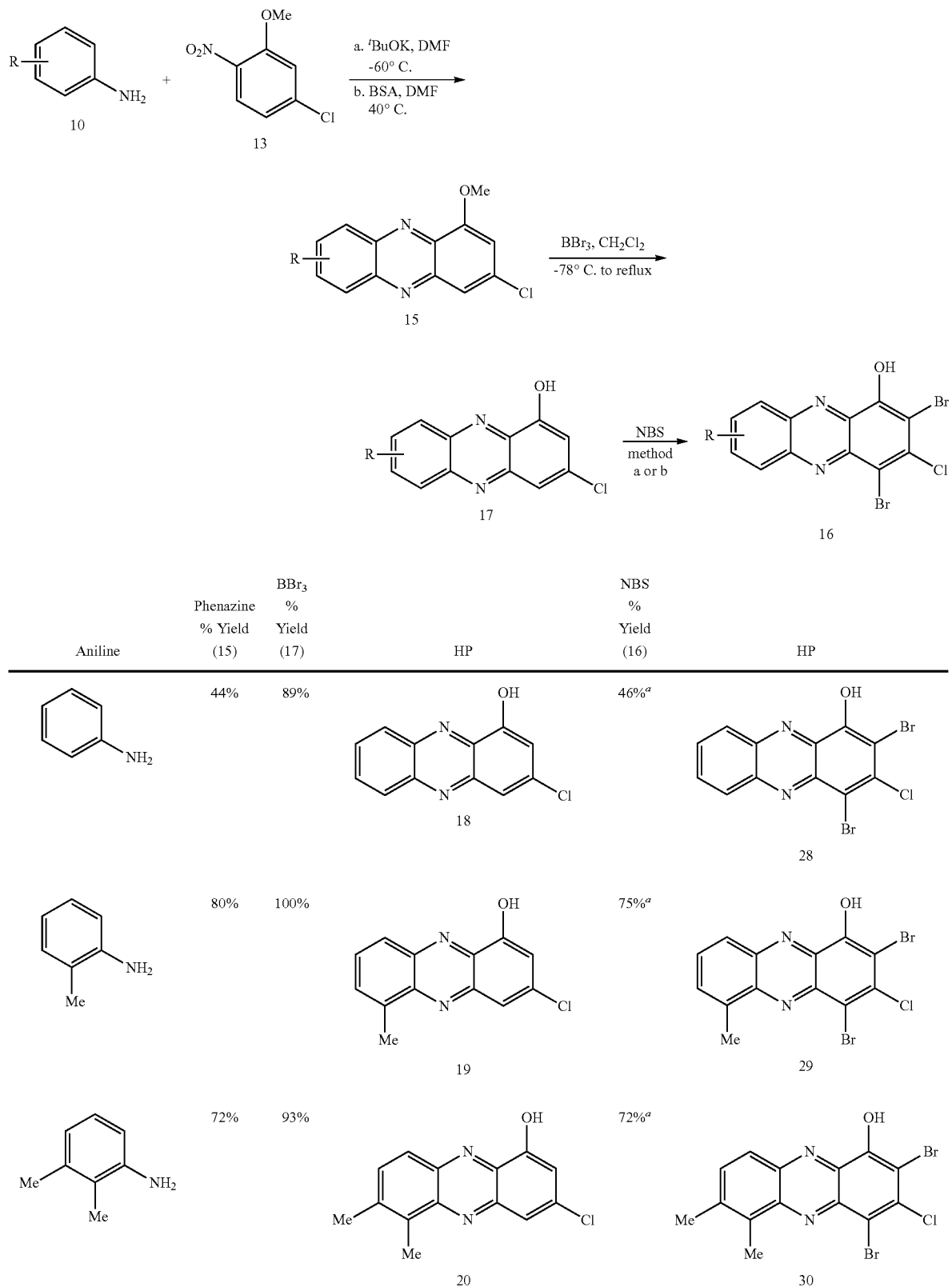
Scheme 2. Modular synthesis of 3-substituted HPs from diverse anilines 10 and 2-nitro-5-chloroanisole 13

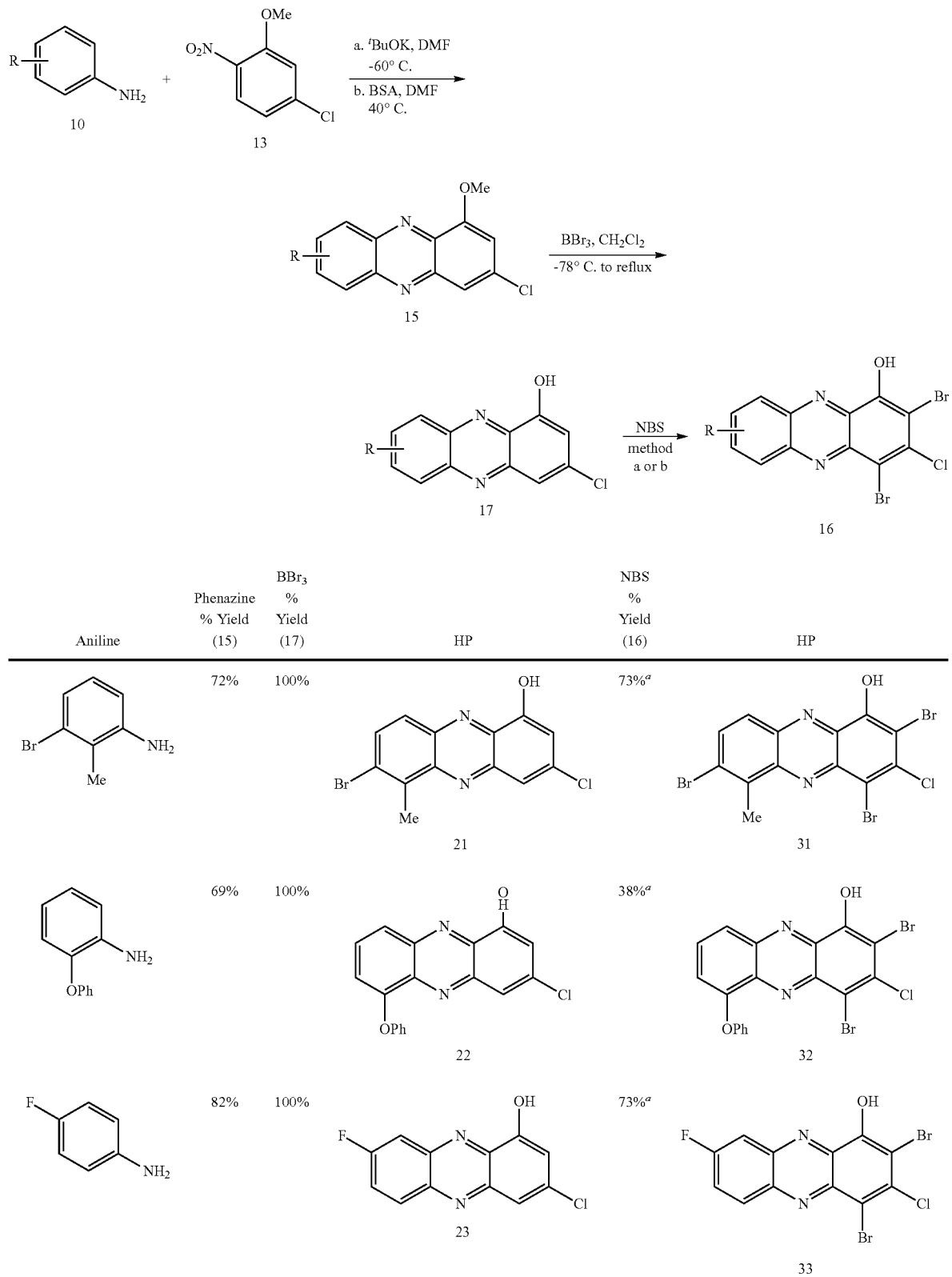
Scheme 2. Modular synthesis of 3-substituted HPs from diverse anilines 10 and 2-nitro-5-chloroanisole 13

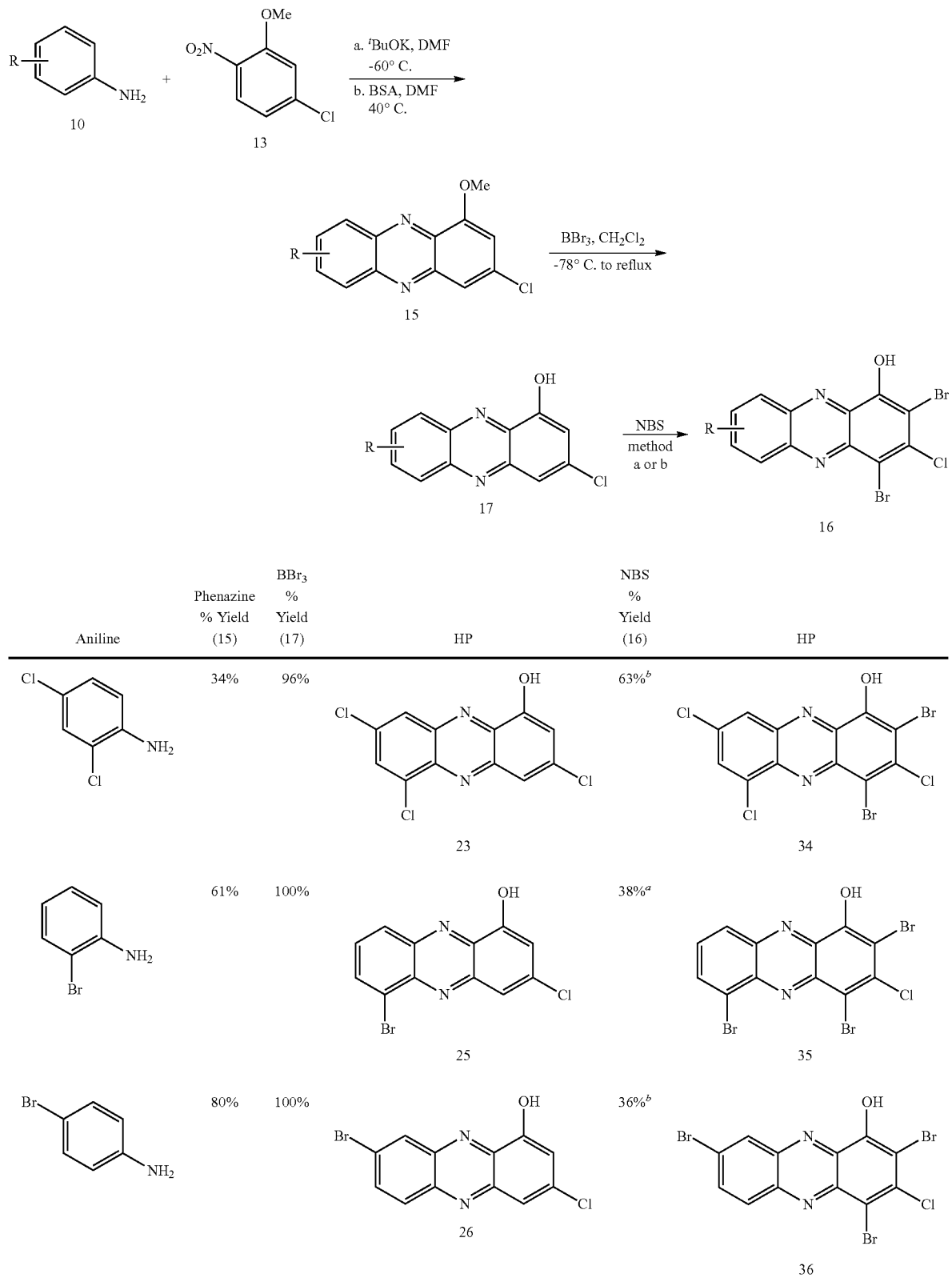

Scheme 2. Modular synthesis of 3-substituted HPs from diverse anilines 10 and 2-nitro-5-chloroanisole 13

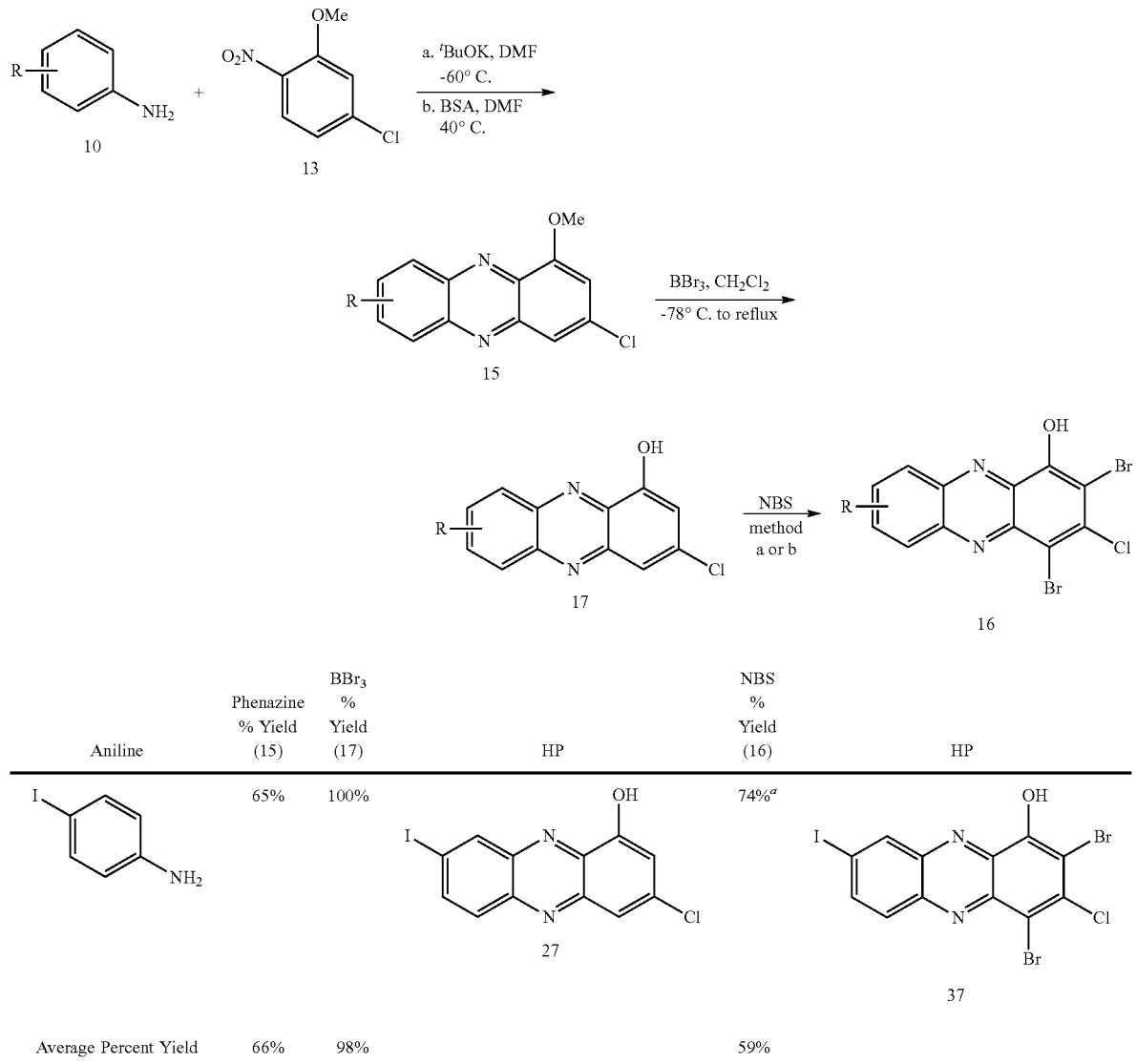

Note:
[a] NBS, CH$_2$Cl$_2$, rt.
[b] NBS, PhMe, 50° C.
NBS: N-bromosuccinimide.

In addition to accessing 3-chloro-HP analogues 18-37, we utilized the chlorine atom as a synthetic handle in S$_N$Ar reactions with three thiol nucleophiles to generate 3-thiolated HP analogues 45-47. During these studies, thiols were reacted with 3-chlorophenazine compounds 19 and 38 to yield the corresponding 3-thiolated phenazine 39-44 (Scheme 3). This reaction working well with potassium carbonate (K$_2$CO$_3$) in N,N-dimethylformamide (DMF) under oil bath heating for 7 days. We found microwave conditions allowed the desired S$_N$Ar reaction to occur in 1 to 3.5 minutes with good yields (47-100%, Scheme 3A). The 3-methoxy group of phenazine 38 was labile in the presence of the thiol nucleophile under these reaction conditions, yielding a mixture of 1-methoxy and 1-hydroxyphenazine (from demethylation) products that were readily separated via column chromatography. We also performed the S$_N$Ar reaction on 1-hydroxy-3-chloro-6-methylphenazine 19 to yield the desired 3-thiolated products in 75-89% yields (Scheme 3A, entry 2 & 5). Each of the 3-thiol-1-hydroxyphenazines (42-44) were then subjected to NBS bromination to yield target 3-thiolated HP analogues 45-47 in 27-73% yield (Scheme 3B).

Scheme 3. Chemical synthesis of 3-thiolated HPs synthesized via nucleophilic aromatic substitution. Method A: NBS, CH$_2$Cl$_2$, rt. Method B: NBS, PhMe, 50° C.

A) Nucleophilic Aromatic Substitution to Thiol Derivatives

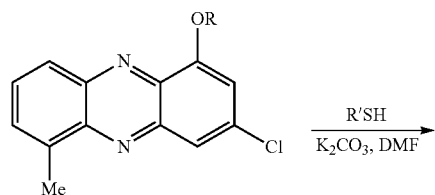

19. R = H
38. R = Me $\xrightarrow{\text{R'SH}}_{\text{K}_2\text{CO}_3,\text{ DMF}}$

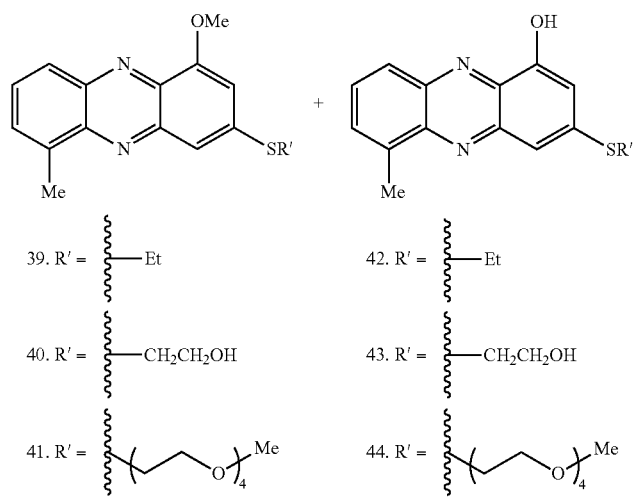

39. R' = —Et
40. R' = —CH$_2$CH$_2$OH
41. R' = —(CH$_2$CH$_2$O)$_4$Me

42. R' = —Et
43. R' = —CH$_2$CH$_2$OH
44. R' = —(CH$_2$CH$_2$O)$_4$Me

| Entry | —R | Thiol | Base | T (° C.) | Heat | Time (min/d) | —SR' | A (%) | B (%) | Combined Yield (%) |
|---|---|---|---|---|---|---|---|---|---|---|
| 1 | —Me | EtSH | K$_2$CO$_3$ | 85 | oil bath | 7 d | —SEt | 31 | 37 | 68 |
| 2 | —H | EtSH | K$_2$CO$_3$ | 200 | MW | 1 min | —SEt | — | 89 | 89 |
| 3 | —Me | HSCH$_2$CH$_2$OH | K$_2$CO$_3$ | 85 | oil bath | 7 d | —SCH$_2$CH$_2$OH | 52 | 17 | 69 |
| 4 | —Me | HSCH$_2$CH$_2$OH | K$_2$CO$_3$ | 200 | MW | 2.5 min | —SCH$_2$CH$_2$OH | 28 | 19 | 47 |
| 5 | —H | HSCH$_2$CH$_2$OH | K$_2$CO$_3$ | 200 | MW | 1 min | —SCH$_2$CH$_2$OH | — | 75 | 75 |
| 6 | —Me | HS(CH$_2$CH$_2$O)$_4$Me | K$_2$CO$_3$ | 200 | MW | 3.5 min | —S(CH$_2$CH$_2$O)$_4$Me | 82 | 18 | 100 |

Scheme 3. Chemical synthesis of 3-thiolated HPs synthesized via nucleophilic aromatic substitution. Method A: NBS, CH$_2$Cl$_2$, rt. Method B: NBS, PhMe, 50° C.

B) Synthesis of 3-Thiol HP Analogues

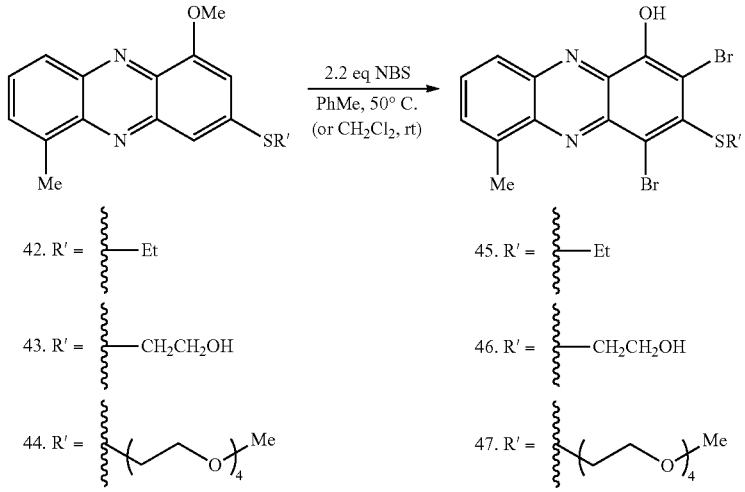

Example 2. In Vitro Antibacterial Studies

We evaluated the new series of 23 HP analogues functionalized at the 3-position in antibacterial assays against a panel of pathogens, including several antibiotic-resistant strains (methicillin-resistant *S. aureus* strains MRSA-1707, MRSA-44; methicillin-resistant *S. epidermidis* MRSE 35984; vancomycin-resistant *Enterococcus faecium* VRE 700221, *Enterococcus faecalis* OG1RF; *Mycobacterium tuberculosis*, Mtb strains H37Ra and CDC1551). These new HPs were categorized into three sub-series to explore and define new structure-activity relationships regarding the HP scaffold, including sub-series: (A) 3-chloro-1-hydroxyphenazines (10 non-brominated HP analogues, 18-27), (B) 2,4-dibromo-3-chloro-1-hydroxyphenazines (10 dibrominated HPs, 28-37), and (C) 2,4-dibromo-3-thio-1-hydroxyphenazines (3 thiolated HPs, 45-47). Each of the three HP sub-series produced active, sub-micromolar potent antibacterial agents against MRSA strains while demonstrating outstanding activity profiles against all bacterial pathogens investigated (Table 1).

This was the first time that we observed potent antibacterial activities regarding HP analogues not containing both bromine atoms at the 2- and 4-position of the HP scaffold, suggesting the 3-chlorine atom dramatically impacts the SAR profile of these agents. Analogue 21 (sub-series A) demonstrated potent activities against *Staphylococcus* strains MRSA-1707, MRSA-44 and MRSE 35984 (MIC=0.30-0.78 µM, Table 1) while demonstrating good antibacterial potency against the other pathogens in the panel (VRE 700221, MIC=1.17 µM; *E. faecalis* OG1RF, MIC=2.35 µM; Mtb H37Ra, MIC=6.25 µM; Mtb CDC1551, MIC=3.27 µM).

Figure 4:
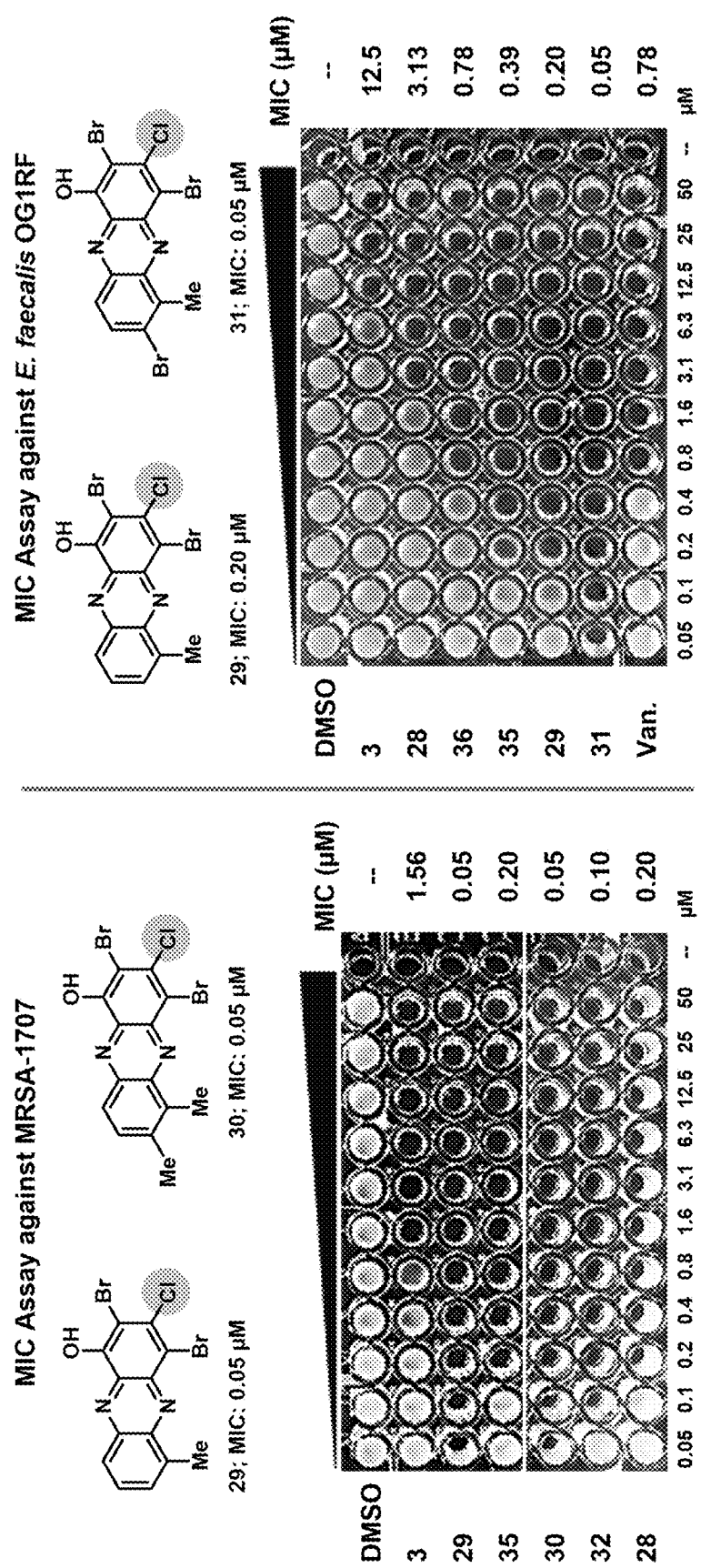
FIG. 4 shows MIC assay results focused on select 3-chloro HP analogues against MRSA-1707 and *E. faecalis* OG1RF. "Van." denotes vancomycin.

The 2,4-dibromo-3-chloro-1-hydroxyphenazine sub-series (B, 10 analogues; Table 1) demonstrated potency against the panel of pathogenic bacteria. As an overview of sub-series B activities, seven HPs demonstrated MIC=0.08-0.30 µM against MRSA-1707 (vancomycin, MIC=0.39 µM; comparator), six HPs reported MIC=0.08-0.20 µM against MRSA-44 (vancomycin, MIC=0.39 µM), eight HPs gave MIC=0.05-0.30 µM against MRSE 35984 (vancomycin, MIC=0.78 µM), seven HPs showed MIC=0.05-0.30 µM against VRE 700221 (vancomycin, MIC>100 µM), five HPs proved MIC=0.08-0.39 µM against *E. faecalis* OG1RF (vancomycin, MIC=0.78 µM). HPs 29, 30, 32, 34 and 35 each recorded sub-micromolar MICs against all Gram-positive strains in the panel (see representative MIC assays, FIG. 4). Select analogues from sub-series B were also evaluated against *M. tuberculosis* strains and found to have good to excellent anti-TB activities, including HPs 29 (H37Ra, MIC=6.25 µM; CDC1551, MIC=1.59 µM), 31 (CDC1551, MIC=0.88 µM), 32 (H37Ra, MIC=3.13 µM; CDC1551, MIC=3.01 µM), and 34 (H37Ra, MIC=6.25 µM; CDC1551, MIC=0.80 µM). In addition, HP 29 displayed excellent antibacterial activity against *Streptococcus pneumoniae* 6303 (MIC=0.50 µM), which is the first time we have shown HP activity against this pathogen.

In addition to HPs bearing a chlorine atom in the 3-position (sub-series A and B), three 3-thiol HP analogues were tested for antibacterial activities. We also wanted to utilize the S$_N$Ar chemistry to explore water-solubilizing side chains (e.g., PEG in HP 47). We found HP 45 bearing an ethyl thiol moiety to have potent antibacterial activities against all Gram-positive strains tested (MRSA, MIC=0.30 µM; MRSE 35984, MIC=0.30 µM; VRE 700221, MIC=0.39 µM). The two 3-thiol HP analogues aimed at improving water solubility (HP 46 bearing a 2-hydroxyethyl thiol moiety at the 3-position; HP 47 containing a four PEG unit thiol at the 3-position) demonstrated significant reductions in antibacterial activities (MICs=2.35-12.5 µM against MRSA, MRSE, VRE; Table 1).

TABLE 1

Summary of MIC values obtained during antibacterial assessment for 3-functionalized HP analogues and comparator compounds, including several antibiotics. All MIC values are reported in micromolar (µM) concentrations.

| Compound | MRSA-1707 | MRSA-44 | MRSE 35984 | VRE 700221 |
|---|---|---|---|---|
| 1 | 3.13 | 3.13 | 3.13 | 6.25 |
| 3 | 1.56[b] | 1.56[b] | 2.35[a] | 4.69[a] |
| 18 | 25 | — | 18.8[a] | >50 |

TABLE 1-continued

Summary of MIC values obtained during antibacterial assessment for 3-functionalized HP analogues and comparator compounds, including several antibiotics. All MIC values are reported in micromolar (μM) concentrations.

| | | | | |
|---|---|---|---|---|
| 19 | 1.56 | 1.56 | 2.35$^a$ | 3.13 |
| 20 | 2.35$^a$ | 2.35$^a$ | 2.35$^a$ | 3.13 |
| 21 | 0.30$^a$ | 0.30$^a$ | 0.78 | 1.17$^a$ |
| 22 | 3.13 | 3.13 | 3.13 | 4.69$^a$ |
| 23 | 6.25 | — | 18.8$^a$ | 18.8$^a$ |
| 24 | 0.30$^a$ | 0.30$^a$ | 1.17$^a$ | 2.35$^a$ |
| 25 | 4.69$^a$ | 9.38$^a$ | 18.8$^a$ | 18.8$^a$ |
| 26 | 9.38$^a$ | — | >50 | >50 |
| 27 | 0.78 | 1.56 | 3.13 | 3.13 |
| 28 | 0.15$^a$ | 0.59$^a$ | 0.59$^a$ | 1.17$^a$ |
| 29 | 0.08$^a$ | 0.08$^a$ | 0.08$^a$ | 0.10 |
| 30 | 0.08$^a$ | 0.08$^a$ | ≤0.05$^c$ | 0.08$^a$ |
| 31 | 0.59$^a$ | 1.17$^a$ | 0.10 | ≤0.05$^c$ |
| 32 | 0.15$^a$ | 0.10 | 0.20 | 0.15$^a$ |
| 33 | 0.15$^a$ | 0.20 | 0.78 | 0.78 |
| 34 | 0.59$^a$ | 0.15$^a$ | ≤0.05$^c$ | 0.08$^a$ |
| 35 | 0.30$^a$ | 0.20 | 0.10 | 0.15$^a$ |
| 36 | 0.59$^a$ | 1.56 | 0.10 | 0.30$^a$ |
| 37 | 0.15$^a$ | 0.78 | 0.30$^a$ | 0.59$^a$ |
| 45 | 0.30$^a$ | 0.30$^a$ | 0.30$^a$ | 0.39 |
| 46 | 6.25 | 6.25 | 4.69$^a$ | 12.5 |
| 47 | 2.35$^a$ | 4.69$^a$ | 2.35$^a$ | 3.13 |
| 150 | 0.10 | | 0.30$^a$ | 0.78 |
| 48 (1-OHP) | 50 | 50 | 37.5$^a$ | >50 |
| 49 (QAC-10) | 4.69$^a$ | 2.35$^a$ | 2.35$^a$ | 2.35$^a$ |
| EDTA | 25 | 125 | — | — |
| TPEN | 46.9$^a$ | 46.9$^a$ | — | — |
| Vancomycin | 0.39 | — | 0.78 | >100 |
| Daptomycin | 3.13 | — | — | — |
| Linezolid | 12.5 | — | — | — |
| Streptomycin | — | — | — | — |

| Compound | E. faecalis OG1RF | S. pneumoniae 6303 | Mtb H37Ra | Mtb CDC1551 |
|---|---|---|---|---|
| 1 | 18.8$^a$ | — | — | — |
| 3 | 12.5$^b$ | — | 25 | 13.7 |

TABLE 1-continued

Summary of MIC values obtained during antibacterial assessment for 3-functionalized HP analogues and comparator compounds, including several antibiotics. All MIC values are reported in micromolar (μM) concentrations.

| | | | | |
|---|---|---|---|---|
| 28 | 3.13 | — | 6.25 | 4.37 |
| 29 | 0.30$^a$ | 0.50 | 6.25 | 1.59 |
| 30 | 0.20 | — | — | 3.62 |
| 31 | 0.08$^a$ | — | — | 0.88 |
| 32 | 0.78 | — | 3.13 | 3.01 |
| 33 | 1.17$^a$ | — | — | 1.71 |
| 34 | 0.30$^a$ | — | 6.25 | 0.80 |
| 35 | 0.39 | — | — | 3.91 |
| 36 | 0.78 | — | — | — |
| 37 | 1.56 | — | — | — |
| 45 | 0.78 | — | — | 1.69 |
| 46 | — | — | — | — |
| 47 | — | — | — | — |
| 48 (1-OHP) | >50 | — | — | — |
| 49 (QAC-10) | 3.13 | — | — | — |
| EDTA | 500 | — | — | — |
| TPEN | 46.9$^a$ | — | — | — |
| Vancomycin | 0.78 | — | — | — |
| Daptomycin | — | — | — | — |
| Linezolid | — | — | — | — |
| Streptomycin | — | — | 1.32 | — |

For Table 1: $^a$Midpoint of a 2-fold range in observed MIC values. $^b$Midpoint of a 4-fold range in observed MIC values. $^c$Lowest test concentration. Test range was 0.05-50 μM for all HPs and higher (e.g., 100 μM) for comparators. EDTA and TPEN are metal-binding agent comparators. Each MIC was determined from three to nine independent experiments.

TABLE 4

Summary of MIC assays against MRSA clinical isolates. All MIC values are reported in micromolar (μM) concentrations.

| Compound | MRSA-1707 | MRSA 1 | MRSA 2 | S. aureus 129 | S. aureus 147 | S. aureus 138 | S. aureus 156 |
|---|---|---|---|---|---|---|---|
| 3 | 1.56$^b$ | 1.25 | 1.88$^a$ | 1.88$^a$ | 1.88$^a$ | 2.5 | 1.25 |
| 29 | 0.08$^a$ | 0.06$^a$ | 0.12$^a$ | 0.12$^a$ | 0.12$^a$ | 0.08 | 0.08 |
| 34 | 0.59$^a$ | 1.25 | 0.94 | 0.63 | 0.47$^a$ | 0.94$^a$ | 0.47$^a$ |
| 45 | 0.30$^a$ | 0.31 | 0.63 | 0.47$^a$ | 0.47$^a$ | 0.47$^a$ | 0.47$^a$ |
| Vancomycin | 0.39 | 0.39 | 0.39 | 0.39 | 0.59$^a$ | 0.39 | 0.39 |
| Methicillin | 18.8$^a$ | 37.5$^a$ | >100 | 37.5$^a$ | 6.25 | 37.5$^a$ | 37.5$^a$ |
| Ciprofloxacin | 0.59$^a$ | 0.78 | >100 | >100 | 1.17$^a$ | >100 | 0.78$^b$ |

TABLE 1-continued

Summary of MIC values obtained during antibacterial assessment for 3-functionalized HP analogues and comparator compounds, including several antibiotics. All MIC values are reported in micromolar (μM) concentrations.

| | | | | |
|---|---|---|---|---|
| 18 | — | — | — | — |
| 19 | — | — | — | — |
| 20 | 12.5 | — | — | — |
| 21 | 2.35$^a$ | — | 6.25 | 3.27 |
| 22 | — | — | — | — |
| 23 | — | — | — | — |
| 24 | 9.38$^a$ | — | 3.13 | 2.31 |
| 25 | — | — | — | — |
| 26 | — | — | — | — |
| 27 | — | — | — | — |

For Table 4: All MIC values were recorded from a minimum of three independent biological assays. $^a$=midpoint of a 2-fold range in observed MIC values. $^b$=midpoint of a 4-fold range in observed MIC values. For these MIC assays, HPs were tested at a range of 0.01-10 μM, while antibiotics were tested at a range of 0.1-100 μM. Clinical isolates MRSA 1, MRSA 2, S. aureus 129, S. aureus 147, S. aureus 138 and S. aureus 156 were obtained from the Emerging Pathogens Institute (EPI) at the University of Florida and isolated from patients treated at UF Health Shands Hospital (Gainesville, FL). Methicillin has an MIC=0.78 μM against S. aureus strain ATCC 29213, which is susceptible to this antibiotic. MRSA-1707 was obtained from ATCC (MRSA strain BAA-1707) and included in this table as a comparator.

Example 3. Cytotoxicity Assessment

Following antibacterial investigations, we evaluated a select panel of active HP analogues against multiple mammalian cell types to determine cytotoxicity and bacterial targeting. From this series, 12 new HPs and parent HP 3 were evaluated against mammalian cell lines, including: (1) three non-brominated 3-chloro HPs (sub-series A; 21, 24, 27), (2) eight 2,4-dibromo-3-chloro HPs (sub-series B; 28-35), and (3) one 2,4-dibromo-3-thiol HP (sub-series C; 45). The cell lines used to determine cytotoxicity of HPs included: HeLa (cervical cancer cell line; 24-h LDH release assay[46], HPs were evaluated at 25, 50 and 100 µM), J774 MΦ (macrophages; 24-h Alamar Blue assay[47], HPs tested in 2-fold dilutions up to 200 µM), HepG2 (hepatocellular carcinoma; 24-h Alamar Blue assay, HPs tested in 2-fold dilutions up to 200 µM), and HEK-293 (human embryonic kidney cells; 72-h MTT assay[48] only HP 29 was evaluated in 2-fold dilutions up to 200 µM).

Results from the cytotoxicity assessment of new HPs were very encouraging (Table 2). The majority of new HPs reported $IC_{50}$>100 µM against HeLa cells (6 of 9 new HPs evaluated). When tested against J774 MΦ and HepG2 cells, nearly all new HPs reported $IC_{50}$>200 µM, resulting in a selectivity index (SI) of >2,000 when considering the MIC values of HP analogues 29 and 30 against MRSA, MRSE and VRE strains (MIC=0.05-0.10 µM). HEK-293 cells demonstrated increased sensitivity towards HP 29 ($IC_{50}$=18.3±5.8 µM); however, gave a very good selectivity index (SI=244) when comparing its $IC_{50}$ against HEK-293 to MIC values against MRSA/MRSE strains (MIC=0.075 µM). Overall, this new series of HPs demonstrate very good to outstanding bacterial targeting results based on relative cytotoxicity profiles to antibacterial activities.

TABLE 2

Summary of HP cytotoxicity against HeLa, J774 MΦ, Hep G2 and HEK-293 cell lines. All results are reported in micromolar (µM) concentrations.

| Compound | MRSA-1707 MIC | HeLa Cell Cytotox. ($IC_{50}$) | J774 MΦ Cytotox. ($IC_{50}$) | Hep G2 Cytotox. ($IC_{50}$) | HEK-293 Cytotox. ($IC_{50}$) |
|---|---|---|---|---|---|
| 3  | 1.56 | >100 | >100 | >100 | — |
| 21 | 0.30 | >100 | >200 | >200 | — |
| 24 | 0.30 | >100 | >200 | >200 | — |
| 27 | 0.78 | 100  | —    | —    | — |
| 28 | 0.15 | >100 | >200 | >200 | — |
| 29 | 0.08 | >100 | >200 | >200 | 18.3 ± 5.8 |
| 30 | 0.08 | —    | >200 | >200 | — |
| 31 | 0.59 | —    | >200 | >200 | — |
| 32 | 0.15 | >100 | >200 | >200 | — |
| 33 | 0.15 | >25  | >200 | >200 | — |
| 34 | 0.59 | >100 | >200 | >200 | — |
| 35 | 0.30 | 100  | >200 | >200 | — |
| 45 | 0.30 | —    | >100 | >200 | — |

For Table 2: Assay Information: HeLa cytotoxicity (24-h, LDH release assay), J774 MΦ cytotoxicity (24-h, Alamar Blue assay), HepG2 cytotoxicity (24-h, Alamar Blue assay), HEK-293 cytotoxicity (72-h, MTT assay). Note: All experimental results are reported from a minimum of three independent cytotoxicity experiments.

Example 4. Biofilm Eradication and Iron Starvation

Initial MIC assays allowed us to determine planktonic growth inhibition activities of new HP analogues; however, HPs eradicate surface-attached bacterial biofilms with excellent potency, which require different microbiological assays. To investigate the biofilm-eradication activities of select compounds, our group has utilized Calgary Biofilm Device (CBD) assays to determine minimum biofilm eradication concentration (MBEC) values.[35-38] The CBD is a 96-well assay that has a specialized lid with anchored pegs that are submerged into microtiter wells allowing biofilm formation and subsequent transfer to fresh 96-well plates as the assay progresses.[49,50] Biofilm eradication assays have three phases, including: (1) biofilm establishment phase (inoculated media in a 96-well plate with CBD pegs submerged into microtiter wells providing a surface for biofilms to establish; 24-h incubation under static conditions), (2) compound treatment phase (pegs with established biofilms are gently rinsed to remove planktonic cells and transferred to a new 96-well plate containing 2-fold serially diluted test compound in fresh media; 24-h incubation), and (3) recovery phase (lid bearing compound-treated biofilms on CBD pegs is transferred to a final 96-well plate with fresh media only; 24-h incubation). Upon completion of CBD assays, biofilm eradication is determined by a turbidity readout. Microtiter wells that are turbid result from viable biofilms on CBD peg surfaces (live biofilms will disperse planktonic bacteria into fresh media and undergo replication/bacterial growth), whereas non-turbid microtiter wells result from completely eradicated biofilms. The lowest concentration at which biofilm eradication occurs is referred to as the minimum biofilm eradication concentration (MBEC) value.

The CBD allows one to determine planktonic versus biofilm cell killing dynamics of small molecules as these assays allow for the determination of minimum bactericidal concentration (MBC) and MBEC values simultaneously. This is an advantage over comparing MBEC to MIC values obtained from significantly different microbiological assays. In the past, we have found HPs to report MBC:MBEC ratios of 1:1 to 1:3 from CBD assays, demonstrating near equipotent planktonic- and biofilm-killing properties.[35-38]

Figure 5A:
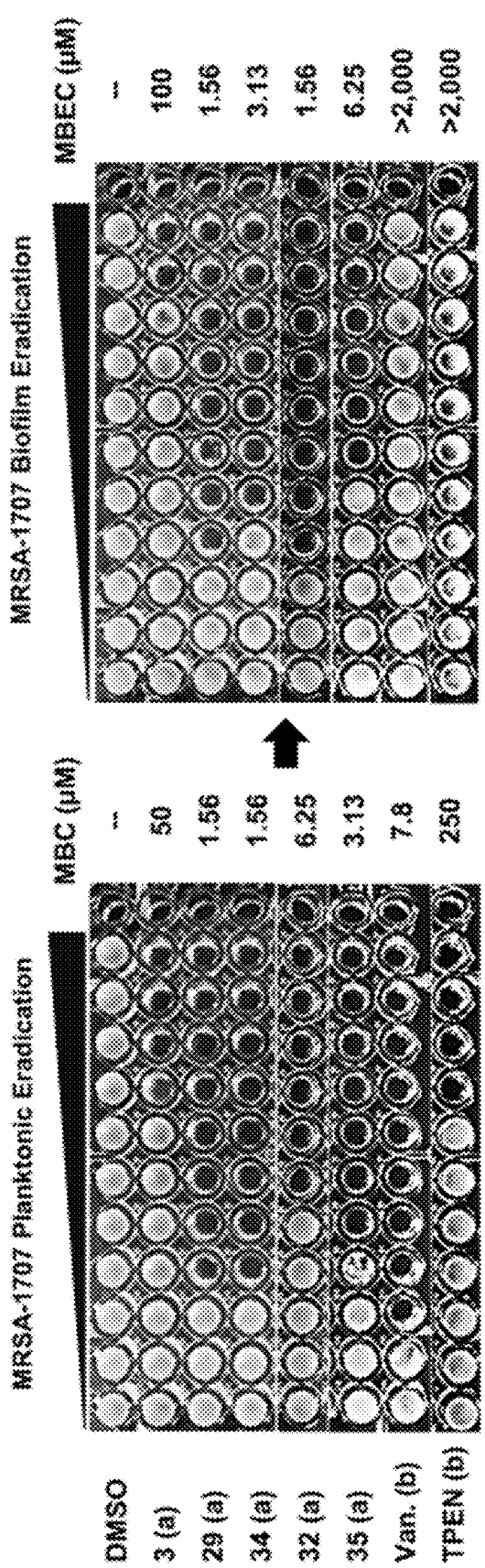
FIG. 5A shows a calgary biofilm device (CBD) assay of a panel of HPs and vancomycin against MRSA-1707.

We advanced a sub-set of 14 new HPs to MBEC assays against MRSA-1707 (Table 3). We investigated three non-brominated HPs from sub-series A (21, 24, 27) and found these analogues to have good activities with HPs 21 and 24 demonstrating the highest levels of biofilm killing (MBEC=37.5 µM, Table 3). We evaluated all sub-series B (dibrominated HP) analogues bearing a 3-chloro substituent in MBEC assays since these compounds demonstrated MIC values≤0.59 µM against MRSA-1707. Each of the 10 dibrominated HP analogues (sub-series B) reported MBEC values≤75 µM with five analogues demonstrating outstanding biofilm killing with MBECs at 2.35-4.69 µM (HPs 29, 30, 32, 34, 35, see FIG. 5A).

Figure 5B:
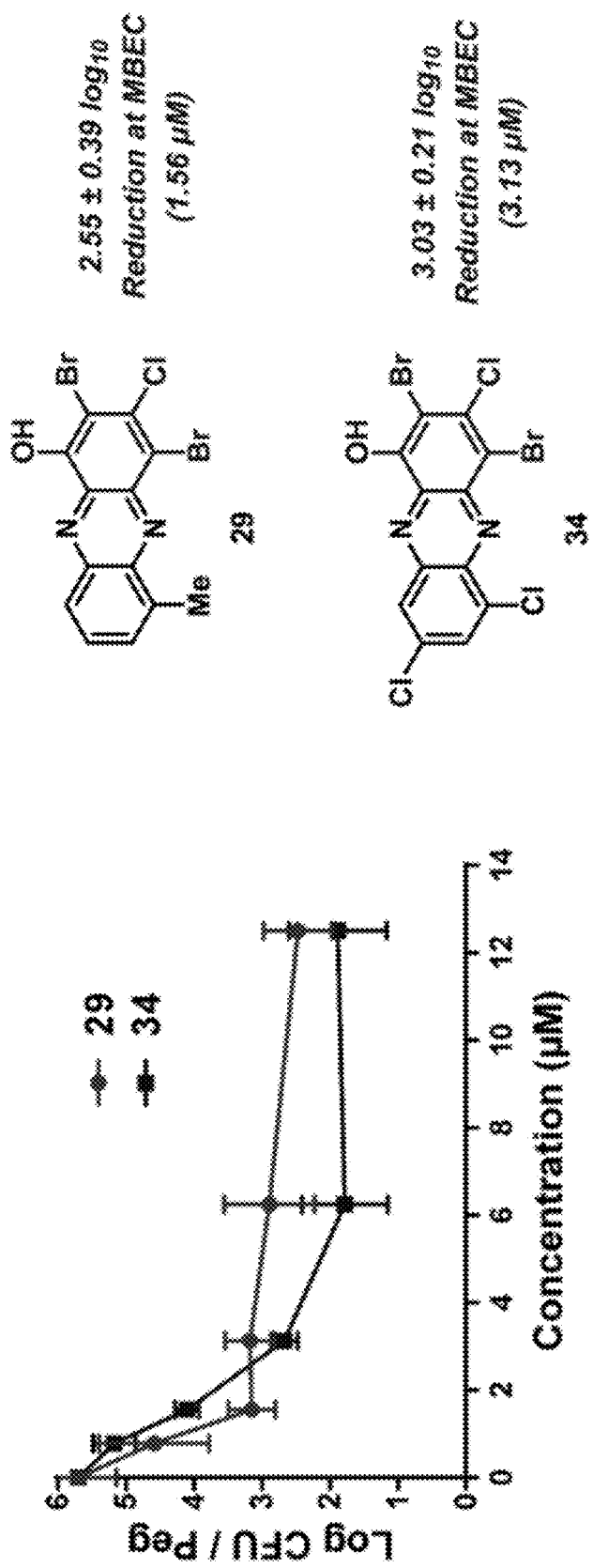
FIG. 5B shows MRSA-1707 biofilm cell killing (CFU/peg) for HPs 29 and 34 obtained from CBD pegs.

In addition, dose-response of biofilm killing was determined from CFU counts from CBD pegs against MRSA-1707 treated with HPs 29 (2.55±0.39 $\log_{10}$ reduction of viable biofilm cells at the MBEC value, FIG. 5B) and 34 (3.03±0.21 $\log_{10}$ reduction of viable MRSA-1707 biofilm cells). Together, HPs 29 and 34 demonstrated ~3 $\log_{10}$ reduction, or ~99.9% kill of MRSA-1707 biofilm cells at the corresponding MBEC value. Sub-series B analogues 29, 32, 34, and 35 were also evaluated for biofilm eradication activities against MRSA BAA-44 and demonstrated excellent biofilm-killing potencies with MBEC values between 6.25 and 18.8 µM (Table 3).

TABLE 3

Summary of biofilm eradication studies against MRSA, MRSE, VRE and *E. faecalis* biofilms. All biological results are reported in micromolar (µM) concentrations.

| Compound | MRSA-1707 MBC/MBEC | MRSA 44 MBC/MBEC | MRSE 35984 MBC/MBEC |
|---|---|---|---|
| 3 | $50^b/100^b$ | $37.5^a/75^a$ | $25^b/50^b$ |
| 21 | $18.8^a/37.5^a$ | — | — |
| 24 | $18.8^a/75^a$ | — | — |
| 27 | $37.5^a/37.5^a$ | — | — |
| 28 | 50/50 | $37.5^a/75^a$ | $12.5^b/25^b$ |
| 29 | $1.56^b/2.35^a$ | $4.69^a/6.25^b$ | $1.17^a/0.59^a$ |
| 30 | $18.8^a/4.69^a$ | — | $3.13^b/2.35^a$ |
| 31 | $75^a/75^a$ | — | $4.69^a/1.17^a$ |
| 32 | $9.38^a/2.35^a$ | $4.69^a/6.25^b$ | $1.56^b/1.56^b$ |
| 33 | $12.5^b/18.8^a$ | — | 12.5/12.5 |
| 34 | $2.35^a/3.13^b$ | $6.25^b/6.25^b$ | $0.59^a/0.30^a$ |
| 35 | $4.69^a/4.69^a$ | $6.25^a/18.8^a$ | $2.35^a/2.35^a$ |
| 36 | 12.5/12.5 | — | 6.25/6.25 |
| 37 | $12.5/9.38^a$ | — | 6.25/6.25 |
| 45 | $50^b/200$ | — | $12.5^b/4.69^a$ |
| 150 | /25 | — | $/18.8^a$ |
| 49 (QAC-10) | $93.8^a/93.8^a$ | — | 3.13/3.13 |
| TPEN | $375^a/>2000$ | — | $250/>2000$ |
| EDTA | $>2000/>2000$ | — | $1000/>2000$ |
| Vancomycin | $7.8/>2000$ | $7.8/>2000$ | $3.0^b/>2000$ |
| Daptomycin | $125/>2000$ | — | — |
| Linezolid | $31.3/>2000$ | — | — |

| Compound | VRE 700221 MBC/MBEC | E.faecalis OG1RF MBC/MBEC | % Hemolysis at 200 µM |
|---|---|---|---|
| 3 | $18.8^a/12.5^b$ | $25^b/>200*$ | ≤1 |
| 21 | — | — | ≤1 |
| 24 | — | — | ≤1 |
| 27 | — | — | 1.9 |
| 28 | $4.69^a/2.35^a$ | $75^a/>200*$ | ≤1 |
| 29 | $0.59^a/0.59^a$ | $6.25/18.8^a$ | ≤1 |
| 30 | $0.78^b/0.30^a$ | — | ≤1 |
| 31 | $2.35^a/0.20$ | $1.56^b/0.78^b$ | 27 |
| 32 | $0.78^b/0.39$ | $18.8^a/75^a$ | 2.6 |
| 33 | $3.13^b/1.17^a$ | — | ≤1 |
| 34 | $0.39^b/0.20$ | $3.13^b/1.17^a$ | ≤1 |
| 35 | $0.59^a/0.304$ | 6.25/6.25 | ≤1 |
| 36 | $4.69^a/0.598$ | — | 5.1 |
| 37 | $4.69^a/3.13b$ | — | 3.0 |
| 45 | $9.38^a/3.13b$ | — | 5.7 |
| 49 (QAC-10) | 3.04/3.04 | — | >99 |
| TPEN | $188^b/>2000$ | $500/>2000$ | ≤1 |
| EDTA | — | $>2000/>2000$ | ≤1 |
| Vancomycin | $750^a/>2000$ | $11.7^a/>2000$ | — |
| Daptomycin | $375/93.8^a$ | — | — |
| Linezolid | $4.69^b/1.56$ | — | — |

For Table 3: $^a$Midpoint of a 2-fold range in observed values. $^b$Midpoint of a 4-fold range in values. *Partial turbidity observed at highest test concentration. All values in this table resulted from a minimum of three independent experiments. Halogenated phenazines and QAC-10 were tested at concentrations up to 200 µM. Conventional antibiotics (e.g., vancomycin), EDTA and TPEN (metal-binding agents) were tested at concentrations up to 2,000 µM in CBD assays.

Figure 6A:
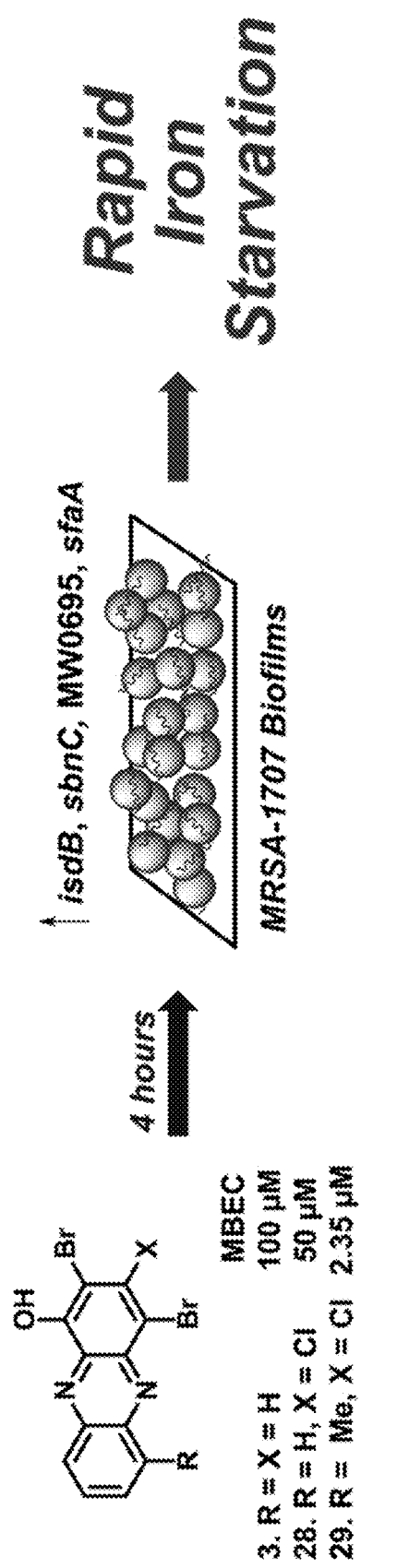
FIG. 6A shows that treating established MRSA-1707 biofilms with HPs 3, 28, and 29 led to induction of iron starvation.
Figure 6B:
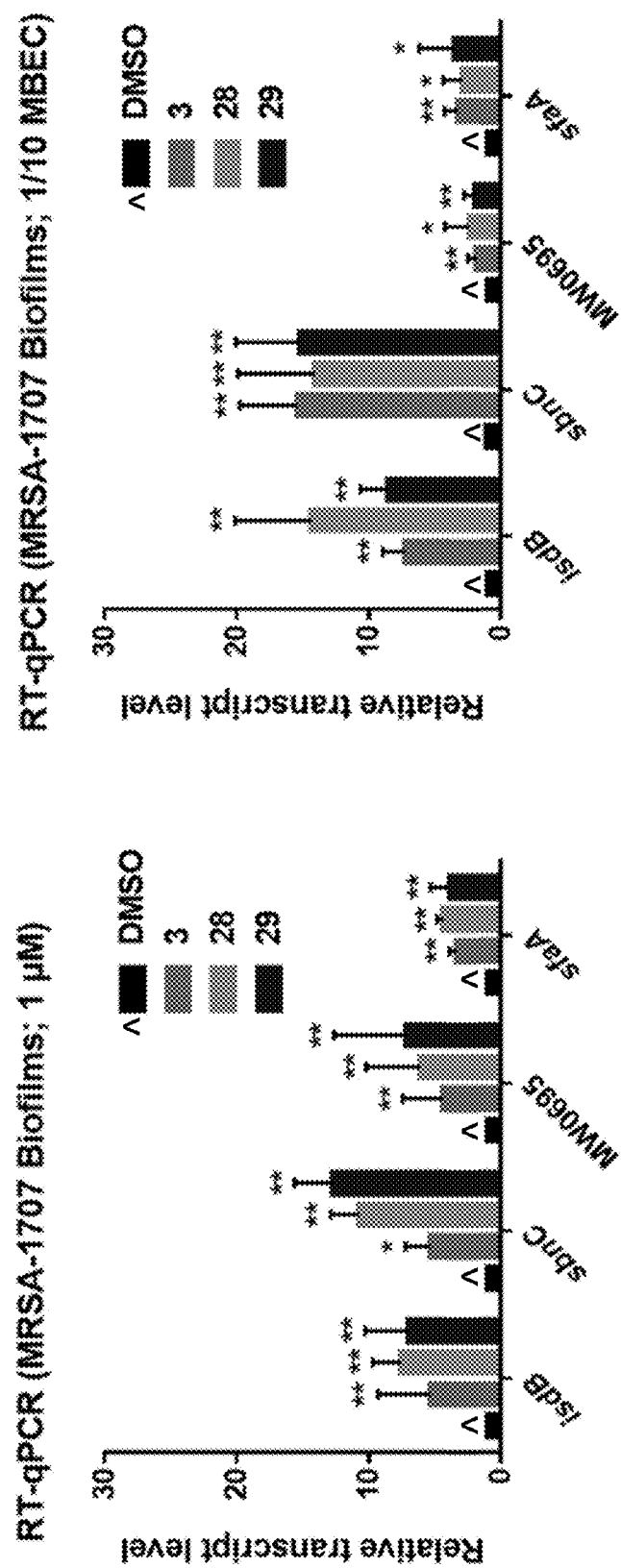
FIG. 6B shows RT-qPCR results of HPs 3, 28, and 29 up-regulating iron uptake genes in MRSA-1707 biofilms following 4 h treatment at 1 μM, or ⅒×MBEC; *p value≤0.05, **p≤0.01 (Student's T-test).
Figure 6C:
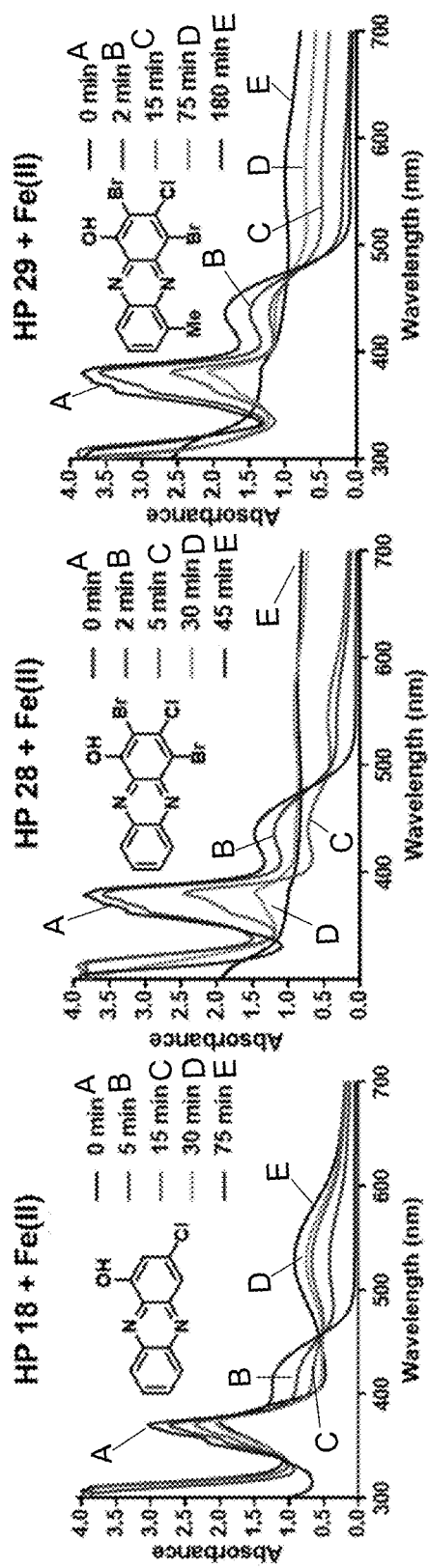
FIG. 6C shows UV-vis spectroscopy of HPs 18, 28, and 29 binding iron(II). It has been reported that EDTA and TPEN did not upregulate this panel of iron uptake genes at 5 μM.[39]

In addition to MBEC assays, we showed that HPs 3, 28, and 29 rapidly induce iron starvation in MRSA-1707 biofilms using RT-qPCR experiments (FIG. 6), which is in line with previous findings regarding 4 (HP-14).[39] Briefly, established MRSA-1707 biofilms were treated for 4 h with 3, 28 and 29 with 1/10×MBEC and 1 µM of each compound before RNA was extracted from HP- and vehicle-treated biofilm samples. RT-qPCR was then performed to investigate transcript levels from four different MRSA genes involved in iron uptake: isdB (iron regulated surface determinant; heme iron acquisition), sfaA (staphyloferrin A; siderophore), sbnC (staphyloferrin B; siderophore), and MW0695 (ferrichrome ABC transporter). Results from these experiments show HPs induce a rapid up-regulation of gene clusters involved in iron uptake (FIG. 6B) and we conclude biofilm eradication occurs due to iron starvation. HPs 18, 28, 29 and 34 were confirmed to directly bind iron(II) via UV-vis spectroscopy (see FIG. 6C), aligning with our RT-qPCR results related to the iron starvation of MRSA biofilms.

Following initial biofilm-killing studies in MRSA, select HPs were evaluated against other Gram-positive pathogens in CBD assays (Table 3). Several HPs demonstrated good (MBEC=12.5-25 µM) to outstanding (MBEC=0.30-6.25 µM) biofilm-killing potencies against MRSE 35984 with 29 (MBEC=0.59 µM), 31 (MBEC=1.17 µM), 32 (MBEC=1.56 µM) and 34 (MBEC=0.30 µM) proving most active. Dose-dependent killing of MRSE 35984 biofilm bacteria was determined by CFU counts from CBD pegs treated with HPs 29 (3.65±1.33 $\log_{10}$ reduction of viable MRSE biofilm cells at the MBEC value; FIG. 7B) and 34 (3.18±0.40 $\log_{10}$ reduction of viable MRSE biofilm cells at the MBEC value). In addition, these dose-response experiments show HPs 29 and 34 eradicate ~99.999% MRSE 35984 biofilm cells at 3.13 µM (~5 $\log_{10}$ reduction of viable CFUs).

In addition, HP analogues from sub-series B demonstrated good to excellent biofilm eradicating activities against enterococci strains (Table 3). Seven HPs showed remarkable biofilm-killing activity against *E. faecium* 700221 with MBEC values 0.20-0.59 µM (HP 31 and 34, MBEC=0.20 µM). Select HPs were evaluated against *E. faecalis* OG1RF biofilms with 31 (MBEC=0.78 µM), 34 (MBEC=1.17 µM) and 35 (MBEC=6.25 µM) proving to have the highest killing activities.

Vancomycin, daptomycin and linezolid are frontline antibiotics used to treat MRSA infections and, in our CBD assays, failed to eradicate MRSA-1707 biofilms despite effective planktonic killing (e.g., vancomycin, MBC=7.8 µM against planktonic cells, MBEC>2000 µM against MRSA biofilms; Table 3). In addition, QAC-10 is a membrane-lysing quaternary ammonium cation that displays good biofilm-eradicating activities[51] and serves as a valuable comparator in these investigations. QAC-10 eradicated MRSA-1707 biofilms with an MBEC of 93.8 µM in CBD assays, which is 20-fold less potent than our most active HPs in sub-series B. In addition, EDTA and TPEN (membrane-permeable agent) are general metal-chelating agents and are unable to eradicate biofilms at the highest test concentration (MBECs>2,000 µM; Table 3).

We then assessed the ability of our most active HP analogues to lyse red blood cells (RBCs). Hemolysis assays are used to determine the membrane-lysis activity of a compound, which is of particular interest to this work as membrane-lysing agents (e.g., QACs) can eradicate biofilms. During these investigations, we observed minimal hemolytic activity for nearly all new HP compounds at 200 µM (≤5% hemolysis; Table 3). QAC-10 was tested alongside HP analogues as an active membrane-lysing agent (comparator) and caused >99% hemolysis of RBCs at 200 µM.

Example 5. In Vivo Assessment of HP 29 in Dorsal Wound Infection Models

Based on its potent antibacterial activities, rapid induction of iron starvation in MRSA biofilms and excellent cytotoxicity profile, HP 29 was evaluated for in vivo efficacy against *S. aureus* and *E. faecalis* using dorsal wound infection models in mice. *S. aureus* and *E. faecalis* are highly prevalent in both hospital acquired and wound infections.[52,53] In addition, these pathogens are notorious for their antibiotic-resistant phenotypes and propensity to form tolerant biofilms.[54,55]

For the in vivo experiments, HP 29 was formulated in a PEG-based ointment[52] for topical application. In separate experiments, wounds were created on the mouse's dorsal mid-section using a biopsy punch to remove the dermal layer. The resulting wound was inoculated with either *S. aureus* UAMS-1 ($1\times10^7$ CFU/mL), or *E. faecalis* OG1RF ($6\times10$ CFU/mL) to establish infection. Following infection, PEG ointment containing HP 29 or PEG-ointment alone (vehicle control) was directly applied to the infected wounds twice (*S. aureus* infection) or once (*E. faecalis* infection) for three days before mice were sacrificed and the bacterial load in each wound was determined as CFU per lesion (FIGS. 8A and 8B).

Results from the dorsal wound infection experiments demonstrated that HP 29 treatment led to a significant decolonization of both *S. aureus* and *E. faecalis*. HP 29-treated mice led to an 0.82-$\log_{10}$ reduction in CFU per lesion of *S. aureus* UAMS-1 compared to vehicle treated mice following three consecutive days of treatment (FIG. 8A). Against *E. faecalis* OG1RF, HP 29 showed more efficacious decolonization with 1.73-$\log_{10}$ reduction compared to vehicle control after treatment (FIG. 8B). Collectively, these results indicate that HP agents are a useful alternative for the topical treatment of wounds infected by Gram-positive pathogens.

Example 6. Structure-Activity Relationship Analysis

This new collection of HPs has significantly expanded structure-activity relationship profiles for these antibacterial agents (FIG. 9). In addition to the synthesis and biological assessment of 3-substituted HPs, we determined pKa and C Log P values (ChemDraw) of select analogues for further analysis.

New key insights into HP antibacterial agents from these studies include: (1) a 3-chlorine atom on the HP scaffold may increase the antibacterial/biofilm eradication activities, acidity of the phenolic proton, and C Log P values (see sub-series B, FIG. 9), and (2) thiol substituents at the 3-position diminished antibacterial activities compared to 3-chlorinated HP analogues (comparing sub-series C to sub-series B analogues) and reduced acidity of the phenolic proton.

As noted, the 3-chlorine atom may have an impact on the acidity of the phenolic proton of HP analogues and we believe this may prime the HP scaffold for iron binding as the alkoxy anion. In addition, the 3-chlorine atom may increase the C Log P value of HP analogues (that are largely anionic in biological assays performed at pH~7), which could lead to rapid diffusion through bacterial membranes to bind intracellular iron(II). For instance, parent HP 3 is without a 3-chlorine atom and has an MIC=1.56 µM (MRSA), MBEC=100 µM (MRSA), pKa of 7.12 and C Log P value of 4.68, whereas HP 28 has the addition of a chlorine atom in the 3-position of the HP and has an MIC=0.15 µM (MRSA), MBEC=50 µM (MRSA), pKa of 5.93 and C Log P of 5.12 (FIG. 9). A similar profile can be observed when comparing HPs 6 (MIC=0.30 µM, MRSA; MBEC=6.25 µM, MRSA; C Log P=5.18; pKa not determined) and 29 (MIC=0.08 µM, MRSA; MBEC=2.35 µM, MRSA; C Log P=5.62; pKa=6.79; FIG. 9).

Several HPs from sub-series B demonstrate high levels of planktonic and biofilm-killing activities against Gram-positive pathogens, including multidrug-resistant strains. HP 29 demonstrated outstanding in vitro activities in addition to encouraging in vivo efficacy in dorsal wound infections against *S. aureus* UAMS-1 and *E. faecalis* OGRF1. Multiple HPs demonstrated rapid iron starvation in MRSA biofilms as a result of their ability to bind iron between the hydroxyl oxygen at the 1-position of the HP scaffold and nitrogen at the 10-position.

Conclusions

In conclusion, we utilized aniline building blocks to rapidly access a diverse series of N-aryl-2-nitrosoaniline intermediates en route to new halogenated phenazine antibacterial agents. This chemistry enabled the first study of HPs functionalized at the 3-position with chlorine or thiol substituents. This collection of >20 HP analogues demonstrated highly potent antibacterial and biofilm eradication activities against Gram-positive pathogens (e.g., HP 29, MIC=0.075 µM, MBEC=2.35 µM against MRSA-1707) and multiple HPs were shown to induce rapid iron starvation in MRSA biofilms. In addition, several new HPs reported good to excellent activities against *M. tuberculosis* (e.g., HP 34, MIC=0.80 µM against *M. tuberculosis* CDC1551). Three diverse sub-series of HPs provided significant SAR insights into this antibacterial scaffold and HP 29 demonstrated in vivo efficacy against *S. aureus* and *E. faecalis* in wound infection models in mice. These findings could lead to significantly improved treatment options for antibiotic-resistant and -tolerant bacterial infections, including wound and chronic biofilm-associated infections.

Experimental

General Information. All reagents for chemical synthesis were purchased at ≥95% purity from commercial sources and used without further purification. All microwave reactions were carried out using an Anton Paar Monowave 300 Microwave Synthesis Reactor. A constant power was applied to ensure reproducibility regarding microwave reactions as temperature control was automated via IR sensor and all indicated temperatures correspond to the maximal temperature reached during each experiment. Analytical thin layer chromatography (TLC) was performed using 250 µm Silica Gel 60 F254 pre-coated plates (EMD Chemicals Inc.) and used to monitor all reactions. Flash column chromatography was performed using 230-400 Mesh 60 Å Silica Gel from Sorbent Technologies. Melting points were obtained, uncorrected, using a Mel-Temp capillary melting point apparatus from Laboratory Services, Inc.

NMR experiments were recorded using broadband probes on a Varian Mercury-Plus-400 spectrometer via VNMR-J software (400 MHz for $^1$H and 101 MHz for $^{13}$C), Varian Mercury-Plus-500 spectrometer via VNMR-J software (500 MHz for $^1$H and 126 MHz for $^{13}$C), Bruker Avance III (500 MHz for $^1$H; 126 MHz for $^{13}$C) and Bruker Avance II (600 MHz for $^1$H; 151 MHz for $^{13}$C). All spectra are presented using MestReNova 11.0 (Mnova) software and are displayed without the use of the signal suppression function. Spectra were obtained in the following solvents (reference peaks for $^1$H and $^{13}$C NMRs are included): CDCl$_3$ ($^1$H NMR, 7.26 ppm; $^{13}$C NMR, 77.23 ppm) and DMSO-d$_6$ ($^1$H NMR, 2.50 ppm; $^{13}$C NMR, 39.52 ppm). All NMR experiments were performed at room temperature. Chemical shift values (δ) are reported in parts per million (ppm) for all $^1$H NMR and $^{13}$C NMR spectra. $^1$H NMR multiplicities are reported as: s=singlet, br. s=broad singlet, d=doublet, t=triplet, q=quartet, m=multiplet. HSQC was used to identify a few challenging $^{13}$C signals. High-Resolution Mass Spectrometry (HRMS) were obtained for all new compounds from the Chemistry Department at the University of Florida.

Multiple controls and comparator agents (e.g., antibiotics, EDTA) were purchased and used in biological assays. All synthesized compounds evaluated in biological assays were determined to be ≥95% pure using a Shimadzu Prominence HPLC system, AB Sciex 3200 QTRAP spectrometer and a Kinetex C18 column (50 mm×2.1 mm×2.6 µm) with a 21 minute linear gradient from 10 to 80% acetonitrile in 0.1% formic acid at a flow rate of 0.25 mL/min (traces and purity analysis can be viewed in the supporting information). All compounds were stored as DMSO stocks at room temperature in the absence of light for several months at a time without observing losses in biological activity. To ensure the integrity of DMSO stock solutions of test compounds, they were not subjected to freeze-thaw cycles. Bacterial strains used during these investigations include: *S. aureus* BAA-1707 ("MRSA-1707"), BAA-44 and UAMS-1, *S. epidermidis* ATCC 35984, *E. faecium* ATCC 700221, *E. faecalis* OG1RF (ATCC 47077), *S. pneumoniae* ATCC 6303, *M. tuberculosis* H37Ra (ATCC 25177) and CDC1551. All animal experiments performed were conducted in compliance with institutional guidelines.

Chemistry. This chemistry section includes the following items: (a) synthetic procedures and compound characterization (ordered by synthetic route, (b) UV-vis for HPs binding iron(II), and (c) pKa determination of select HP analogues.
(a) Synthetic Procedures and Compound Characterization.

General two-step procedure for the synthesis of 3-chloro-1-methoxyphenazines (38, 50-58).[44,45] Step 1. 4-Bromoaniline (303 mg, 1.76 mmol) dissolved in 2 mL of N,N-dimethylformamide was added dropwise to a stirring solution of potassium tert-butoxide (416 mg, 4.80 mmol) in N,N-dimethylformamide (12 mL) at −60° C. Then, a solution of 5-choloro-2-nitroanisole 13 (300 mg, 1.60 mmol) in N,N-dimethylformamide (2 mL) was added to the mixture which continued to stir at −60° C. for 7 hours. Upon completion of this reaction, the resulting mixture was transferred to a separatory funnel containing saturated aqueous ammonium chloride (80 mL) and the crude product was extracted with ethyl acetate (3×30 mL). The organic layers were then combined, washed with brine, and dried with sodium sulfate. The resulting organic layer was then filtered and concentrated in vacuo to obtain the crude nitroso intermediate that was used directly in the next step. Step 2. The crude nitroso intermediate (oil) was dissolved in N,N-dimethylformamide (10 mL) before N,O-bis(trimethylsilyl)acetamide (1.97 mL, 8.00 mmol) was added to the solution. The resulting mixture was allowed to stir at 50° C. for 16 hours until complete. After this time, 2 mL of water was added to the mixture and stirring continued at room temperature for an additional 10 minutes before the precipitate was filtered and washed with cold ethyl acetate (this solid was a batch of desired product). The filtrate was then transferred to a separatory funnel containing brine (50 mL) and extracted with ethyl acetate (3×30 mL) to isolate additional product. After extraction of the filtrate, the organic layers were combined and washed with water (3×50 mL), dried with sodium sulfate, filtered, and concentrated in vacuo. The resulting crude solid was purified via silica gel chromatography using hexanes:ethyl acetate (99:1 to 85:15) to afford a yellow solid as a second product batch, which was combined with the solid obtained above to afford 57 (413 mg, 80% yield).

3-Chloro-1-methoxy-6-methylphenazine (38). Yield: 80%; 578 mg was isolated as a yellow solid. $^1$H NMR (400 MHz, CDCl$_3$): δ 8.18 (d, J=8.4 Hz, 1H), 7.87 (d, J=2.0 Hz, 1H), 7.74-7.62 (m, 2H), 6.98 (d, J=2.0 Hz, 1H), 4.16 (s, 3H), 2.87 (s, 3H). $^{13}$C NMR (101 MHz, CDCl$_3$): δ 155.6, 143.8, 143.3, 142.4, 137.8, 136.3, 135.2, 130.7, 130.6, 128.2, 120.7, 108.7, 57.0, 17.8. HRMS (ESI): calc. for C$_{14}$H$_{12}$ClN$_2$O [M+H]$^+$: 259.0633, found: 259.0642. MP: 178-180° C.

3-Chloro-1-methoxyphenazine (50). Yield: 44%; 105 mg was isolated as a yellow solid. Note: $^1$H NMR and $^{13}$C NMR spectral data match those previously reported for this compound (CAS: 1346682-87-8).[44]

8-Chloro-6-methoxy-1,2-dimethylphenazine (51). Yield: 72%; 211 mg was isolated as a yellow solid. $^1$H NMR (400 MHz, CDCl$_3$): δ 8.10 (d, J=9.0 Hz, 1H), 7.86 (d, J=1.5 Hz, 1H), 7.64 (d, J=9.0 Hz, 1H), 6.98 (d, J=1.5 Hz, 1H), 4.17 (s, 3H), 2.82 (s, 3H), 2.57 (s, 3H). $^{13}$C NMR (101 MHz, CDCl$_3$): δ 155.7, 143.7, 143.3, 141.2, 139.0, 136.1, 134.6, 134.5, 134.2, 127.1, 120.7, 108.3, 57.0, 21.0, 13.3. HRMS (ESI): calc. for C$_{15}$H$_{14}$ClN$_2$O [M+H]$^+$: 273.0789, found: 273.0799. MP: 174-176° C.

2-Bromo-8-chloro-6-methoxy-1-methylphenazine (52). Yield: 72%; 388 mg was isolated as a yellow solid. $^1$H NMR (400 MHz, CDCl$_3$): δ 8.04 (d, J=9.3 Hz, 1H), 7.90 (d, J=9.3 Hz, 1H), 7.84 (d, J=2.0 Hz, 1H), 7.00 (d, J=2.0 Hz, 1H), 4.17 (s, 3H), 2.95 (s, 3H). $^{13}$C NMR (101 MHz, CDCl$_3$): δ 155.6, 143.6, 143.4, 141.2, 137.5, 137.2, 135.1, 135.0, 128.7, 127.4, 120.6, 109.0, 57.1, 17.6. HRMS (ESI): calc. for C$_{14}$H$_{11}$BrClN$_2$O [M+H]$^+$: 336.9738, found: 336.9734. MP: 218-220° C.

3-Chloro-1-methoxy-6-phenoxyphenazine (53). Yield: 69%; 445 mg was isolated as a yellow solid. $^1$H NMR (600 MHz, CDCl$_3$): δ 8.08 (d, J=8.8 Hz, 1H), 8.00 (d, J=2.0 Hz, 1H), 7.68 (dd, J=8.8, 7.6 Hz, 1H), 7.47-7.41 (m, 2H), 7.26-7.21 (m, 3H), 7.08 (d, J=7.6 Hz, 1H), 7.05 (d, J=2.0 Hz, 1H), 4.20 (s, 3H). $^{13}$C NMR (151 MHz, CDCl$_3$): δ 156.4, 155.5, 154.1, 143.2, 143.0, 137.7, 137.0, 135.9, 130.2, 130.1, 124.8, 124.3, 120.8, 120.8, 114.7, 109.3, 57.0. HRMS (ESI): calc. for C$_{19}$H$_{14}$ClN$_2$O$_2$[M+H]$^+$: 337.0738, found: 337.0752. MP: 178-180° C.

3-Chloro-8-fluoro-1-methoxyphenazine (54). Yield: 82%; 344 mg was isolated as a yellow solid. $^1$H NMR (400 MHz, CDCl$_3$): δ 8.21 (dd, J=9.5, 5.9 Hz, 1H), 7.96 (dd, J=9.4, 2.8 Hz, 1H), 7.82 (d, J=2.0 Hz, 1H), 7.68 (ddd, J=9.5, 7.9, 2.8 Hz, 1H), 7.03 (d, J=2.0 Hz, 1H), 4.18 (s, 3H). $^{13}$C NMR (101 MHz, CDCl$_3$): δ 163.2 (d, J=255.7 Hz), 155.5, 143.6 (d, J=2.8 Hz), 142.7 (d, J=13.7 Hz), 141.7, 136.8 (d, J=1.8 Hz), 136.0, 131.9 (d, J=10.2 Hz), 123.6 (d, J=28.3 Hz), 120.3 (d, J=1.2 Hz), 112.6 (d, J=21.5 Hz), 109.5, 57.1. HRMS (ESI): calc. for C$_{13}$H$_9$ClFN$_2$O [M+H]$^+$: 263.0382, found: 263.0394. MP: 221-223° C.

1,3,8-Trichloro-6-methoxyphenazine (55). Yield: 34%; 175 mg was isolated as a yellow solid. $^1$H NMR (400 MHz, CDCl$_3$): δ 8.26 (s, 1H), 7.98-7.86 (m, 2H), 7.03 (s, 1H), 4.17 (s, 3H). $^{13}$C NMR (101 MHz, CDCl$_3$): δ 155.5, 143.7, 142.2, 139.4, 138.2, 136.3, 135.7, 134.2, 132.0, 127.9, 120.6, 110.1, 57.2. HRMS (DART): calc. for C$_{13}$H$_8$Cl$_3$N$_2$O [M+H]$^+$: 312.9697, found: 312.9696. MP: 221-223° C.

6-Bromo-3-chloro-1-methoxyphenazine (56). Yield: 61%; 183 mg was isolated as a yellow solid. $^1$H NMR (500 MHz, CDCl$_3$): δ 8.34 (dd, J=8.8, 1.3 Hz, 1H), 8.20 (d, J=7.3, 1.3 Hz, 1H), 7.99 (d, J=2.0 Hz, 1H), 7.68 (dd, J=8.8, 7.3 Hz, 1H), 7.05 (d, J=2.0 Hz, 1H), 4.19 (s, 3H). $^{13}$C NMR (101 MHz, CDCl$_3$): δ 155.5, 144.2, 142.6, 141.5, 137.9, 136.0, 134.7, 130.5, 130.3, 124.1, 120.6, 109.6, 57.1. HRMS (ESI): calc. for C$_{13}$H$_9$BrClN$_2$O [M+H]$^+$: 322.9581, found: 322.9578. MP: 137-139° C.

8-Bromo-3-chloro-1-methoxyphenazine (57). Yield: 80%; 413 mg was isolated as a yellow solid. $^1$H NMR (400 MHz, CDCl$_3$): δ 8.55 (d, J=2.1 Hz, 1H), 8.04 (d, J=9.2 Hz, 1H), 7.89 (dd, J=9.2, 2.1 Hz, 1H), 7.78 (d, J=2.0 Hz, 1H), 7.01 (d, J=2.0 Hz, 1H), 4.17 (s, 3H). $^{13}$C NMR (101 MHz, CDCl$_3$): δ 155.7, 144.1, 142.7, 142.3, 137.5, 135.9, 135.3, 132.3, 130.7, 125.1, 120.3, 109.5, 57.1. HRMS (ESI): calc. for C$_{13}$H$_9$BrClN$_2$O [M+H]$^+$: 322.9581, found: 322.9580. MP: 225-227° C.

3-Chloro-8-iodo-1-methoxyphenazine (58). Yield: 65%; 388 mg was isolated as a yellow solid. $^1$H NMR (400 MHz, CDCl$_3$): δ 8.83 (d, J=1.9 Hz, 1H), 8.06 (dd, J=9.1, 1.9 Hz, 1H), 7.89 (d, J=9.1 Hz, 1H), 7.80 (d, J=2.0 Hz, 1H), 7.02 (d, J=2.0 Hz, 1H), 4.17 (s, 3H). $^{13}$C NMR (101 MHz, CDCl$_3$): δ 155.8, 144.1, 143.0, 142.5, 140.2, 139.3, 137.6, 135.7, 130.4, 120.2, 109.4, 97.2, 57.1. HRMS (ESI): calc. for C$_{13}$H$_9$ClIN$_2$O [M+H]$^+$: 370.9443, found: 370.9448. MP: 224-226° C.

Boron tribromide demethylation of 3-chloro-1-methoxyphenazines to 3-chloro-1-hydroxyphenazines (18-27). Compound 38 (200 mg, 0.77 mmol) was dissolved in anhydrous dichloromethane (50 mL) in a round bottom flask. The solution was then cooled to −78° C. before a 1 M solution of boron tribromide (4.6 mL, 4.6 mmol in dichloromethane) was added dropwise. The resulting reaction mixture was allowed to stir at −78° C. for 1 hour before being warmed to room temperature overnight. After this time, the reaction was heated to reflux until complete (monitored by TLC). Upon completion, brine (50 mL) was added to the mixture to quench the reaction. The resulting mixture was then transferred to a separatory funnel and extracted with dichloromethane. The combined organic layers were dried with sodium sulfate, filtered, and concentrated in vacuo. The resulting solid was purified via column chromatography using dichloromethane to elute compound 19 as a yellow solid (191 mg, 100%).

3-Chlorophenazin-1-ol (18). Yield: 89%; 84.0 mg was isolated as a yellow solid. $^1$H NMR (400 MHz, CDCl$_3$): δ 8.27 (br. s, 1H), 8.26-8.18 (m, 2H), 7.92-7.83 (m, 2H), 7.79 (d, J=2.0 Hz, 1H), 7.22 (d, J=2.0 Hz, 1H). $^{13}$C NMR (101 MHz, CDCl$_3$): δ 152.4, 145.0, 143.8, 141.2, 138.3, 133.5, 131.6, 131.0, 129.9, 129.4, 118.9, 111.0. HRMS (ESI): calc. for C$_{12}$H$_8$ClN$_2$O [M+H]$^+$: 231.0320, found: 231.0329. MP: 213-215° C. HPLC purity: 98.7%.

3-Chloro-6-methylphenazin-1-ol (19). Yield: 100%; 191 mg was isolated as a yellow solid. $^1$H NMR (600 MHz, DMSO-d$_6$): δ 11.16 (br. s, 1H), 8.08 (dd, J=8.5, 1.6 Hz, 1H), 7.86-7.76 (m, 2H), 7.72 (d, J=2.2 Hz, 1H), 7.15 (d, J=2.2 Hz, 1H), 2.79 (s, 3H). $^{13}$C NMR (101 MHz, DMSO-d$_6$): δ 154.8, 142.8, 142.7, 141.4, 137.0, 136.2, 134.4, 130.9, 130.7, 127.4, 117.8, 111.3, 17.3. HRMS (ESI): calc. for C$_{13}$H$_{10}$ClN$_2$O [M+H]$^+$: 245.0476, found: 245.0464. MP: 185-187° C. HPLC purity: 97.8%.

3-Chloro-6,7-dimethylphenazin-1-ol (20). Yield: 93%; 123 mg was isolated as a yellow solid. $^1$H NMR (400 MHz, CDCl$_3$): δ 8.19 (br. s, 1H), 7.87 (d, J=8.9 Hz, 1H), 7.74 (d, J=2.0 Hz, 1H), 7.60 (d, J=8.9 Hz, 1H), 7.12 (d, J=2.0 Hz, 1H), 2.79 (s, 3H), 2.56 (s, 3H). $^{13}$C NMR (101 MHz, CDCl$_3$): δ 152.2, 144.3, 142.8, 140.0, 138.9, 137.2, 134.8, 134.5, 132.2, 126.0, 119.2, 110.3, 21.0, 13.4. HRMS (ESI): calc. for C$_{14}$H$_{12}$ClN$_2$O [M+H]$^+$: 259.0633, found: 259.0642. MP: 183-185° C. HPLC purity: 99.1%.

7-Bromo-3-chloro-6-methylphenazin-1-ol (21). Yield: 100%; 122 mg was isolated as a yellow solid. $^1$H NMR (400 MHz, CDCl$_3$): δ 8.14 (s, 1H), 7.97-7.89 (m, 2H), 7.83 (d, J=2.0 Hz, 1H), 7.22 (d, J=2.1 Hz, 1H), 3.00 (s, 3H). $^{13}$C NMR (151 MHz, CDCl$_3$): δ 152.3, 144.4, 143.1, 140.2, 138.5, 138.0, 135.4, 132.8, 127.7, 127.4, 119.3, 111.3, 17.8. HRMS (ESI): calc. for C$_{13}$H$_7$BrClN$_2$O [M−H]$^−$: 320.9436, found: 320.9421. MP: 210-212° C. HPLC purity: 99.3%.

3-Chloro-6-phenoxyphenazin-1-ol (22). Yield: 100%; 118 mg was isolated as a yellow solid. $^1$H NMR (500 MHz, CDCl$_3$): δ 8.23 (s, 1H), 7.94 (d, J=2.0 Hz, 1H), 7.92 (dd, J=8.8, 1.1 Hz, 1H), 7.69 (dd, J=8.8, 7.6 Hz, 1H), 7.48-7.41 (m, 2H), 7.28-7.20 (m, 4H), 7.08 (dd, J=7.6, 1.1 Hz, 1H). $^{13}$C NMR (101 MHz, CDCl$_3$): δ 156.3, 154.5, 152.2, 142.8, 141.9, 138.4, 138.2, 133.7, 130.5, 130.3, 125.1, 123.2, 120.9, 119.5, 114.5, 111.5. HRMS (ESI): calc. for C$_{18}$H$_{12}$ClN$_2$O$_2$ [M+H]$^+$: 323.0582, found: 323.0570. MP: 168-170° C. HPLC purity: 97.4%.

3-Chloro-8-fluorophenazin-1-ol (23). Yield: 100%; 95 mg was isolated as a yellow solid. $^1$H NMR (400 MHz, DMSO-d$_6$): δ 11.32 (br. s, 1H), 8.29 (ddd, J=9.4, 6.1, 0.7 Hz, 1H), 8.01-7.91 (m, 2H), 7.73 (d, J=2.2 Hz, 1H), 7.17 (d, J=2.2 Hz, 1H). $^{13}$C NMR (101 MHz, DMSO-d$_6$): δ 162.5 (d, J=253.0 Hz), 154.6, 143.0 (d, J=2.5 Hz), 141.6 (d, J=13.9 Hz), 141.0, 136.2 (d, J=1.7 Hz), 135.0, 131.9 (d, J=10.5 Hz), 123.6 (d, J=28.4 Hz), 117.6, 112.0, 111.7 (d, J=21.1 Hz). HRMS (ESI): calc. C$_{12}$H$_5$FClN$_2$O for [M−H]$^−$: 247.0080, found: 247.0078. MP: 214-216° C. HPLC purity: >99.9%.

3,6,8-Trichlorophenazin-1-ol (24). Yield: 96%; 116 mg was isolated as a yellow solid. $^1$H NMR (600 MHz, CDCl$_3$): δ 8.15 (d, J=2.2 Hz, 1H), 8.06 (s, 1H), 7.96 (d, J=2.2 Hz, 1H), 7.92 (d, J=2.0 Hz, 1H), 7.27 (d, J=2.0 Hz, 1H). $^{13}$C NMR (101 MHz, CDCl$_3$): δ 152.1, 143.4, 141.2, 140.2, 139.5, 136.1, 134.7, 134.1, 132.1, 127.0, 119.4, 112.6. HRMS (ESI): calc. for C$_{12}$H$_4$Cl$_3$N$_2$O [M−H]$^−$: 296.9395, found: 296.9403. MP: 234-236° C. HPLC purity: 97.6%.

6-Bromo-3-chlorophenazin-1-ol (25). Yield: 100%; 141 mg was isolated as a yellow solid. $^1$H NMR (400 MHz, CDCl$_3$): δ 8.26-8.18 (m, 2H), 8.15 (s, 1H), 7.96 (d, J=2.0 Hz, 1H), 7.71 (dd, J=8.7, 7.3 Hz, 1H), 7.26 (m, 1H, partially buried in reference signal). $^{13}$C NMR (151 MHz, CDCl$_3$): δ 152.2, 143.9, 142.3, 141.7, 139.1, 134.8, 133.9, 130.8, 129.3, 124.7, 119.4, 111.9. HRMS (ESI): calc. for C$_{12}$H$_5$BrClN$_2$O [M−H]$^−$: 306.9279, found: 306.9277. MP: 223-225° C. HPLC purity: 98.2%.

8-Bromo-3-chlorophenazin-1-ol (26). Yield: 100%; 103 mg was isolated as a yellow solid. $^1$H NMR (600 MHz, DMSO-d$_6$): δ 11.30 (br. s, 1H), 8.45 (d, J=2.1 Hz, 1H), 8.11 (d, J=9.2 Hz, 1H), 8.05 (dd, J=9.2, 2.1 Hz, 1H), 7.70 (d, J=2.1 Hz, 1H), 7.16 (d, J=2.1 Hz, 1H). $^{13}$C NMR (151 MHz, DMSO-d$_6$): δ 154.8, 143.5, 142.0, 141.4, 136.9, 135.0, 134.9, 131.2, 130.8, 124.1, 117.5, 111.9. HRMS (ESI): calc. for C$_{12}$H$_5$BrClN$_2$O [M−H]$^−$: 306.9279, found: 306.9274. MP: 251-253° C. HPLC purity: 98.1%.

3-Chloro-8-iodophenazin-1-ol (27). Yield: 100%; 110 mg was isolated as a yellow solid. $^1$H NMR (600 MHz, DMSO-d$_6$): δ 11.28 (br. s, 1H), 8.69 (d, J=1.8 Hz, 1H), 8.19 (dd, J=9.1, 1.8 Hz, 1H), 7.96 (d, J=9.1 Hz, 1H), 7.73 (d, J=2.1 Hz, 1H), 7.18 (d, J=2.1 Hz, 1H). $^{13}$C NMR (151 MHz, DMSO-d$_6$): δ 154.9, 143.6, 142.3, 141.8, 140.0, 137.9, 136.9, 134.8, 130.4, 117.5, 111.8, 98.3. HRMS (ESI): calc. for C$_{12}$H$_5$ClIN$_2$O [M−H]$^−$: 354.9141, found: 354.9145. MP: 233-235° C. HPLC purity: 97.9%.

General Procedures for Nucleophilic Aromatic Substitution (NAS).

NAS reaction method A (39, 40 and 42). 3-Chloro-1-methoxy-6-methylphenazine 38 (160 mg, 0.62 mmol) and potassium carbonate were suspended in anhydrous N,N-dimethylformamide (6 mL) in a sealed tube. The resulting mixture was then purged with argon for 30 minutes before 2-mercaptoethanol (350 µL, 4.94 mmol) was added. The sealed tube was then closed and the reaction was allowed to stir at 85° C. for 7 days. Upon completion, the reaction mixture was transferred to a separatory funnel containing brine (100 mL) and extracted with ethyl acetate (3×50 mL). The resulting organic extracts were then combined, washed with water, dried with anhydrous sodium sulfate, filtered, and concentrated in vacuo. The resulting crude solid was then purified via flash column chromatography using hexanes:ethyl acetate (4:1 to 1:1) to afford 43 as a yellow solid (30 mg, 17%), and 40 as a yellow solid (96 mg, 52%).

NAS reaction method B (41, 43 and 44). 3-Chloro-1-methoxy-6-methylphenazine 38 (147 mg, 0.57 mmol) was dissolved in N,N-dimethylformamide (6 mL) in a microwave reaction vessel. Then, potassium carbonate (392 mg, 2.84 mmol) and 2,5,8,11-tetraoxatridecane-13-thiol 61 (956 mg, 4.54 mmol) were added to the reaction vessel, which was then purged with argon for 3 minutes before being sealed and heating to 200° C. for 152 seconds. Upon completion, the reaction mixture was then transferred to a separatory funnel containing ethyl acetate (50 mL) and brine (50 mL). The product was extracted and the organic layer was collected, washed with brine (3×50 mL), dried with anhydrous sodium sulfate, filtered and concentrated in vacuo to give a crude red oil. The crude products were purified via column chromatography using hexane:ethyl acetate (1:1 to 1:99) to afford 44 (43 mg, 18%) as a red oil and 41 as a red oil (210 mg, 82%).

3-(Ethylthio)-1-methoxy-6-methylphenazine (39). Yield: 31%; 51 mg was isolated as a yellow solid (NAS method A). $^1$H NMR (600 MHz, CDCl$_3$): δ 8.14 (dd, J=8.4, 1.8 Hz, 1H), 7.63-7.55 (m, 2H), 7.50 (d, J=1.8 Hz, 1H), 6.81 (d, J=1.8 Hz, 1H), 4.11 (s, 3H), 3.16 (q, J=7.4 Hz, 2H), 2.84 (s, 3H), 1.46 (t, J=7.4 Hz, 3H). $^{13}$C NMR (151 MHz, CDCl$_3$): δ 154.4, 143.8, 143.3, 142.1, 141.7, 137.3, 135.6, 130.3, 129.4, 128.2, 115.1, 107.0, 56.6, 26.3, 17.8, 13.8. HRMS (ESI): calc. for C$_{16}$H$_{17}$N$_2$OS [M+H]$^+$: 285.1056, found: 285.1069. MP: 89-91° C.

2-((4-Methoxy-9-methylphenazin-2-yl)thio)ethan-1-ol (40). Yield: 52%; 96 mg was isolated as a yellow solid (NAS method A). $^1$H NMR (500 MHz, CDCl$_3$): δ 8.20 (m, 1H), 7.83 (s, 1H), 7.74-7.65 (m, 2H), 6.91 (d, J=2.0 Hz, 1H), 4.16 (s, 3H), 4.01 (t, J=6.2 Hz, 2H), 3.42 (t, J=6.2 Hz, 2H), 2.92 (s, 3H). $^{13}$C NMR (126 MHz, CDCl$_3$): δ 154.8, 143.6, 143.4, 142.0, 140.6, 137.4, 135.7, 130.6, 129.9, 128.3, 116.3, 107.4, 60.6, 56.8, 35.4, 17.9. HRMS (ESI): calc. for C$_{16}$H$_{17}$N$_2$O$_2$S [M+H]$^+$: 301.1005, found: 301.1016. MP: 158-160° C.

3-((2,5,8,11-Tetraoxatridecan-13-yl)thio)-1-methoxy-6-methylphenazine (41). Yield: 82%; 210 mg was isolated as a red residue (NAS method B). $^1$H NMR (600 MHz, CDCl$_3$): δ 8.18 (m, 1H), 7.72-7.63 (m, 3H), 6.89 (d, J=1.7 Hz, 1H), 4.14 (s, 3H), 3.88 (t, J=6.6 Hz, 2H), 3.72-3.66 (m, 6H), 3.66-3.60 (m, 4H), 3.54-3.51 (m, 2H), 3.40 (t, J=6.6 Hz, 2H), 3.36 (s, 3H), 2.90 (s, 3H). $^{13}$C NMR (151 MHz, CDCl$_3$): δ 154.6, 143.3, 142.9, 142.2, 141.9, 137.1, 135.8, 130.8, 129.7, 128.3, 115.2, 107.3, 72.1, 70.9, 70.8, 70.8, 70.7, 69.4, 59.2, 56.8, 32.1, 18.0. Note: 1 HRMS (ESI): calc. for C$_{23}$H$_{31}$N$_2$O$_5$S [M+H]$^+$: 447.1948, found: 447.1940.

3-(Ethylthio)-6-methylphenazin-1-ol (42). Yield: 37%; 58 mg was isolated as a yellow solid (NAS method A). $^1$H NMR (500 MHz, CDCl$_3$): δ 8.13 (s, 1H), 7.93 (dd, J=7.4, 2.5 Hz, 1H), 7.64-7.58 (m, 2H), 7.46 (d, J=1.9 Hz, 1H), 7.04 (d, J=1.9 Hz, 1H), 3.16 (q, J=7.4 Hz, 2H), 2.86 (s, 3H), 1.48 (t, J=7.4 Hz, 3H). $^{13}$C NMR (126 MHz, CDCl$_3$): δ 151.1, 144.1, 143.6, 143.4, 140.6, 137.8, 133.5, 130.2, 129.7, 127.1, 114.0, 108.9, 26.3, 18.0, 13.9. HRMS (ESI): calc. C$_{15}$H$_{15}$N$_2$OS for [M+H]$^+$: 271.0900, found: 271.0896. MP: 119-121° C.

3-((2-Hydroxyethyl)thio)-6-methylphenazin-1-ol (43). Yield: 75%; 44 mg was isolated as a yellow solid (NAS method B). $^1$H NMR (600 MHz, DMSO-d$_6$): 10.72 (br. s, 1H), 8.06 (m, 1H), 7.79-7.73 (m, 2H), 7.46 (d, J=2.0 Hz, 1H), 7.02 (d, J=2.0 Hz, 1H), 5.13 (t, J=5.6 Hz, 1H), 3.73 (q, J=5.7 Hz, 2H), 3.28 (t, J=6.6 Hz, 2H), 2.81 (s, 3H). $^{13}$C NMR (151 MHz, DMSO-d$_6$): δ 153.0, 143.2, 142.8, 142.5, 140.7, 136.7, 134.6, 130.4, 129.6, 127.3, 112.6, 109.8, 59.5, 33.7, 17.4. HRMS (ESI): calc. for C$_{15}$H$_{15}$N$_2$O$_2$S [M+H]$^+$: 287.0849, found: 287.0855. MP: 154-156° C.

3-((2,5,8,11-Tetraoxatridecan-13-yl)thio)-6-methylphenazin-1-ol (44). Yield: 18%; 43 mg was isolated as a red residue (NAS method B). $^1$H NMR (600 MHz, DMSO-d$_6$): δ 10.73 (br. s, 1H), 8.06 (m, 1H), 7.78-7.74 (m, 2H), 7.46 (d, J=1.8 Hz, 1H), 7.03 (d, J=1.8 Hz, 1H), 3.76 (t, J=6.3 Hz, 2H), 3.59 (dd, J=5.9, 3.5 Hz, 2H), 3.54 (dd, J=5.9, 3.5 Hz, 2H), 3.51 (dd, J=5.9, 3.5 Hz, 2H), 3.49-3.45 (m, 4H), 3.40-3.38 (m, 4H), 3.20 (s, 3H), 2.80 (s, 3H). $^{13}$C NMR (151 MHz, DMSO-d$_6$): δ 153.1, 143.1, 142.5, 142.5, 140.7, 136.7, 134.6, 130.3, 129.6, 127.3, 112.9, 109.8, 71.3, 69.8, 69.8, 69.6, 68.6, 58.0, 30.9, 17.4. HRMS (ESI): calc. for C$_{22}$H$_{29}$N$_2$O$_5$S [M+H]$^+$: 433.1792, found: 433.1800.

General Procedures for Bromination of 3-Chloro-1-Hydroxyphenazines to Target HPs.

Bromination reaction method A (synthesis of 28-33, 35, 37 and 45). Compound 27 (100 mg, 0.28 mmol) and N-bromosuccinimide (104 mg, 0.59 mmol) were dissolved with dichloromethane (75 mL) in a round bottom flask. The resulting reaction mixture was then allowed to stir at room temperature for 3 hours until complete. After this time, the contents of the reaction were transferred to a separatory funnel with brine and extracted with dichloromethane. The organic layer extracts were collected, dried with sodium sulfate, filtered, and concentrated in vacuo. The resulting solid was purified via column chromatography using 100% dichloromethane to elute 37 (107 mg, 74%) as a yellow solid.

Bromination reaction method B (synthesis of 34, 36, 46 and 47). Compound 24 (102 mg, 0.34 mmol) was dissolved in toluene (7 mL) before N-bromosuccinimide (133 mg, 0.75 mmol) was added to the solution. The resulting reaction mixture was then heated to 50° C. for 6 hours until complete. After this time, the reaction mixture was cooled to room temperature and concentrated via rotavap. The crude material was then absorbed onto silica gel (dry loaded) and purified via column chromatography using 100% dichloromethane to elute 34 (98 mg, 63%) as a yellow solid.

2,4-Dibromo-3-chlorophenazin-1-ol (28). Yield: 46%; 31 mg was isolated as a yellow solid (method A). $^1$H NMR (400 MHz, DMSO-d$_6$): δ 8.37 (m, 1H), 8.32 (m, 1H), 8.11-8.03 (m, 2H). $^{13}$C NMR (101 MHz, DMSO-d$_6$): δ 152.2, 143.4, 141.2, 139.7, 137.2, 133.9, 132.7, 132.3, 129.4, 128.9, 112.5, 106.1. HRMS (DART): calc. for C$_{12}$H$_6$Br$_2$ClN$_2$O [M+H]$^+$: 388.8509, found: 388.8525. MP: 218-220° C. HPLC purity: 99.5%.

2,4-Dibromo-3-chloro-6-methylphenazin-1-ol (29). Yield: 75%; 434 mg was isolated as a yellow solid (method A). $^1$H NMR (400 MHz, DMSO-d$_6$): δ 11.91 (s, 1H), 8.16 (d, J=8.4 Hz, 1H), 7.95-7.85 (m, 2H), 2.85 (s, 3H). $^{13}$C NMR (101 MHz, DMSO-d$_6$): δ 152.0, 142.7, 141.4, 138.6, 137.4, 136.7, 133.4, 132.1, 131.4, 126.6, 112.9, 106.1, 16.9. HRMS (DART): calc. for $C_{13}H_8Br_2ClN_2O$ [M+H]$^+$: 402.8665, found: 402.8671. MP: 216-218° C. HPLC purity: 98.8%.

2,4-Dibromo-3-chloro-6,7-dimethylphenazin-1-ol (30). Yield: 72%; 112 mg was isolated as a yellow solid (method A). $^1$H NMR (400 MHz, DMSO-d$_6$): δ 11.66 (br. s, 1H), 8.06 (d, J=8.9 Hz, 1H), 7.84 (d, J=8.9 Hz, 1H), 2.80 (s, 3H), 2.57 (s, 3H). $^{13}$C NMR (101 MHz, DMSO-d$_6$): δ 151.8, 142.4, 140.0, 139.7, 138.3, 136.3, 135.6, 133.7, 132.4, 125.3, 112.8, 105.3, 20.1, 12.6. HRMS (DART): calc. for $C_{14}H_{10}Br_2ClN_2O$ [M+H]$^+$: 416.8822, found: 416.8816. MP: 223-225° C. HPLC purity: 95.5%.

2,4,7-Tribromo-3-chloro-6-methylphenazin-1-ol (31). Yield: 33%; 51 mg was isolated as a yellow solid (method A). $^1$H NMR (500 MHz, DMSO-d$_6$): δ 8.12 (d, J=9.3 Hz, 1H), 8.07 (d, J=9.3 Hz, 1H), 2.92 (s, 3H). $^{13}$C NMR (101 MHz, DMSO-d$_6$): δ 151.9, 142.5, 140.2, 138.8, 137.5, 136.9, 135.7, 133.2, 127.6, 127.1, 112.7, 106.4, 16.9. HRMS (DART): calc. for $C_{13}H_7Br_3ClN_2O$ [M+H]$^+$: 478.7792, found: 478.7801. MP: 243-245° C. HPLC purity: >99.9%.

2,4-Dibromo-3-chloro-6-phenoxyphenazin-1-ol (32). Yield: 38%; 47 mg was isolated as a yellow solid (method A). $^1$H NMR (500 MHz, DMSO-d$_6$): δ 8.11 (d, J=8.7 Hz, 1H), 7.96 (t, J=8.2 Hz, 1H), 7.44 (t, J=7.8 Hz, 2H), 7.40 (d, J=7.6 Hz, 1H), 7.26-7.16 (m, 3H). $^{13}$C NMR (151 MHz, DMSO-d$_6$): δ 156.8, 152.7, 152.1, 142.2, 138.9, 137.2, 133.9, 132.1, 130.1, 124.1, 123.6, 119.3, 117.5, 112.9, 106.6. HRMS (DART): calc. for $C_{18}H_{10}Br_2ClN_2O_2$[M+H]$^+$: 478.8792, found: 478.8813. MP: 239-241° C. HPLC purity: 98.1%.

2,4-Dibromo-3-chloro-8-fluorophenazin-1-ol (33). Yield: 73%; 89 mg was isolated as a yellow solid (method A). $^1$H NMR (500 MHz, DMSO-d$_6$): δ 12.02 (br. s, 1H), 8.39 (dd, J=9.5, 5.9 Hz, 1H), 8.04 (ddd, J=9.5, 8.2, 2.7 Hz, 1H), 8.00 (dd, J=9.5, 2.7 Hz, 1H). $^{13}$C NMR (126 MHz, DMSO-d$_6$): δ 163.2 (d, J=255.6 Hz), 151.9, 141.7 (d, J=14.2 Hz), 141.1, 139.2 (d, J=1.8 Hz), 137.0, 134.1, 132.4 (d, J=10.7 Hz), 124.3 (d, J=28.4 Hz), 112.6, 111.1 (d, J=21.5 Hz), 106.9. HRMS (ESI): calc. $C_{12}H_3Br_2ClFN_2O$ for [M–H]$^-$: 402.8290, found: 402.8286. MP: 236-238° C. HPLC purity: 99.6%.

2,4-Dibromo-3,6,8-trichlorophenazin-1-ol (34). Yield: 63%; 98 mg was isolated as a yellow solid (method B). $^1$H NMR (500 MHz, DMSO-d$_6$): δ 8.39 (d, J=2.1 Hz, 1H), 8.28 (d, J=2.1 Hz, 1H). $^{13}$C NMR (126 MHz, DMSO-d$_6$): δ 152.2, 141.4, 139.5, 138.7, 138.4, 135.8, 134.7, 133.7, 132.1, 126.6, 112.6, 107.8. HRMS (DART): calc. for $C_{12}H_4Br_2Cl_3N_2O$ [M+H]$^+$: 458.7703, found: 458.7696. MP: 246-248° C. HPLC purity: 99.9%.

2,4,6-Tribromo-3-chlorophenazin-1-ol (35). Yield: 38%; 30 mg was isolated as an orange solid (method A). $^1$H NMR (500 MHz, DMSO-d$_6$): δ 8.45 (dd, J=7.3, 0.7 Hz, 1H), 8.35 (dd, J=8.8, 0.7 Hz, 1H), 7.93 (dd, J=8.6, 7.3 Hz, 1H). $^{13}$C NMR (101 MHz, DMSO-d$_6$): δ 152.1, 141.9, 140.6, 139.8, 138.0, 135.5, 134.3, 132.4, 129.0, 123.5, 112.7, 107.1. HRMS (ESI): calc. for $C_{12}H_3Br_3ClN_2O$ [M–H]$^-$: 462.7490, found: 462.7486. MP: 193-195° C. HPLC purity: >99.9%.

2,4,8-Tribromo-3-chlorophenazin-1-ol (36). Yield: 36%; 46 mg was isolated as a yellow solid (method A). $^1$H NMR (400 MHz, DMSO-d$_6$): δ 8.55 (d, J=2.1 Hz, 1H), 8.26 (d, J=9.3 Hz, 1H), 8.17 (dd, J=9.3, 2.1 Hz, 1H). $^{13}$C NMR (101 MHz, DMSO-d$_6$): δ 151.9, 142.0, 141.3, 139.7, 137.5, 135.5, 134.1, 131.1, 130.4, 125.5, 112.5, 106.8. HRMS (ESI): calc. for $C_{12}H_3Br_3ClN_2O$ [M–H]$^-$: 462.7490, found: 462.7469. MP: 250° C. (decomp). HPLC purity: 98.9%.

2,4-Dibromo-3-chloro-8-iodophenazin-1-ol (37). Yield: 74%; 107 mg was isolated as an orange solid (method A). $^1$H NMR (600 MHz, DMSO-d$_6$): δ 8.76 (d, J=1.8 Hz, 1H), 8.28 (dd, J=9.1, 1.8 Hz, 1H), 8.07 (d, J=9.1 Hz, 1H). $^{13}$C NMR (101 MHz, DMSO-d$_6$): δ 152.2, 142.4, 141.7, 140.7, 139.8, 137.6, 137.2, 133.9, 130.7, 112.7, 106.8, 100.4. HRMS (ESI): calc. for $C_{12}H_3Br_2ClIN_2O$ [M–H]$^-$: 510.7351, found: 510.7351. MP: 258-260° C. HPLC purity: 99.7%.

2,4-Dibromo-3-(ethylthio)-6-methylphenazin-1-ol (45). Yield: 73%; 35 mg was isolated as a yellow solid (method A). $^1$H NMR (500 MHz, CDCl$_3$): δ 8.62 (s, 1H), 8.09 (d, J=8.5 Hz, 1H), 7.81 (dd, J=8.5, 7.0 Hz, 1H), 7.76 (d, J=7.0 Hz, 1H), 3.17 (q, J=7.4 Hz, 2H), 2.99 (s, 3H), 1.32 (t, J=7.3 Hz, 3H). $^{13}$C NMR (126 MHz, CDCl$_3$): δ 149.1, 144.5, 141.9, 140.2, 139.3, 139.3, 133.2, 132.5, 131.1, 126.6, 124.2, 111.5, 31.4, 17.7, 14.9. HRMS (DART): calc. for $C_{15}H_{13}Br_2N_2OS$ [M+H]$^+$: 428.9090, found: 428.9094. MP: 163-165° C. HPLC purity: 97.8%.

2,4-Dibromo-3-((2-hydroxyethyl)thio)-6-methylphenazin-1-ol (46). Yield: 28%; 25 mg was isolated as a yellow solid (method B). $^1$H NMR (600 MHz, DMSO-d$_6$): δ 11.52 (br. s, 1H), 8.16 (d, J=8.6 Hz, 1H), 7.91 (dd, J=8.6, 6.8 Hz, 1H), 7.87 (d, J=6.8 Hz, 1H), 4.88 (br. s, 1H), 3.59 (t, J=7.1 Hz, 2H), 3.17 (t, J=7.1 Hz, 2H), 2.87 (s, 3H). $^{13}$C NMR (151 MHz, DMSO-d$_6$): δ 150.8, 142.8, 141.5, 139.7, 138.6, 137.6, 134.2, 132.3, 131.1, 126.5, 122.0, 112.3, 60.5, 38.9, 17.0. HRMS (ESI): calc. for $C_{15}H_{11}Br_2N_2O_2S$ [M–H]$^-$: 442.8893, found: 442.8905. MP: 178-180° C. HPLC purity: 95.7%.

3-((2,5,8,11-Tetraoxatridecan-13-yl)thio)-2,4-dibromo-6-methylphenazin-1-ol (47). Yield: 27%; 16 mg was isolated as a yellow residue (method B). $^1$H NMR (600 MHz, CDCl$_3$): δ 8.66 (br. s, 1H), 8.09 (d, J=8.6 Hz, 1H), 7.82 (dd, J=8.6, 6.7 Hz, 1H), 7.76 (d, J=6.7 Hz, 1H), 3.71 (t, J=6.8 Hz, 2H), 3.62-3.54 (m, 10H), 3.51 (dd, J=5.8, 3.6 Hz, 2H), 3.36 (s, 3H), 3.32 (t, J=6.8 Hz, 2H), 2.98 (s, 3H). $^{13}$C NMR (151 MHz, CDCl$_3$): δ 149.2, 144.5, 141.9, 140.2, 139.3, 139.3, 133.2, 132.6, 131.1, 126.6, 124.2, 111.3, 72.1, 70.8, 70.8, 70.7, 70.7, 70.6, 70.5, 59.2, 36.6, 17.7. HRMS (ESI): calc. for $C_{22}H_{27}Br_2N_2O_5S$ [M+H]$^+$: 590.9983, found: 590.9992. HPLC purity: >99.9%.

Compound No. 150. $^1$H NMR (500 MHz, CDCl$_3$): δ 8.78 (br. s, 1H), 8.44-8.38 (m, 1H), 8.30-8.24 (m, 1H), 8.00-7.92 (m, 2H). $^{13}$C NMR (100 MHz, CDCl$_3$): δ 149.9, 145.1, 141.6, 140.5, 132.8, 132.5, 132.4, 132.3, 130.5, 129.0, 117.2, 107.7. HRMS (DART): calc. $C_{12}H_6Br_3N_2O$ for [M+H]$^+$: 432.8005, found: 432.8018. MP: 222-224° C.

(b) UV-vis for HPs binding iron(II).[36-38] Halogenated phenazine-iron(II) complex formation was determined using UV-vis spectrometry. Ammonium iron(II) sulfate hexahydrate (0.5 equivalent) was added to a stirring solution of an HP analogue (10 mM for HPs 18, 28 and 29; 5 mM for HP 34) in dimethyl sulfoxide. Aliquots of 50 μL (HPs 18, 28, and 29) or 100 μL (HP 34) were then removed from the resulting mixture and added to 1 mL dimethyl sulfoxide in a cuvette. Spectral scanning was performed from 200 to 800 nm in 2 nm increments and a loss of absorbance at $\lambda_{max}$ (free HP) in the UV-vis spectrum and apparent formation of a halogenated phenazine-iron(II) complex was observed over time. The disappearance of HPs 28, 29 and 34 was observed over the indicated time points and the halogenated phenazine-iron(II) complex formation (in a 2:1 HP:iron(II) ratio) yielded a loss in absorbance due to precipitation.

(c) pKa determination of select HP analogues.[36] Dissociation constants (pKa) for select HP analogues were determined using UV-vis spectroscopy and the Henderson-Hasselbalch equation. Buffers were prepared using potassium phosphate monobasic (KH$_2$PO$_4$) and sodium phosphate dibasic (NaHPO$_4$) in a 1:1 solution of water:methanol to achieve a pH range of 4.07 to 9.66 (ammonium hydroxide was added to prepare buffer pH over 9.80). Compounds were added from 10 mM stock solutions in dimethyl sulfoxide (25 µL) to 1975 µL of each buffer to each evaluate analogue to yield a final compound concentration of 125 µM. Full spectral scans were performed from 200 to 800 nm in 2 nm increments to determine $\lambda_{max}$ values for the protonated phenol (HA) and the deprotonated phenolate species (A⁻). The change in absorption at each determined $\lambda_{max}$ in relation to pH was monitored in each buffer and plotted as absorbance versus pH for each species. The pKa was first estimated by determining the pH of the point of intersection of the two linear curves. The visual estimation was confirmed by plotting pH versus log [A⁻/HA]. The resulting plot yielded a linear regression line with a Y-intercept corresponding to a calculated pKa value. As a method validation, the pKa of 4-nitrophenol (lit. pKa=7.15) was determined to be 7.52 under these experimental parameters.

Biological Studies. This section includes: (a) in vitro testing of HP analogues, and (b) in vivo testing of HP 29.

(a) In Vitro Testing of HP Analogues.

Minimum Inhibitory Concentration (MIC) Susceptibility Assay for MRSA-1707, MRSA-44, MRSE 35984, VRE 700221 and *E. faecalis* OG1RF.[33-38] The minimum inhibitory concentration (MIC) for each test compound was determined by the broth microdilution method as recommended by the Clinical and Laboratory Standards Institute (CLSI).[58] In a 96-well plate, eleven two-fold serial dilutions of each compound were made in a final volume of 100 µL Lysogeny Broth (LB, MRSA-1707, MRSA-44 and MRSE 35984; Brain Heart Infusion, BHI, VRE 700221 and *E. faecalis* OG1RF). Each well was inoculated with ~10⁵ bacterial cells at the initial time of incubation, prepared from a fresh log phase culture ($OD_{600}$ of 0.5 to 1.0 depending on bacterial strain). The MIC was defined as the lowest concentration of compound that prevented bacterial growth after incubating 16 hours at 37° C. (MIC values were further supported by spectrophotometric readings at $OD_{600}$). The concentration range tested for each HP compound during this study was 0.05 to 50 µM. DMSO served as our vehicle and negative control in each microdilution MIC assay. DMSO was serially diluted with a top concentration of 0.5% v/v. All compounds were tested in a minimum of three independent experiments.

MIC Assay for *Mycobacterium tuberculosis* (Mtb) H37Ra (ATCC 25177).[35-38] *M. tuberculosis* H37Ra (ATCC 25177) was inoculated in 10 mL Middlebrook 7H9 medium and allowed to grow for two weeks. The culture was then diluted with fresh medium to an $OD_{600}$=0.01. Aliquots of 200 µL were then added to each well of a 96-well plate starting from the second column. Test compounds were dissolved in DMSO at final concentration of 10 mM. 7.5 µL of each compound along with DMSO (negative control) and streptomycin (positive control-40 mg/ml stock solution) were added to 1.5 mL of the diluted cultures, resulting in 50 µM final concentration of each halogenated phenazine analogues and 340 µM for streptomycin. The final DMSO concentration was maintained at 0.5%. Aliquots of 400 µL were added to wells of the first column of the 96-well plate and serially diluted two-fold (200 µL) per well across the plate to obtain final concentrations that ranges from 0.024 to 50 µM for the test compounds and 0.16 to 340 µM for streptomycin. The plates were then incubated at 37° C. for seven days. Minimum inhibitory concentrations are reported as the lowest concentration at which no bacterial growth was observed. $OD_{600}$ absorbance was recorded using SpectraMax M5 (Molecular Devices). All compounds were tested in a minimum of three independent experiments.

MIC Assay for Mtb CDC1551. A bioluminescent *Mycobacterium tuberculosis* CDC1551 reporter strain (Mtb-lux) was grown in Middlebrook 7H9 media supplemented with 0.05% Tween 80 and 10% oleic acid-albumin-dextrose-catalase (OADC) under kanamycin (50 µg/mL) selection until an optical density ($OD_{600}$) of 0.4-0.8. A 2-fold serial drug dilution series (0.003-200 µM) was prepared at 2× in media with 2% dimethyl sulfoxide (DMSO) in 15 µL in white 384-well plates (white with solid bottom, Corning #3570). Mtb-lux was diluted to $OD_{600}$ 0.02 and added to the drug dilution plate (15 µL/well). Luminescence was measured with a Synergy H4 plate reader after 5 days of treatment (37° C., 5% $CO_2$) and compared to negative control (1% DMSO) and positive control (10 µM rifampicin) used to calculate % inhibition of growth. Dose-response curves were generated using GraphPad Prism and MIC values were determined using a modified Gompertz model.

MIC Assay for *Streptococcus pneumoniae* (ATCC 6303). The MIC of 29 against *Streptococcus pneumoniae* ATCC 6303 was determined according to the following procedure. Fresh overnight cultures were inoculated at 1% in microtiter wells containing tryptic soy broth with 5% sheep blood in the presence of 29 ranging from 0.5 nM to 1000 nM. The plate was incubated at 37° C. with 5% $CO_2$ for 16-20 hours. After this time, the lowest test concentration of 29 that resulted in a complete lack of turbidity (bacterial growth) was determined to be the MIC. All tests were performed in at least three independent experiments.

Calgary Biofilm Device (CBD) Experiments.[36-38] Biofilm eradication experiments were performed using the CBD to determine MBC/MBEC values for various compounds of interest (Innovotech, product code: 19111). The CBD (96-well plate with lid containing pegs to establish biofilms) was inoculated with 125 µL of a mid-log phase culture diluted 1,000-fold in tryptic soy broth with 0.5% glucose (TSBG; BHI for *E. faecalis* OG1RF) to establish bacterial biofilms after incubation at 37° C. for 24 hours. The lid was then removed, washed and transferred to another 96-well plate containing 2-fold serial dilutions of the test compounds (the "challenge plate"). The total volume of media with compound in each well in the challenge plate is 150 µL. The CBD device was incubated at 37° C. for 24 hours, the lid then removed from the challenge plate and MBC/MBEC values determined using different experimental pathways. To determine MBC values, 20 µL of the challenge plate was transferred into a fresh 96-well plate containing 180 µL TSBG (BHI for *E. faecalis* OG1RF) and incubated overnight at 37° C. The MBC values were determined as the concentration giving a lack of visible bacterial growth (i.e., turbidity). For determination of MBEC values, the CBD lid (with attached pegs/treated biofilms) was transferred to a new 96-well plate containing 150 µL of fresh TSBG (BHI for *E. faecalis* OG1RF) media in each well and incubated for 24 hours at 37° C. to allow viable biofilms to grow and disperse resulting in turbidity after the incubation period. MBEC values were determined as the lowest test concentration that resulted in eradicated biofilm (i.e., wells that had no turbidity after final incubation period). In selected experiments, both treated and untreated CBD pegs were removed from the lid after final incubation, sonicated for 30 minutes in phosphate-buffered saline (PBS) and plated out to determine biofilm cell killing in colony forming units per peg (CFU/peg). All data were obtained from a minimum of three independent experiments.

RT-qPCR Protocol to Determine Iron Starvation in MRSA Biofilms.[39] Biofilm Formation: MRSA BAA-1707 was grown in TSBG to an $OD_{600}$~0.8-1.0. Then 1 mL of this culture was added to 24-well plate coated with 0.1% gelatin. The plate was then incubated for 20 hours at 37° C. under static conditions to form biofilms. Following biofilm formation, the contents of the well was discarded leaving only the biofilm. Treating Established Biofilms with Compounds: HPs 3, 28 and 29 was added to established MRSA BAA-1707 biofilms in TSBG at the desired concentration (1 µM or 1/10 MBEC value). In addition, the same volume of DMSO (vehicle) was added as a negative control. The plate was then incubated under static conditions for 20 hours at 37° C. After the incubation period, the liquid culture was discarded leaving only the surface-attached biofilm. Extraction of Total RNA from MRSA BAA-1707 Biofilms: 0.5 mL of RNA protect Bacteria Reagent (Qiagen) was added for 5 minutes to the plate and the biofilm suspension scraped and transferred into 2 mL tubes. The bacterial cells were then centrifuged for 1 minute at 15,000×g, then the supernatant was removed. Total RNA was extracted using the RiboPure RNA Purification Kit, Bacteria (Invitrogen, cat #AM1925) according to the manufacturer's protocols. Genomic DNA was digested using the materials supplied by the kit. Each experiment was performed in three replicates. RNA Quality Control Information: RNA concentration was determined on Qubit® 2.0 Fluorometer (ThermoFisher/Invitrogen, Grand Island, NY), RNA quality was assessed using the Agilent 2100 Bioanalyzer (Agilent Technologies, Inc.). Total RNA with RNA integrity numbers (RIN)≥7 were used for RT-qPCR validation. Quantitative Real-Time PCR (qPCR) for Select Gene Transcripts (Validation): Total RNA was isolated from MRSA BAA-1707 biofilms treated and untreated with HPs. Real-time PCR reactions were performed using the Power SYBR Green RNA-to-$C_T$ 1-Step Kit (Applied Biosystems 4389986) using the manufacturer's guidelines. SYBR, Primers Rt enzyme RNA and water were added to a 1.5 mL Eppendorf tube on ice. After all contents were added to Eppendorf tubes, they were mixed by centrifugation for 1 minute at 10,000×g. 20 µL were then removed from the reaction tubes and were added to each well of a MicroAmp Optical 96-Well Reaction Plate with Barcode (Applied Biosystems 4306737) on ice. The plate was then sealed with MicoAmp Optical Adhesive Film (Applied Biosystems 4311971). The plate was centrifuged for 2 minutes at 1200× g. qPCR was carried out on an ABI 7300 sequence detection system using the thermocycler program: 30 minutes at 50° C., 10 minutes at 95° C., 15 seconds at 95° C. (40 cycles) and 1 minute at 60° C. Relative gene expression changes were calculated using the ΔΔCT method. For each experiment, the CT values of each gene tested were normalized to the CT values of the housekeeping gene ptaA. Graphs and data analysis were performed using the GraphPad Prism 6. All qPCR data were generated from three independent experiments.

Lactate Dehydrogenate (LDH) Release Assay for HeLa Cytotoxicity Assessment.[46] HeLa cytotoxicity was assessed using the LDH release assay described by CytoTox96 (Promega G1780). HeLa cells were grown in DMEM (Gibco) supplemented with 10% FBS at 37° C. with 5% $CO_2$. When the HeLa cultures exhibited 70-80% confluence, halogenated phenazines were then diluted by DMEM (10% FBS) at concentrations of 25, 50 and 100 µM and added to HeLa cells. Triton X-100 (at 2% v/v) was used as the positive control for maximum LDH activity in this assay (i.e., complete cell death) while "medium only" lanes served as negative control lanes (i.e., no cell death). DMSO was used as our vehicle control. HeLa cells were treated with compounds for 24 hours and then 50 µL of the supernatant was transferred into a fresh 96-well plate where 50 µL of the reaction mixture was added to the 96-well plate and incubated at room temperature for 30 minutes. Finally, stop solution (50 µL) was added to the incubating plates and the absorbance was measured at 490 nm. Results are from three independent experiments.

Cytotoxicity Assay against J774 Macrophages and HepG2 Cells.[47] J774 macrophages and HepG2 cells were grown in Dulbecco's Modified Eagle Medium (DMEM; Gibco) supplemented with 10% heat-inactivated fetal calf serum (Atlanta Biologicals), 2 mM L-glutamine, 1 mM sodium pyruvate, 100 U/mL penicillin, and 100 mg/mL streptomycin in T75 flasks until confluent. J774 macrophages were scraped in PBS, pelleted at 1000 rpm for 10 minutes, and resuspended in macrophage infection media (DMEM+10% Fetal Bovine Serum, FBS, 1% L-glutamine, and 1% sodium pyruvate, no phenol red). HepG2 cells were lifted with 0.25% trypsin, pelleted at 1000 rpm for 10 min, and resuspended in macrophage infection media. Both cell types were seeded into 384-well plates (black with clear bottom, Corning #3712) at 25,000 cells/well (in 24 µL total volume). After 4 hours of attachment (37° C., 5% CO2), 6 µL of 5× drugs (2-fold dilution series spanning 0.003-200 µM test concentrations, prepared in water) was added to each well. Cells were treated overnight (16-18 hours), followed by addition of 6 µL/well Alamar Blue (0.02% resazurin in water). After 4 hours, fluorescence was measured using a Synergy $H_4$ plate reader ($\lambda_{ex}$=530 nm/$\lambda_{em}$=590 nm). Viability was calculated as a percent of DMSO control. 2% Triton X-100 was used as a positive control.

Cytotoxicity Assay against HEK-293 Cells.[48] The viability of HEK-293 cells was assessed by the MTT assay. The cells were cultured in DMEM medium containing 10% fetal bovine serum and 100 U/mL penicillin and streptomycin. The cells ($10^4$ cells/well) were seeded onto a 96-well plate and maintained at 37° C. in a humidified incubator under 5% CO2 overnight. Serial concentrations of 29 (final concentrations at 0, 1.56, 3.13, 6.25, 12.5, 25, 50, 100 and 200 µM) were then added to the wells (n=6). After incubation at 37° C. for 72 hours, 10 µL of MTT (5 mg/mL) in PBS was added to each well and incubated for 4 hours, followed by the aspiration of the medium. Dimethyl sulfoxide (DMSO, 100 µL) was then added to each well to dissolve the MTT in the wells, and the plate was agitated for 1 hour. The optical density (OD) was measured at 570 nm using a UV/vis microplate spectrophotometer (BioTek). The percent inhibition was calculated as follows: Inhibition (%)=(1−test $OD_{570}$/non-treated $OD_{570}$)×100%. The data were analyzed by Origin. Hemolysis Assay with Red Blood Cells. Freshly drawn human red blood cells (hRBC with ethylenediaminetetraacetic acid (EDTA) as an anticoagulant) were washed with Tris-buffered saline (0.01M Tris-base, 0.155 M sodium chloride (NaCl), pH 7.2) and centrifuged for 5 minutes at 3,500 rpm. The washing was repeated three times with the buffer. In 96-well plate, test compounds were added to the buffer from DMSO stocks. Then 2% hRBCs (50 µL) in buffer were added to test compounds to give a final concentration of 200 µM. The plate was then incubated for 1 hour at 37° C. After incubation, the plate was centrifuged for 5 minutes at 3,500 rpm before 80 µL of the supernatant was transferred to another 96-well plate to obtain an optical density (OD) read at 405 nm. DMSO served as the negative control (0% hemolysis) while Triton X served as the positive control (100% hemolysis) in these experiments. The percent hemolysis was calculated as ($OD_{405}$ of the compound treated RBCs−$OD_{405}$ DMSO control)/($OD_{405}$ Triton X treated RBCs−$OD_{405}$ buffer) from three independent experiments.

(b) In Vivo Testing of HP 29 for Efficacy.

Preparation of Polyethylene Glycol (PEG) ointment. PEG ointments were prepared based on reported procedures with minor modifications.[52] For these investigations, PEG ointment base was prepared by mixing PEG 400 (70%, wt/vol) with PEG 3350 (30%, wt/vol) as described by the U.S. Pharmacopeia and The National Formulary (USP 24-NF 19). PEG 400 (7 mL) was added to a flask containing PEG 3550 (3 g) and the resulting mixture was heated at 60° C. until the mixture liquified. Then, 1 mL of the resulting PEG liquid was transferred to a vial containing HP 29 (20 mg) to create a 2% suspension. The mixture was then allowed to stir at 60° C. for 30 min before being cooled to room temperature where the suspension solidified. A similar procedure was used to create vehicle control (without 29).

Bacterial Strains Used in Animal Models of Infection. *Staphylococcus aureus* strain UAMS-1, a well-characterized antibiotic susceptible clinical isolate commonly used to study the organism's biofilm formation and colonization properties, was used in animal experiments during these studies.[59] Female BALB/c mice 4 to 6 weeks of age were obtained from Charles River Laboratories International, Inc. (Wilmington, MA) and housed individually according to approved University of Rochester Medical Center Council on Animal Research (UCAR) protocol UCAR-101864/2017-022. The UAMS-1 wound infection experiments were performed by the Dunman lab at the University of Rochester Medical Center.

*Enterococcus faecalis* strain OG1RF was used in animal experiments during these investigations. Seven-week old female C57BL/6J mice were purchased from Jackson Laboratories Ltd. and housed according to the University of Florida's approved IACUC protocol 201709769. The OG1RF wound infection experiments were performed by the Lemos lab at the University of Florida.

*S. aureus* Dermal Wound Infection Model. The effects of ointment compilations were evaluated for in vivo antimicrobial activity using a dermal wound infection mouse model, as previously described.[52] Briefly, mice were anesthetized by intraperitoneal injection with a mixture of 100 mg kg$^{-1}$ Ketamine (Hospira Inc., Lake Forest IL) and 10 mg kg$^{-1}$ Xylazine (Lloyd Laboratories, Shenandoah IA) in PBS. Two mg kg$^{-1}$ meloxicam (Henry Schein Animal Health, Portland, ME) was administered prior to dermal wounding. The dorsal mid-section of the mouse was shaved and cleaned with a series of betadine scrub (Fisher Scientific), povidone-iodine pads (Professional Disposables International Inc; Orangeburg, NY) and isopropyl alcohol pads (Fisher Scientific) for a total contact time of two minutes. A wound was created in this sterile field on the mouse with a 4.5 mm biopsy punch (Fisher Scientific) to remove only the dermal layer and not disrupt the underlying musculature. The wounds of the mice were inoculated with 1×10$^7$ *S. aureus* strain UAMS-1 by pipetting 10 µL of culture directly onto the wound. Mice were then treated with ointment formulations (50 µL) containing either vehicle alone, or test compound 45 minutes post inoculation; treatments were repeated every 12 hours for consecutive three days. Mice were then euthanized via $CO_2$ asphyxiation and cervical dislocation. The wound and underlying muscle was excised with a 7 mm biopsy punch and placed in microcentrifuge tubes containing 1.4 mm ceramic beads (Fisher Scientific) and 1 mL of freshly made PBS. Samples were homogenized for 1 minute using the Fisherbrand bead mill homogenizer, serially diluted, and plated on ChromoAgar plates. Plates were incubated for 16 hours at 37° C. and the number of *S. aureus* enumerated.

*E. faecalis* Dorsal Wound Infection Model. To test the efficacy of HP 29 for the treatment of wounds infected with *Enterococcus faecalis*, a 3 mm incision dorsal wound was created using a biopsy punch on seven-week old female C57BL/6J mice and the wound infected with 20 µL of 6×10$^{10}$ CFU/mL of *E. faecalis* OG1RF, and the infected wound covered with Tegaderm® (Tegaderm, 3M, St Paul Minnesota). 24-Hours after infection, the dressing was removed and the wounds treated topically with HP 29 ointment, or with the PEG vehicle control once a day. On day 3 (2 days of treatment) post-infection, animals were euthanized and the wounds aseptically excised using a surgical blade and the tissues homogenized in 1 mL of sterile PBS. The homogenates were serially diluted and plated on trypticase soy (TSA) agar containing rifampicin and fusidic acid for bacterial enumeration.

Abbreviations

1-OHP: 1-Hydroxyphenaizne; BHI: brain heart infusion; BSA: Bis(trimethylsilyl)acetamide; CBD: Calgary biofilm device; CFU: colony forming unit; C Log P: calculated logarithm of partition coefficient between n-octanol and water; $CO_2$: carbon dioxide; d: day; DMEM: Dulbecco's Modified Eagle Medium; DMF: N:N-dimethylformamide; EDTA: ethylenediaminetetraacetic acid; FBS: Fetal Bovine Serum; h: hour; HP: halogenated phenazine; hRBCs: human red blood cells; LB: Lysogeny Broth; LDH: lactate dehydrogenase; MBC: minimum bactericidal concentration; MBEC: minimum biofilm eradication concentration; MIC: minimum inhibitory concentration; µM: micromolar; min: minute; MRSA: methicillin-resistant *Staphylococcus aureus*; MRSE: methicillin-resistant *Staphylococcus epidermidis*; Mtb: *Mycobacterium tuberculosis*; NAS: nucleophilic aromatic substitution; NBS: N-bromosuccinimide; OD: optical density; PBS: phosphate buffered saline; PEG: polyethylene glycol; pKa dissociation constant; QAC-10: quaternary ammonium cation-10; rt: room temperature; RT-qPCR: real-time quantitative polymerase chain reaction; SI: selectivity index; TPEN: N,N,N',N'-tetrakis(2-pyridinylmethyl)-1,2-ethanediamine); TSA: trypticase soy agar; TSB: tryptic soy broth; TSBG: tryptic soy broth supplemented with 0.5% glucose; VRE: vancomycin-resistant *Enterococcus faecium*.

REFERENCES

1) Y. Abouelhassan, A. T. Garrison, H. Yang, A. Chávez-Riveros, G. M. Burch and R. W. Huigens III, Recent Progress in Natural-Product-Inspired Programs Aimed at Addressing Antibiotic Resistance and Tolerance, J Med Chem. 2019, 62, 7618-7642.
2) Lewis K. The Science of Antibiotic Discovery. Cell 2020, 181, 29-45.
3) Wood, T. K. Combatting Bacterial Persister Cells. Biotechnol. Bioeng. 2016, 113, 476-483.
4) M. A. Fitzpatrick, Real-World Antibiotic Needs for Resistant Gram-Negative Infections. Lancet Infect Dis. 2020, 20, 1108-1109.
5) Liu K, Huigens III R W. Instructive Advances in Chemical Microbiology Inspired by Nature's Diverse Inventory of Molecules. ACS Infect Dis. 2020, 6, 541-562.
6) Lewis, K. Platforms for Antibiotic Discovery. Nat. Rev. Drug Discov. 2013, 12, 371-387.
7) Brown, E. D.; Wright, G. D. Antibacterial Drug Discovery in the Resistance Era. Nature 2016, 529, 336-343.

8) Blair, J. M. A.; Webber, M. A.; Baylay, A. J.; Ogbolu, D. O.; Piddock, L. J. V. Molecular Mechanisms of Antibiotic Resistance. Nat. Rev. Microbiol. 2015, 13, 42-51.

9) Munita, J. M.; Arias, C. A. Mechanisms of Antibiotic Resistance. Microbiol. Spectr. 2016, 4, VMBF-0016-2015.

10) Wright, G. D. Molecular Mechanisms of Antibiotic Resistance. Chem. Commun. 2011, 47, 4055-4061.

11) Miller, M. B.; Bassler, B. L. Quorum Sensing in Bacteria. Annu. Rev. Microbiol. 2001, 55, 165-199.

12) Waters, C. M.; Bassler, B. L. Quorum Sensing: Cell-to-Cell Communication in Bacteria. Annu. Dev. Biol. 2005, 21, 319-346.

13) Mukherjee, S.; Bassler, B. L. Bacterial Quorum Sensing in Complex and Dynamically Changing Environments. Nat. Rev. Microbiol. 2019, 17, 371-382.

14) Lewis, K. Persister Cells. Annu. Rev. Microbiol. 2010, 64, 357-372.

15) Donlan, R. M.; Costerton, J. W.; Donlan, R. M.; Costerton, J. W. Biofilms: Survival Mechanisms of Clinically Relevant Microorganisms. Clin. Microbiol. 2002, 15, 167-193.

16) Hall-Stoodley, L.; Costerton, J. W.; Stoodley, P. Bacterial Biofilms: From the Natural Environment to Infectious Diseases. Nat. Rev. Microbiol. 2004, 2, 95-108.

17) Flemming, H. C.; Wingender, J.; Szewzyk, U.; Steinberg, P.; Rice, S. A.; Kjelleberg, S. Biofilms: An Emergent Form of Bacterial Life. Nat. Rev. Microbiol. 2016, 14, 563-575.

18) Yan, J.; Bassler, B. L. Surviving as a Community: Antibiotic Tolerance and Persistence in Bacterial Biofilms. Cell Host Microbe 2019, 26, 15-21.

19) Lewis, K. Persister Cells: Molecular Mechanism Related to Antibiotic Tolerance. Handb. Exp. Pharmacol. 2012, 211, 121-133.

20) Garrison, A. T.; Huigens III, R. W. Eradicating Bacterial Biofilms with Natural Products and Their Inspired Analogues That Operate Through Unique Mechanisms. Curr. Top. Med. Chem. 2017, 17, 1954-1964.

21) Wolcott, R.; Dowd, S. The Role of Biofilms: Are We Hitting the Right Target? Plast. Reconstr. Surg. 2011, 127, 28S-35S.

22) Bjarnsholt, T. The Role of Bacterial Biofilms in Chronic Infections. APMIS Suppl. 2013, 121, 1-51.

23) Wu, Y. K.; Cheng, N. C.; Cheng, C. M. Biofilms in Chronic Wounds: Pathogenesis and Diagnosis. Trends Biotechnol. 2019, 37, 505-517.

24) Ling, L. L.; Schneider, T.; Peoples, A. J.; Spoering, A. L.; Engels, I.; Conlon, B. P.; Mueller, A.; Schaberle, T. F.; Hughes, D. E.; Epstein, S.; Jones, M.; Lazarides, L.; Steadman, V. A.; Cohen, D. R.; Felix, C. R.; Fetterman, K. A.; Millett, W. P.; Nitti, A. G.; Zullo, A. M.; Chen, C.; Lewis, K. A New Antibiotic Kills Pathogens without Detectable Resistance. Nature 2015, 517, 455-459.

25) Imai, Y.; Meyer, K. J.; Iinishi, A.; Favre-Godal, Q.; Green, R.; Manuse, S.; Caboni, M.; Mori, M.; Niles, S.; Ghiglieri, M.; Honrao, C.; Ma, X.; Guo, J. J.; Makriyannis, A.; Linares-Otoya, L.; Böhringer, N.; Wuisan, Z. G.; Kaur, H.; Wu, R.; Mateus, A.; Typas, A.; Savitski, M. M.; Espinoza, J. L.; O'Rourke, A.; Nelson, K. E.; Hiller, S.; Noinaj, N.; Schaberle, T. F.; D'Onofrio, A.; Lewis, K. A New Antibiotic Selectively Kills Gram-Negative Pathogens. Nature 2019, 576, 459-464.

26) Smith, P. A.; Koehler, M. F. T.; Girgis, H. S.; Yan, D.; Chen, Y.; Chen, Y.; Crawford, J. J.; Durk, M. R.; Higuchi, R. I.; Kang, J.; Murray, J.; Paraselli, P.; Park, S.; Phung, W.; Quinn, J. G.; Roberts, T. C.; Rougé, L.; Schwarz, J. B.; Skippington, E.; Wai, J.; Xu, M.; Yu, Z.; Zhang, H.; Tan, M. W.; Heise, C. E. Optimized Arylomycins are a New Class of Gram-Negative Antibiotics. Nature 2018, 561, 189-194.

27) Richter, M. F.; Drown, B. S.; Riley, A. P.; Garcia, A.; Shirai, T.; Svec, R. L.; Hergenrother, P. J. Predictive Compound Accumulation Rules Yield a Broad-Spectrum Antibiotic. Nature 2017, 545, 299-304.

28) Parker, E. N.; Drown, B. S.; Geddes, E. J.; Lee, H. Y.; Ismail, N.; Lau, G. W.; Hergenrother, P. J. Implementation of Permeation Rules Leads to FabI Inhibitor with Activity against Gram-Negative Pathogens. Nat. Microbiol. 2020, 5, 67-75.

29) Motika, S. E.; Ulrich, R. J.; Geddes, E. J.; Lee, H. Y.; Lau, G. W.; Hergenrother, P. J. Gram-Negative Antibiotic Active Through Inhibition of an Essential Riboswitch. J. Am. Chem. Soc. 2020, 142, 10856-10862.

30) Li, Q.; Pellegrino, J.; Lee, D. J.; Tran, A. T.; Chaires, H. A.; Wang, R.; Park, J. E.; Ji, K.; Chow, D.; Zhang, N.; Brilot, A. F.; Biel, J. T.; van Zundert, G.; Borrelli, K.; Shinabarger, D.; Wolfe, C.; Murray, B.; Mulle, E.; Chesneau, O.; Jacobson, M. P.; Fraser, J. S.; Seiple, I. B. Synthetic Group A Streptogramin Antibiotics that Overcome Vat Resistance. Nature 2020, 586, 145-150.

31) Conlon, B. P.; Nakayasu, E. S.; Fleck, L. E.; LaFleur, M. D.; Isabella, V. M.; Coleman, K.; Leonard, S. N.; Smith, R. D.; Adkins, J. N.; Lewis, K. Activated ClpP Kills Persisters and Eradicates a Chronic Biofilm Infection. Nature 2013, 503, 365-370.

32) Kim, W.; Zhu, W.; Hendricks, G. L.; Van Tyne, D.; Steele, A. D.; Keohane, C. E.; Fricke, N.; Conery, A. L.; Shen, S.; Pan, W.; Lee, K.; Rajamuthiah, R.; Fuchs, B. B.; Vlahovska, P. M.; Wuest, W. M.; Gilmore, M. S.; Gao, H.; Ausubel, F. M.; Mylonakis, E. A New Class of Synthetic Retinoid Antibiotics Effective against Bacterial Persisters. Nature 2018, 556, 103-107.

33) Borrero, N. V.; Bai, F.; Perez, C.; Duong, B. Q.; Rocca, J. R.; Jin, S.; Huigens III, R. W. Phenazine Antibiotic Inspired Discovery of Potent Bromophenazine Antibacterial Agents against *Staphylococcus aureus* and *Staphylococcus epidermidis*. Org. Biomol. Chem. 2014, 12, 881-886.

34) Garrison, A. T.; Bai, F.; Abouelhassan, Y.; Paciaroni, N. G.; Jin, S.; Huigens III, R. W. Bromophenazine Derivatives with Potent Inhibition, Dispersion and Eradication Activities against *Staphylococcus aureus* Biofilms. RSC Adv. 2015, 5, 1120-1124.

35) Garrison, A. T.; Abouelhassan, Y.; Kallifidas, D.; Bai, F.; Ukhanova, M.; Mai, V.; Jin, S.; Luesch, H.; Huigens III, R. W. Halogenated Phenazines that Potently Eradicate Biofilms, MRSA Persister Cells in Non-Biofilm Cultures and *Mycobacterium tuberculosis*. Angew. Chem. Int. Ed. 2015, 54, 14819-14823.

36) Garrison, A. T.; Abouelhassan, Y.; Norwood I V, V. M.; Kallifidas, D.; Bai, F.; Nguyen, M.; Rolfe, M.; Burch, G. M.; Jin, S.; Luesch, H.; Huigens III, R. W. Structure-Activity Relationships of a Diverse Class of Halogenated Phenazines that Targets Persistent, Antibiotic-Tolerant Bacterial Biofilms and *Mycobacterium tuberculosis*. J. Med. Chem. 2016, 59, 3808-3825.

37) Yang, H.; Abouelhassan, Y.; Burch, G. M.; Kallifidas, D.; Huang, G.; Yousaf, H.; Jin, S.; Luesch, H.; Huigens III, R. W. A Highly Potent Class of Halogenated Phenazine Antibacterial and Biofilm-Eradicating Agents Accessed Through a Modular Wohl-Aue Synthesis. Sci. Rep. 2017, 7, 2003.

38) Garrison, A. T.; Abouelhassan, Y.; Kallifidas, D.; Tan, H.; Kim, Y. S.; Jin, S.; Luesch, H.; Huigens III, R. W. An Efficient Buchwald-Hartwig/Reductive Cyclization for the Scaffold Diversification of Halogenated Phenazines: Potent Antibacterial Targeting, Biofilm Eradication and Prodrug Exploration. J. Med. Chem. 2018, 61, 3962-3983.
39) Abouelhassan, Y.; Zhang, Y.; Jin, S.; Huigens III, R. W. Transcript Profiling of MRSA Biofilms Treated with a Halogenated Phenazine Eradicating Agent: A Platform for Defining Cellular Targets and Pathways Critical to Biofilm Survival. Angew. Chem. Int. Ed. 2018, 57, 15523-15528.
40) Machan, Z. A.; Pitt, T. L.; White, W.; Watson, D.; Taylor, G. W.; Cole, P. J.; Wilson, R. Interaction Between *Pseudomonas aeruginosa* and *Staphylococcus aureus*: Description of an Antistaphylococcal Substance. J. Med. Microbiol. 1991, 34, 213-217.
41) Laursen, J. B.; Nielsen, J. Phenazine Natural Products: Biosynthesis, Synthetic Analogues, and Biological Activity. Chem. Rev. 2004, 104, 1663-1685.
42) Price-Whelan, A.; Dietrich, L. E. P.; Newman, D. K. Rethinking "Secondary" Metabolism: Physiological Roles for Phenazine Antibiotics. Nat. Chem. Biol. 2006, 2, 71-78.
43) Guttenberger, N.; Blankenfeldt, W.; Breinbauer, R. Recent Developments in the Isolation, Biological Function, Biosynthesis, and Synthesis of Phenazine Natural Products. Bioorg. Med. Chem. 2017, 25, 6149-6166.
44) Kwast, A.; Stachowska, K.; Trawczyński, A.; Wróbel, Z. N-Aryl-2-Nitrosoanilines as Intermediates in the Synthesis of Substituted Phenazines from Nitroarenes. Tetrahedron Lett. 2011, 52, 6484-6488.
45) Wróbel, Z.; Plichta, K.; Kwast, A. Tetrahedron 2017, 73, 3147-3152.
46) Weidmann, E.; Brieger, J.; Jahn, B.; Hoelzer, D.; Bergmann, L.; Mitrou, P. S. Lactate Dehydrogenase-Release Assay: A Reliable, Nonradioactive Technique for Analysis of Cytotoxic Lymphocyte-Mediated Lytic Activity against Blasts from Acute Myelocytic Leukemia. Annu. Hematol. 1995, 70, 153-158.
47) Gupta, R.; Rodrigues Felix, C.; Akerman, M. P.; Akerman, K. J.; Slabber, C. A.; Wang, W.; Adams, J.; Shaw, L. N.; Tse-Dinh, Y. C.; Munro, O. Q.; Rohde K. H. Evidence for Inhibition of Topoisomerase 1A by Gold(III) Macrocycles and Chelates Targeting *Mycobacterium tuberculosis* and *Mycobacterium abscessus*. Antimicrob. Agents Chemother. 2018, 62, No. e01696.
48) Abouelhassan, Y.; Zhang, P.; Ding, Y.; Huigens III, R. W. Rapid Kill Assessment of an N-arylated NH125 Analogue against Drug-Resistant Microorganisms. Med. Chem. Commun. 2019, 10, 712-716.
49) Ceri, H.; Olson, M. E.; Stremick, C.; Read, R. R.; Morck, D.; Buret, A. The Calgary Biofilm Device: New Technology for Rapid Determination of Antibiotic Susceptibilities of Bacterial Biofilms. J. Clin. Microbiol. 1999, 37, 1771-1776.
50) Harrison, J. J.; Stremick, C. A.; Turner, R. J.; Allan, N. D.; Olson, M. E.; Ceri, H. Microtiter Susceptibility Testing of Microbes Growing on Peg Lids: A Miniaturized Biofilm Model for High-Throughput Screening. Nat. Protoc. 2010, 5, 1236-1254.
51) Jennings, M. C.; Ator, L. E.; Paniak, T. J.; Minbiole, K. P. C.; Wuest, W. M. Biofilm-Eradicating Properties of Quaternary Ammonium Amphiphiles: Simple Mimetics of Antimicrobial Peptides. ChemBioChem 2014, 15, 2211-2215.
52) Blanchard, C.; Brooks, L.; Beckley, A.; Colquhoun, J.; Dewhurst, S.; Dunman, P. M. Neomycin Sulfate Improves the Antimicrobial Activity of Mupirocin-Based Antibacterial Ointments. Antimicrob. Agents Chemother. 2016, 60, 862-872.
53) Colomer-Winter, C.; Flores-Mireles, A. L.; Baker, S. P.; Frank, K. L.; Lynch, A. J. L.; Hultgren, S. J.; Kitten, T.; Lemos, J. A. Manganese acquisition is essential for virulence of *Enterococcus faecalis*. PLoS Pathog. 2018, 14, e1007102.
54) Bhattacharya, M.; Wozniak, D. J.; Stoodley, P.; Hall-Stoodley, L. Prevention and Treatment of *Staphylococcus aureus* Biofilms. Expert Rev. Anti. Infect. Ther. 2015, 13, 1499-1516.
55) Ch'ng, J. H.; Chong, K. K. L.; Lam, L. N.; Wong, J. J.; Kline, K. A. Biofilm-associated Infection by Enterococci. Nat. Rev. Microbiol. 2019, 17, 82-94.
56) Xiao, T.; Liu, K.; Huigens III, R. W. Progress Towards a Stable Cephalosporin-Halogenated Phenazine Conjugate for Antibacterial Prodrug Applications. Bioorg. Med. Chem. Lett. 2020, 30, 127515.
57) Yang, H.; Liu, K.; Jin, S.; Huigens III, R. W. Design, Synthesis and Biological Evaluation of a Halogenated Phenazine-Erythromycin Conjugate Prodrug for Antibacterial Applications. Org. Biomol. Chem. 2021, DOI: 10.1039/d0ob02428g.
58) Methods for dilution antimicrobial susceptibility tests for bacteria that grow aerobically; approved standards, 8th ed. (M7-M8); Clinical and Laboratory Standards Institute: Wayne, PA, 2009.
59) Gillaspy, A. F.; Hickmon, S. G.; Skinner, R. A.; Thomas, J. R.; Nelson, C. L.; Smeltzer, M. S. Role of the Accessory Gene Regulator (arg) in Pathogenesis of Staphylococcal Osteomyelitis. Infect. Immun. 1995, 63, 3373-3380.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I):

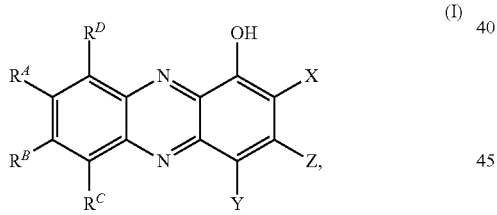

or a salt, solvate, hydrate, tautomer, stereoisomer, or isotopically labeled compound thereof, wherein:
X is hydrogen, halogen, substituted or unsubstituted alkyl, substituted or unsubstituted alkenyl, or substituted or unsubstituted alkynyl;
Z is chloro, substituted methyl, substituted or unsubstituted, $C_{2-12}$ alkyl, substituted or unsubstituted alkenyl, substituted or unsubstituted alkynyl, —$OR^3$, —$N(R^4)_2$, —$SR^5$, —SCN, —C(=$NR^5$)$R^5$, —C(=$NR^5$)$OR^5$, —C(=$NR^5$)$N(R^5)_2$, —C(=O)H, —C(=O)N($R^5$)$_2$, —$NO_2$, —$NR^5$C(=O)$R^5$, —$NR^5$C(=O)$OR^5$, —$NR^5$C(=O)N($R^5$)$_2$, —OC(=O)$R^5$, —OC(=O)$OR^5$, or —OC(=O)N($R^5$)$_2$, wherein:
$R^3$ is substituted or unsubstituted acyl, substituted methyl, substituted or unsubstituted, $C_{2-12}$ alkyl, substituted or unsubstituted alkenyl, substituted or unsubstituted alkynyl, substituted or unsubstituted carbocyclyl, substituted or unsubstituted hetero-cyclyl, substituted or unsubstituted aryl, or substituted or unsubstituted heteroaryl;
each instance of $R^4$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, or substituted or unsubstituted heteroaryl, or two instances of $R^4$ are joined to form a substituted or unsubstituted heteroaryl ring; and
each instance of $R^5$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^5$ are joined to form a substituted or unsubstituted heterocyclic or substituted or unsubstituted heteroaryl ring;
Y is hydrogen, halogen, substituted or unsubstituted alkyl, substituted or unsubstituted alkenyl, or substituted or unsubstituted alkynyl;
each of $R^A$, $R^B$, $R^C$, and $R^D$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^1$, —$N(R^1)_2$, —$SR^1$, —CN, —SCN, —C(=$NR^1$)$R^1$, —C(=$NR^1$)$OR^1$, —C(=$NR^1$)N($R^1$)$_2$, —C(=O)$R^1$, C(=O)$OR^1$, —C(=O)N($R^1$)$_2$, —$NO_2$, —$NR^1$C(=O)$R^1$, —$NR^1$C(=O)$OR^1$, —$NR^1$C(=O)N($R^1$)$_2$, —OC(=O)$R^1$, —OC(=O)$OR^1$, or —OC(=O)N($R^1$)$_2$, wherein each instance of $R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^1$ are joined to form a substituted or unsubstituted heterocyclic or substituted or unsubstituted heteroaryl ring;
each carbon atom substituent is, independently, selected from halogen, —CN, —$NO_2$, —$N_3$, —$SO_2H$, —$SO_3H$, —OH, —$OR^{aa}$, —ON($R^{bb}$)$_2$, —N($R^{bb}$)$_2$, —N($R^{bb}$)$_3^+X^-$, —N($OR^{cc}$)$R^{bb}$, —SH, —$SR^{aa}$, —$SSR^{cc}$, —C(=O)$R^{aa}$, —$CO_2H$, —CHO, —C($OR^{cc}$)$_2$, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)N($R^{bb}$)$_2$, —OC(=$NR^{bb}$)N($R^{bb}$)$_2$, —$NR^{bb}$C(=$NR^{bb}$)N($R^{bb}$)$_2$, —C(=O)$NR^{bb}SO_2R^{aa}$, —$NR^{bb}SO_2R^{aa}$, —$SO_2N$ $(R^{bb})_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —OP(=O)(R$^{aa}$)$_2$, —OP(=O)(OR$^{cc}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^c$)$_2$, —OP(R$^{cc}$)$_3$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; or two geminal hydrogen atoms on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each nitrogen atom substituent is, independently, a nitrogen protecting group, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, or 5-14 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each oxygen atom substituent is, independently, substituted or unsubstituted $C_{1-6}$ alkyl, —C(=O)R$^{aa}$, —CO$_2$R$^{aa}$, —C(=O)N(R$^{bb}$)$_2$, or an oxygen protecting group;

each sulfur atom substituent is, independently, substituted or unsubstituted $C_{1-6}$ alkyl, —C(=O)R$^{aa}$, —CO$_2$R$^{aa}$, —C(=O)N(R$^{bb}$)$_2$, or a sulfur protecting group;

each nitrogen protecting group is independently selected from the group consisting of formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4', 8'-dimethoxynaphthylmethyl)benzenesulfonamide (DNMBS), benzylsulfonamide, trifluoromethylsulfonamide, phenacylsulfonamide, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl groups, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each oxygen protecting group is independently selected from the group consisting of methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4 (1,1,3,3-tetramethylbutyl)phenoxyacetate, 2,4-bis(1,1- dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, tosylate (Ts), —$R^{aa}$, —N($R^{bb}$)$_2$, —C(=O)S$R^{aa}$, —C(=O)$R^{aa}$, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N(Rb)$_2$, —S(=O)$R^{aa}$, —SO$_2$$R^{aa}$, —Si($R^{aa}$)$_3$, —P($R^{cc}$)$_2$, —P($R^{cc}$)$_3$, —P(=O)($R^{aa}$)$_2$, —P(=O)(O$R^{cc}$)$_2$, and —P(=O)(N$R^{bb}$)$_2$;

each sulfur protecting group is independently selected from the group consisting of —$R^{aa}$, —N($R^{bb}$)$_2$, —C(=O)S$R^{aa}$, —C(=O)$R^{aa}$, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2$$R^{aa}$, —Si($R^{aa}$)$_3$, —P($R^{cc}$)$_2$, —P($R^{cc}$)$_3$, —P(=O)($R^{aa}$)$_2$, —P(=O)(O$R^{cc}$)$_2$, and —P(=O)(N$R^{bb}$)$_2$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SOR$^{aa}$, —C(=S)N($R^{cc}$)$_2$, —C(=O)S$R^{cc}$, —C(=S)S$R^{cc}$, —P(=O)($R^{aa}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$ X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, and 5-10 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ groups are joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, and 5-10 membered heteroaryl, or two R" groups are joined to form a 3-10 membered heterocyclyl or 5-10 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{gg}$ is, independently, selected from halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$ X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC (=S)SC$_{1-6}$ alkyl, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, and 5-10 membered heteroaryl; or two geminal R$^{gg}$ groups are joined to form =O or =S;

X$^-$ is a counterion;

each counterion is independently a halide ion, NO$_3^-$, ClO$_4^-$, OH$^-$, H$_2$PO$_4^-$, HCO$_3^-$, HSO$_4^-$, a sulfonate ion, a carboxylate ion, BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, a carborane anion, CO$_3^{2-}$, HPO$_4^{2-}$, PO$_4^{3-}$, B$_4$O$_7^{2-}$, SO$_4^{2-}$, S$_2$O$_3^{2-}$, or a carboxylate anion;

unless otherwise provided, each carbocyclyl is independently a radical of a non-aromatic, monocyclic, fused polycyclic, bridged polycyclic, or spiro polycyclic hydrocarbon group having from 3 to 14 ring carbon atoms, zero heteroatoms, and zero or more carbon-carbon double or triple bonds in the non-aromatic ring system;

unless otherwise provided, each heterocyclyl or heterocyclic ring is independently a radical of a 3- to 14-membered, non-aromatic, monocyclic, fused polycyclic, bridged polycyclic, or spiro polycyclic ring system having ring carbon atoms, 1 to 4 ring heteroatoms, and zero or more carbon-carbon double or triple bonds, wherein each heteroatom is independently selected from nitrogen, oxygen, and sulfur;

unless otherwise provided, each heteroaryl is independently a radical of a 5- to 14-membered, monocyclic or polycyclic, aromatic ring system having ring carbon atoms and 1-4 ring heteroatoms provided in the aromatic ring system, wherein each heteroatom is independently selected from nitrogen, oxygen, and sulfur; and each acyl is derived from a carboxylic acid;

provided that when Z is chloro:
  X is halogen, substituted or unsubstituted alkyl, substituted or unsubstituted alkenyl, or substituted or unsubstituted alkynyl;
  Y is substituted or unsubstituted alkyl, substituted or unsubstituted alkenyl, or substituted or unsubstituted alkynyl;
  R$^A$ is not hydrogen;
  R$^B$ is not hydrogen;
  R$^C$ is not hydrogen; or
  R$^D$ is not hydrogen.

2. The compound of claim 1, or a salt, solvate, hydrate, tautomer, stereoisomer, or isotopically labeled compound thereof, wherein the compound is of the formula:

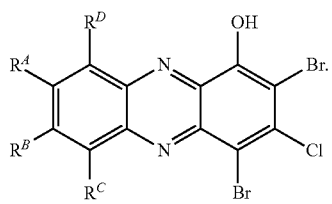

3. The compound of claim 1, or a salt, solvate, hydrate, tautomer, stereoisomer, or isotopically labeled compound thereof, wherein the compound is of the formula:

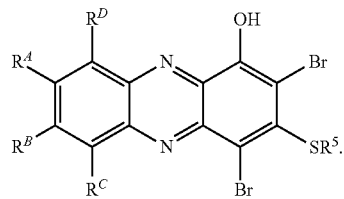

4. The compound of claim 1, or a salt, solvate, hydrate, tautomer, stereoisomer, or isotopically labeled compound thereof, wherein the compound is of the formula:

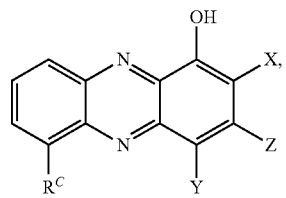

provided that R$^C$ is not hydrogen.

5. The compound of claim 1, or a salt, solvate, hydrate, tautomer, stereoisomer, or isotopically labeled compound thereof, wherein the compound is of the formula:

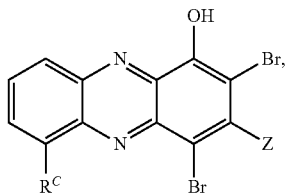

provided that R$^C$ is not hydrogen.

6. The compound of claim 1, or a salt, solvate, hydrate, tautomer, stereoisomer, or isotopically labeled compound thereof, wherein the compound is of the formula:

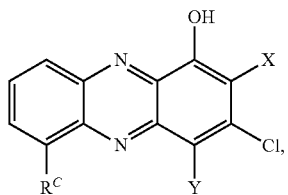

provided that R$^C$ is not hydrogen.

7. The compound of claim 1, or a salt, solvate, hydrate, tautomer, stereoisomer, or isotopically labeled compound thereof, wherein the compound is of the formula:

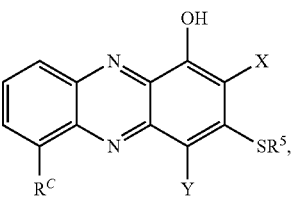

provided that R$^C$ is not hydrogen.

8. The compound of claim 1, or a salt, solvate, hydrate, tautomer, stereoisomer, or isotopically labeled compound thereof, wherein Z is substituted methyl, substituted or unsubstituted, $C_{2-12}$ alkyl, substituted or unsubstituted alkenyl, substituted or unsubstituted alkynyl, —OR$^3$, —N(R$^4$)$_2$, —SR$^5$, —SCN, —C(=NR$^5$)R$^5$, —C(=NR$^5$)OR$^5$, —C(=NR$^5$)N(R$^5$)$_2$, —C(=O)H, —C(=O)N(R$^5$)$_2$, —NO$_2$, —NR$^5$C(=O)R$^5$, —NR$^5$C(=O)OR$^5$, —NR$^5$C(=O)N(R$^5$)$_2$, —OC(=O)R$^5$, —OC(=O)OR$^5$, or —OC(=O)N(R$^5$)$_2$.

9. The compound of claim 1, or a salt, solvate, hydrate, tautomer, stereoisomer, or isotopically labeled compound thereof, wherein Z is chloro.

10. The compound of claim 1, or a salt, solvate, hydrate, tautomer, stereoisomer, or isotopically labeled compound thereof, wherein Z is —SR$^5$.

11. The compound of claim 1, or a salt, solvate, hydrate, tautomer, stereoisomer, or isotopically labeled compound thereof, wherein the compound is of the formula:

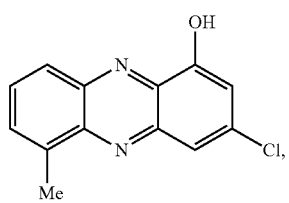

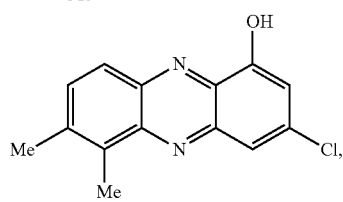

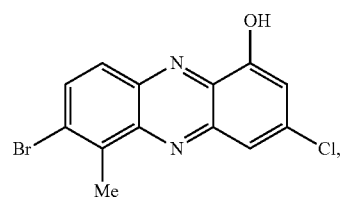

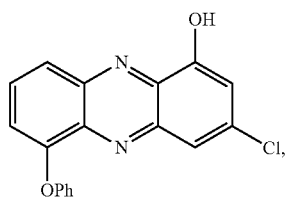

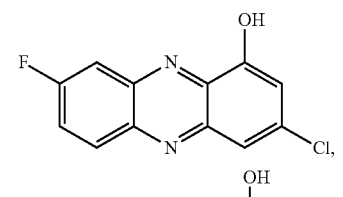

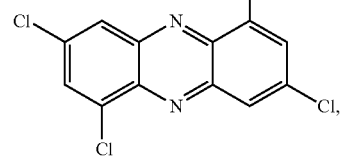

-continued

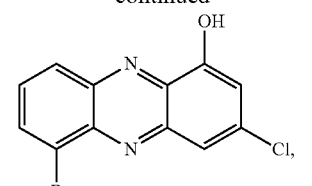

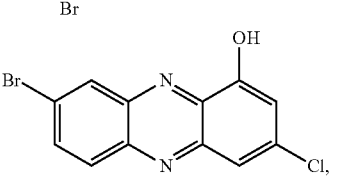

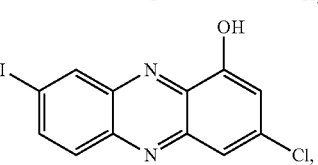

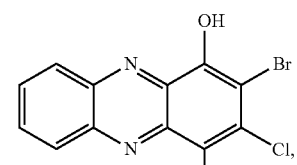

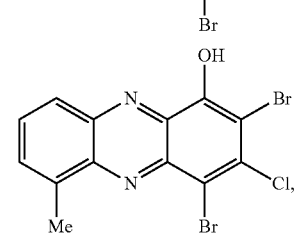

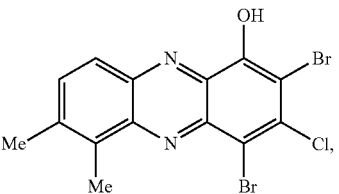

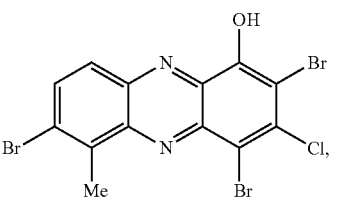

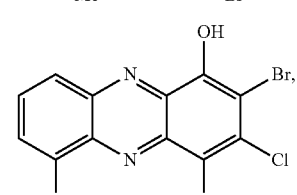

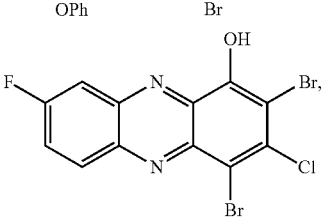

-continued

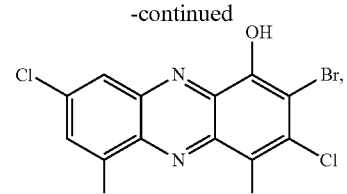
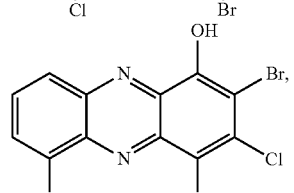
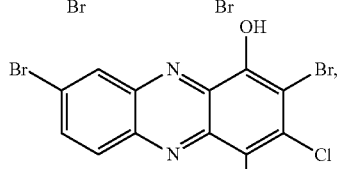
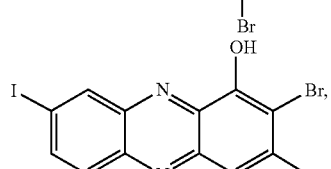
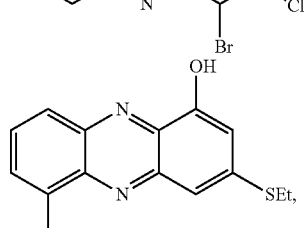
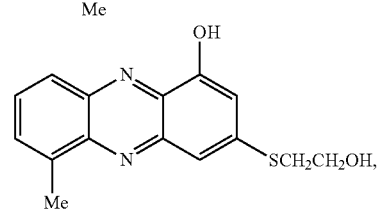
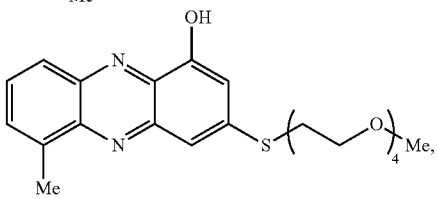
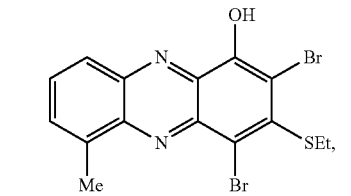
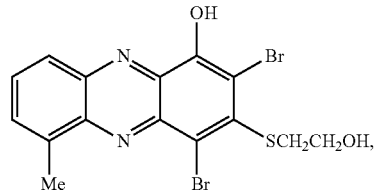

-continued

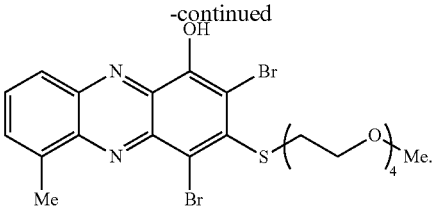

12. A compound, or a salt, solvate, hydrate, tautomer, stereoisomer, or isotopically labeled compound thereof, wherein the compound is of the formula:

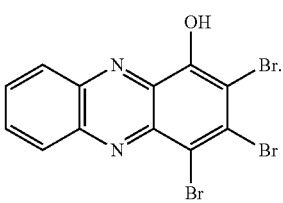 [SMILES: Oc1c(Br)c(Br)c(Br)c2nc3ccccc3nc12]

13. The compound of claim 1, or a pharmaceutically acceptable salt thereof.

14. A composition comprising:
   the compound of claim 1, or a salt, solvate, hydrate, tautomer, stereoisomer, or isotopically labeled compound thereof; and
   an excipient.

15. A kit comprising:
   the compound of claim 1, or a salt, solvate, hydrate, tautomer, stereoisomer, or isotopically labeled compound thereof; and
   instructions for using the compound, or a salt, solvate, hydrate, tautomer, stereoisomer, or isotopically labeled compound thereof.

16. A method of treating a bacterial infection in a subject in need thereof, the method comprising administering to the subject in need thereof an effective amount of a compound of claim 1, or a pharmaceutically acceptable salt, solvate, hydrate, tautomer, stereoisomer, or isotopically labeled compound thereof.

17. A method of inhibiting the formation of a bacterial biofilm, inhibiting the growth of a bacterial biofilm, reducing a bacterial biofilm, or clearing a bacterial biofilm, the method comprising contacting the bacterial biofilm with an effective amount of a compound of claim 1, or a pharmaceutically acceptable salt, solvate, hydrate, tautomer, stereoisomer, or isotopically labeled compound thereof.

18. A method of inhibiting the growth of a bacterium, inhibiting the reproduction of a bacterium, inhibiting the viability of a bacterium, or killing a bacterium, the method comprising contacting the bacterium with an effective amount of a compound of claim 1, or a salt, solvate, hydrate, tautomer, stereoisomer, or isotopically labeled compound thereof.

19. A method of disinfecting a surface with respect to a bacterium on the surface, the method comprising contacting the surface with an effective amount of a compound of claim 1, or a pharmaceutically acceptable salt, solvate, hydrate, tautomer, stereoisomer, or isotopically labeled compound thereof.

20. The compound of claim 1, or a salt, solvate, hydrate, tautomer, stereoisomer, or isotopically labeled compound thereof, wherein Z is —S(substituted or unsubstituted alkyl).

21. The compound of claim 1, or a salt, solvate, hydrate, tautomer, stereoisomer, or isotopically labeled compound thereof, wherein X is hydrogen.

22. The compound of claim 1, or a salt, solvate, hydrate, tautomer, stereoisomer, or isotopically labeled compound thereof, wherein X is halogen.

23. The compound of claim 1, or a salt, solvate, hydrate, tautomer, stereoisomer, or isotopically labeled compound thereof, wherein Y is hydrogen.

24. The compound of claim 1, or a salt, solvate, hydrate, tautomer, stereoisomer, or isotopically labeled compound thereof, wherein Y is halogen.

25. The compound of claim 1, or a salt, solvate, hydrate, tautomer, stereoisomer, or isotopically labeled compound thereof, wherein $R^A$ is hydrogen, halogen, or substituted or unsubstituted alkyl.

26. The compound of claim 1, or a salt, solvate, hydrate, tautomer, stereoisomer, or isotopically labeled compound thereof, wherein $R^B$ is hydrogen, halogen, or substituted or unsubstituted alkyl.

27. The compound of claim 1, or a salt, solvate, hydrate, tautomer, stereoisomer, or isotopically labeled compound thereof, wherein $R^C$ is hydrogen, halogen, substituted or unsubstituted alkyl, or —$OR^1$.

28. The compound of claim 1, or a salt, solvate, hydrate, tautomer, stereoisomer, or isotopically labeled compound thereof, wherein $R^D$ is hydrogen, halogen, or substituted or unsubstituted alkyl.

29. The compound of claim 11, or a pharmaceutically acceptable salt thereof.

30. The compound of claim 12, or a pharmaceutically acceptable salt thereof.

31. A composition comprising:
the compound of claim 12, or a salt, solvate, hydrate, tautomer, stereoisomer, or isotopically labeled compound thereof; and
an excipient.

32. A kit comprising:
the compound of claim 12, or a salt, solvate, hydrate, tautomer, stereoisomer, or isotopically labeled compound thereof; and
instructions for using the compound, or a salt, solvate, hydrate, tautomer, stereoisomer, or isotopically labeled compound thereof.

33. A method of treating a bacterial infection in a subject in need thereof, the method comprising administering to the subject in need thereof an effective amount of the compound of claim 12, or a pharmaceutically acceptable salt, solvate, hydrate, tautomer, stereoisomer, or isotopically labeled compound thereof.

34. A method of inhibiting the formation of a bacterial biofilm, inhibiting the growth of a bacterial biofilm, reducing a bacterial biofilm, or clearing a bacterial biofilm, the method comprising contacting the bacterial biofilm with an effective amount of the compound of claim 12, or a salt, solvate, hydrate, tautomer, stereoisomer, or isotopically labeled compound thereof.

35. A method of inhibiting the growth of a bacterium, inhibiting the reproduction of a bacterium, inhibiting the viability of a bacterium, or killing a bacterium, the method comprising contacting the bacterium with an effective amount of the compound of claim 12, or a salt, solvate, hydrate, tautomer, stereoisomer, or isotopically labeled compound thereof.

36. A method of disinfecting a surface with respect to a bacterium on the surface, the method comprising contacting the surface with an effective amount of the compound of claim 12, or a salt, solvate, hydrate, tautomer, stereoisomer, or isotopically labeled compound thereof.

37. The method of claim 16, wherein the bacterial infection is caused by a Gram-positive bacterium.

38. The method of claim 37, wherein the Gram-positive bacterium is a species of *Staphylococcus*.

39. The method of claim 37, wherein the Gram-positive bacterium is a strain of *Staphylococcus aureus*.

40. The method of claim 37, wherein the Gram-positive bacterium is a methicillin-resistant strain of *Staphylococcus aureus* (MRSA).

41. The method of claim 37, wherein the Gram-positive bacterium is a strain of *Staphylococcus epidermidis*.

42. The method of claim 37, wherein the Gram-positive bacterium is a methicillin-resistant strain of *Staphylococcus epidermidis* (MRSE).

43. The method of claim 37, wherein the Gram-positive bacterium is a species of *Enterococcus*.

44. The method of claim 37, wherein the Gram-positive bacterium is a strain of *Enterococcus faecium* or *Enterococcus faecalis*.

45. The method of claim 37, wherein the Gram-positive bacterium is a vancomycin-resistant strain of *Enterococcus faecium*.

46. The method of claim 16, wherein the bacterial infection is caused by a Gram-negative bacterium.

47. The method of claim 46, wherein the Gram-negative bacterium is a species of *Streptococcus*.

48. The method of claim 46, wherein the Gram-negative bacterium is a strain of *Streptococcus pneumoniae*.

49. The method of claim 16, wherein the bacterial infection is caused by a *mycobacterium*.

50. The method of claim 49, wherein the *mycobacterium* is a strain of *Mycobacterium tuberculosis*.

51. The method of claim 33, wherein the bacterial infection is caused by a Gram-positive bacterium.

52. The method of claim 33, wherein the bacterial infection is caused by a Gram-negative bacterium.

53. The method of claim 33, wherein the bacterial infection is caused by a *mycobacterium*.

54. A method of treating a bacterial infection in a subject in need thereof, the method comprising administering to the subject in need thereof an effective amount of the compound of claim 11, or a pharmaceutically acceptable salt thereof.

55. A method of disinfecting a surface with respect to a bacterium on the surface, the method comprising contacting the surface with an effective amount of the compound of claim 11, or a salt thereof.

* * * * *